US009994881B2

(12) United States Patent
Gonzalez et al.

(10) Patent No.: US 9,994,881 B2
(45) Date of Patent: Jun. 12, 2018

(54) FUNCTIONALIZED CARBOXYLIC ACIDS AND ALCOHOLS BY REVERSE FATTY ACID OXIDATION IN ENGINEERED MICROBES

(71) Applicant: William Marsh Rice University, Houston, TX (US)

(72) Inventors: Ramon Gonzalez, Houston, TX (US); James M. Clomburg, Houston, TX (US)

(73) Assignee: William Marsh Rice University, Houston, TX (US)

( * ) Notice: Subject to any disclaimer, the term of this patent is extended or adjusted under 35 U.S.C. 154(b) by 397 days.

(21) Appl. No.: 14/199,528

(22) Filed: Mar. 6, 2014

(65) Prior Publication Data

US 2014/0273110 A1 Sep. 18, 2014

Related U.S. Application Data

(63) Continuation of application No. PCT/US2012/054230, filed on Sep. 7, 2012.

(60) Provisional application No. 61/531,911, filed on Sep. 7, 2011.

(51) Int. Cl.

| C12P 13/12 | (2006.01) |
|---|---|
| C12P 13/00 | (2006.01) |
| C12P 7/42 | (2006.01) |
| C12P 7/44 | (2006.01) |
| C12P 7/16 | (2006.01) |
| C12P 7/18 | (2006.01) |
| C12P 13/04 | (2006.01) |
| C12N 1/21 | (2006.01) |
| C12N 9/04 | (2006.01) |
| C12N 9/16 | (2006.01) |
| C12N 9/02 | (2006.01) |
| C12N 9/10 | (2006.01) |
| C12N 9/88 | (2006.01) |
| C12P 13/02 | (2006.01) |

(52) U.S. Cl.
CPC .............. *C12P 13/02* (2013.01); *C12N 9/001* (2013.01); *C12N 9/0006* (2013.01); *C12N 9/1029* (2013.01); *C12N 9/16* (2013.01); *C12N 9/88* (2013.01); *C12P 7/16* (2013.01); *C12P 7/18* (2013.01); *C12P 7/42* (2013.01); *C12P 7/44* (2013.01); *C12P 13/001* (2013.01); *Y02E 50/10* (2013.01)

(58) Field of Classification Search
CPC .. C12P 13/02; C12P 13/00; C12P 7/42; C12P 7/18; C12P 7/44
See application file for complete search history.

(56) References Cited

FOREIGN PATENT DOCUMENTS

| EP | 12829682.9 | 7/2014 |
|---|---|---|
| WO | WO2009111672 | 9/2009 |
| WO | 2010101651 | 9/2010 |
| WO | 201209176 | 8/2012 |
| WO | WO2012109176 | 8/2012 |
| WO | PCT/US2012/054230 | 1/2013 |
| WO | 2013036812 | 3/2013 |

OTHER PUBLICATIONS

Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Prather et al., Curr. Opin. Biotechnol. 19:468-474, 2008.*
Kizer et al., Appl. Environ. Microbiol. 74(10):3229-3241, 2008.*
Lehman, T. C., Hale, D. E., Bhala, A., and Thorpe, C. (1990) An Acyl-Coenzyme a Dehydrogenase Assay Utilizing the Feericenium Ion, Anal. Biochem. 186, 280-284.
Jansen and Wanders, (2006) Review: Alpha-Oxidation, Biochimica et Biophysica Acta 1763, 1403-1412.
Andrey Yu Gulevich et al: "Metabolic engineering of for 1-butanol biosynthesis through the inverted aerobic fatty acid beta-oxidation pathway", Biotechnology Letters, Springer Netherlands, Dordrecht, vol. 34, No. 3, 22 Nov. 2011 (Nov. 22, 2011), pp. 463-469.
Yan-Ning Zheng et al: "Optimization of 1-18 fatty alcohol biosynthesis pathway for selectively enhanced production of C12/14 and C16/18 fatty alcohols in engineered *Escherichia coli*", Microbial Cell Factories, Biomed Central, London, NL, vol. 11, No. 1, May 20, 2012 (May 20, 2012), p. 65.
Pinot F, Beisson F. (2011). Cytochrome P450 metabolizing fatty acids in plants: characterization and physiological roles. FEBS J, 278 (2), 195-205.
Nogales et al., (2007) Characterization of the last step of the aerobic phenylacetic acid degradation pathway, Microbiology 153:357-365.
Gobel et al., (2002) Degradation of Aromatics and Chloroaromatics by *Pseudomonas* sp. Strain B13: Cloning, Characterization, and analysis of sequences encoding 3-Oxoadipate:Succinyl-Coenzyme A (CoA) Transferase and 3-Oxoadipyl-CoA Tholase, J. Bac. 184: 216-223.
Eulberg et al., (1998) Characterization of a Protocatechuate Catabolic Gene Cluster from Rhodococcus opacus 1CP: Evidence for a merged enzyme with 4-carboxymuconolactone-decarbocylatng and 3-Oxoadipate Enol-Lactone-Hydrolyzing Activity, J. Bacteriol. 180:1072-1081.
Iwagami et al., (2000) Characterization of the Protocatechuic Acid Catabolic Gene Cluster from *Streptomyces* sp. Strain 2065, Appl. Environ. Microbiol. 66:1499-1508.

(Continued)

*Primary Examiner* — Delia M Ramirez

(74) *Attorney, Agent, or Firm* — Boulware & Valoir

(57) ABSTRACT

Bacteria that run the beta oxidation cycle in reverse anabolic direction are provided, along with many novel primers to start the reverse cycle, pathways to make such primers, and a large variety of products produced thereby. Methods for making desired product by using such primers in the reverse pathway are also disclosed.

12 Claims, 39 Drawing Sheets

(56) References Cited

OTHER PUBLICATIONS

Rude, M. A., and Schirmer, A. (2009) New microbial fuels: a biotech perspective, Curr. Opin. Microbiol. 12, 274-281.

Lee, J. W., Na, D., Park, J. M., Lee, J., Choi, S., and Lee, S. Y. (2012) Systems metabolic engineering of microorganisms for natural and non-natural chemicals, Nat. Chem. Biol. 8, 536-546.

Peralta-Yahya, P. P., Zhang, F., Del Cardayre, S. B., and Keasling, J. D. (2012) Microbial engineering for the production of advanced biofuels, Nature 488, 320-328.

Steen, E. J., Kang, Y. S., Bokinsky, G., Hu, Z. H., Schirmer, A., McClure, A., Del Cardayre, S. B., and Keasling, J. D. (2010) Microbial production of fatty-acid-derived fuels and chemicals from plant biomass, Nature 463, 559-U182.

Handke, P., Lynch, S. A., and Gill, R. T. (2011) Application and engineering of fatty acid biosynthesis in *Escherichia coli* for advanced fuels and chemicals, Metab. Eng. 13, 28-37.

Lennen, R. M., Braden, D. J., West, R. M., Dumesic, J. A., and Pfleger, B. F. (2010) A Process for Microbial Hydrocarbon Synthesis: Overproduction of Fatty Acids in *Escherichia coli* and Catalytic Conversion to Alkanes, Biotechnol. Bioeng. 106, 193-202.

Dellomonaco, C., Clomburg, J. M., Miller, E. N., and Gonzalez, R. (2011) Engineered reversal of the β-oxidation cycle for the synthesis of fuels and chemicals, Nature 476, 355-359.

Keasling, J. D. (2008) Synthetic biology for synthetic chemistry, ACS Chem. Biol. 3, 64-76.

Clomburg, J. M., and Gonzalez, R. (2010) Biofuel production in *Escherichia coli*: the role of metabolic engineering and synthetic biology, Appl. Microbiol. Biotechnol. 86, 419-434.

Feigenbaum, J., and Schulz, H. (1975) Thiolases of *Escherichia coli*: Purification and Chain-Length Specificties, J. Bacteriol. 122, 407-411.

Jenkins, L. S., and Nunn, W. D. (1987) Genetic and Molecular Characterization of the Genes Involved in Short-Chain Fatty-Acid Degradation in *Escherichia coli*: The Ato System, J. Bacteriol. 169, 42-52.

Yang, S. Y., Yang, X. Y. H., Healy-Louie, G., Schulz, H., and Elzinga, M. (1990) Nucleotide Sequence of the fadA Gene: Primary Structure of the 3-ketoacyl-Coenzyme A Thiolase from *Escherichia coli* and the Structural Organization of the fadBA Operon, J. Biol. Chem. 265, 10424-10429.

Teufel, R., Mascaraque, V., Ismail, W., Voss, M., Perera, J., Eisenreich, W., Haehnel, W., and Fuchs, G. (2010) Bacterial phenylalanine and phenylacetate catabolic pathway revealed, Proc. Natl. Acad. Sci. U.S.A. 107, 14390-14395.

He, X. Y., and Yang, S. Y. (1997) Glutamate-119 of the large alpha-subunit is the catalytic base in the hydration of 2-trans-enoyl-coenzyme A catalyzed by the multienzyme complex of fatty acid oxidation from *Escherichia coli*, Biochemistry 36, 11044-11049.

Campbell, J. W., Morgan-Kiss, R. M., and Cronan, J. E. (2003) A new *Escherichia coli* metabolic competency: growth on fatty acids by a novel anaerobic β-oxidation pathway, Mol. Microbiol. 47, 793-805.

Gulevich, A. Y., Skorokhodova, A. Y., Sukhozhenko, A. V., Shakulov, R. S., and Debabov, V. G. (2012) Metabolic engineering of *Escherichia coli* for 1-butanol biosynthesis through the inverted aerobic fatty acid β-oxidation pathway, Biotechnol. Lett. 34, 463-469.

Walt, A., and Kahn, M. L. (2002) The fixA and fixB genes are necessary for anaerobic carnitine reduction in *Escherichia coli*, J. Bacteriol. 184, 4044-4047.

Eichler, K., Buchet, A., Bourgis, F., Kleber, H. P., and Mandrandberthelot, M. A. (1995) The fix *Escherichia coli* region contains 4 genes related to carnitinie metabolism, J. Basic Microbiol. 35, 217-227.

Akhtar, M. K., and Jones, P. R. (2009) Construction of a synthetic YdbK-dependent pyruvate:H-2 pathway in *Escherichia coli* BL21(DE3), Metab. Eng. 11, 139-147.

Hoffmeister, M., Piotrowski, M., Nowitzki, U., and Martin, W. (2005) Mitochondrial trans-2-enoyl-CoA reductase of wax ester fermentation from Euglena gracilis defines a new family of enzymes involved in lipid synthesis, J. Biol. Chem. 280, 4329-4338.

Inui, H., Miyatake, K., Nakano, Y., and Kitaoka, S. (1984) Fatty Acid Synthesis in Mitochondria of Euglena gracilis, Eur. J. Biochem. 142, 121-126.

Inui, H., Miyatake, K., Nakano, Y., and Kitaoka, S. (1983) Production and Composition of Wax Esters by Fermentation of Euglena gracilis, Agric. Biol. Chem. 47, 2669-2671.

Cho, H. S., and Cronan, J. E. (1993) *Escherichia coli* thioesterase I, molecular cloning and sequencing of the structural gene and identification as a periplasmic enzyme, J. Biol. Chem. 268, 9238-9245.

Nie, L., Ren, Y., Janakiraman, A., Smith, S., and Schulz, H. (2008) A novel paradigm of fatty acid β-oxidation exemplified by the thioesterase-dependent partial degradation of conjugated linoleic acid that fully supports growth of *Escherichia coli*, Biochemistry 47, 9618-9626.

Zhuang, Z. H., Song, F., Zhao, H., Li, L., Cao, J., Eisenstein, E., Herzberg, O., and Dunaway-Mariano, D. (2008) Divergence of function in the hot dog fold enzyme superfamily: The bacterial thioesterase YciA, Biochemistry 47, 2789-2796.

Feng, Y., and Cronan, J. E. (2009) A New Member of the *Escherichia coli* fad Regulon: Transcriptional Regulation of fadM (ybaW), J. Bacteriol. 191, 6320-6328.

Vlessis, A. A., Bartos, D., and Trunkey, D. (1990) Importance of spontaneous alpha-ketoacid decarboxylation in experiments involving peroxide, Biochem. Biophys. Res. Comm. 170, 1281-1287.

Yazdani, S. S., and Gonzalez, R. (2007) Anaerobic fermentation of glycerol: a path to economic viability for the biofuels industry, Curr. Opin. Biotechnol. 18, 213-219.

Kang, Y. S., Durfee, T., Glasner, J. D., Qiu, Y., Frisch, D., Winterberg, K. M., and Blattner, F. R. (2004) Systematic mutagenesis of the *Escherichia coli* genome, J. Bacteriol. 186, 8548-8548.

Yazdani, S. S., and Gonzalez, R. (2008) Engineering *Escherichia coli* for the efficient conversion of glycerol to ethanol and co-products, Metab. Eng. 10, 340-351.

Baba, T., Ara, T., Hasegawa, M., Takai, Y., Okumura, Y., Baba, M., Datsenko, K. A., Tomita, M., Wanner, B. L., and Mori, H. (2006) Construction of *Escherichia coli* K-12 in-frame, single-gene knock-out mutants: the Keio collection, Mol. Syst. Biol. 2, 11.

Neidhardt, F. C., Bloch, P. L., and Smith, D. F. (1974) Culture Medium for Enterobacteria, J. Bacteriol. 119, 736-747.

Dharmadi, Y., Murarka, A., and Gonzalez, R. (2006) Anaerobic fermentation of glycerol by *Escherichia coli*: A new platform for metabolic engineering, Biotechnol. Bioeng. 94, 821-829.

Dharmadi, Y., and Gonzalez, R. (2005) a better global resolution function and a novel iterative stochastic search method for optimization of high-performance liquid chromatographic separation, J Chromatogr., A 1070, 89-101.

Kitagawa, M., Ara, T., Arifuzzaman, M., Ioka-Nakamichi, T., Inamoto, E., Toyonaga, H., and Mori, H. (2005) Complete set of ORF clones of *Escherichia coli* ASKA library (A complete Set of *E. coli* K-12 ORF archive): Unique resources for biological research, DNA Res. 12, 291-299.

O'Brien, W. J., and Frerman, F. E. (1977) Evidence for a Complex of 3 β-Oxidation Enzymes in *Escherichia coli*: Induction and Localization, J. Bacteriol. 132, 532-540.

Bond-Watts, B. B., Bellerose, R. J., and Chang, M. C. Y. (2011) Enzyme mechanism as a kinetic control element for designing synthetic biofuel pathways, Nat. Chem. Biol. 7, 222-227.

Wiesenborn, D. P., Rudolph, F. B., and Papoutsakis, E. T. (1988) Thiolase from Clostridium acetobutylicum ATCC-824 and its Role in the Synthesis of Acids and Solvents, Appl. Environ. Microbiol. 54, 2717-2722.

Hartmanis, M. G. N., and Gatenbeck, S. (1984) Intermediary Metabolism in Clostridium acetobutylicum: Levels of Enzymes Involved in the Formation of Acetate and Butyrate, Appl. Environ. Microbiol. 47, 1277-1283.

(56) References Cited

OTHER PUBLICATIONS

Trinh, "Metabolic Engineering of *Escherichia Coli* for Efficient Conversion of Glycerol to Ethanol", Appl. Environ. Microbiol. 2009, 75(21).

* cited by examiner

FIG. 2 (CONTINUATION)

Legend for Figures 1 and 2 (All thiolases with the proposed potential to condense functionalized primers with acetyl-CoA; E.C.: 2.3.1.9/16/174 or 2.3.1.- for broad definition)

| Enzyme/Gene Name | Protein Accession Number | Organism | References (where available) |
|---|---|---|---|
| AtoB | NP_416728.1 | Escherichia coli | AtoB: Sato et al., 2007, J. Biosci. Bioeng. 103:38-44 |
| BktB | CAJ92580.1 | Ralstonia eutropha | Slater et al., 1998, J Bacteriol 180:1979-1987 |
| CatF | AAL02407.1 | Pseudomonas sp. strain B13 | Gobel et al., 2002, J. Bacteriol. 184: 216-223 |
| CatF | | Rhodococcus opacus | |
| FadA | YP_026272.1 | Escherichia coli | |
| PaaJ | NP_415915.1 | Escherichia coli | Mascaraque et al., 2010, PNAS 107:14390–14395; Nogales et al., 2007, Microbiology 153:357-365 |
| PcaF | YP_002778248.1 | Rhodococcus opacus | Eulberg et al., 1998, J. Bacteriol. 180:1072-1081 |
| PcaF | AAD22035.1 | Streptomyces sp. 2065 | Iwagami et al., 2000, Appl. Environ. Microbiol. 66:1499-1508 |
| PhaA | YP_725941.1 | Ralstonia eutropha | Sato et al., 2007, J. Biosci. Bioeng. 103:38-44) |
| ThlA | AAC26023.1 | Clostridium acetobutylicum | Winzer et al., 2000, J. Mol. Microbiol. Biotechnol. 2:531-541 |
| ThlB | AAC26026.1 | Clostridium acetobutylicum | Winzer et al., 2000, J. Mol. Microbiol. Biotechnol. 2:531-541 |
| YqeF | NP_417321.2 | Escherichia coli | |

FIG. 3 (CONTINUATION)
Legend for Figure 3

| Rxn #[a] | Enzyme/Gene | E.C. # | Accession Number | Organism[b] |
|---|---|---|---|---|
| (1) | N/A | N/A | N/A | N/A |
| (2) | phosphoenolpyruvate carboxylase (ppc) | 4.1.1.31 | NP_418391.1 | Escherichia coli |
|  | phosphoenolpyruvate carboxykinase (pck) | 4.1.1.49 | NP_417862.1 | Escherichia coli |
|  | pyruvate carboxylase (pyc) | 6.4.1.1 | AAF09095.1 | Lactococcus lactis |
| (3) | malate dehydrogenase (mdh) | 1.1.1.37 | NP_417703.1 | Escherichia coli |
| (4) | malate synthase (glcB) | 2.3.3.9 | NP_417450.1 | Escherichia coli |
| (5) | glyoxylate oxidase | 1.2.3.5 | See Refs | See Refs |
| (6) | oxaloacetate acetylhydrolase (oahA) | 3.7.1.1 | AAS99938.1 | Botryotinia fuckeliana |
| (7a) | glyoxylate dehydrogenase | 1.2.1.17 | See Refs | Pseudomonas fluorescens |
| (7b) | oxalate CoA-transferase | 2.8.3.2 | See Refs | Cupriavidus oxalaticus |
| (7c) | formyl-CoA transferase | 2.8.3.16 | NP_416875.1 | Escherichia coli |
|  |  |  | AAC45298.1 | Oxalobacter formigenes |
| (7d) | oxalyl-CoA synthetase | 6.2.1.8 | See Refs | Lathyrus sativus |
| (8) | Fumarate hydratase | 4.2.1.2 | NP_416129.1 | Escherichia coli |
|  |  |  | NP_418546.1 | Escherichia coli |
|  |  |  | NP_416128.1 | Escherichia coli |
| (9) | Fumarate Reductase | 1.3.5.4 | NP_418578.1, NP_418577.1, NP_418576.1, and NP_418575.1 (4 subunits) | Escherichia coli |
|  | Succinate Dehydrogenase | 1.3.99.1 | NP_415251.1, NP_415252.1, NP_415249.1, and NP_415250.1 (4 subunits) | Escherichia coli |
|  | NADH Dependent Fumarate Reductase | 1.3.1.6 | AAN40014.1 | Trypanosoma brucei |
| (10) | succinyl-CoA synthetase/ligase | 6.2.1.5 | AAC73822.1 and AAC73823.1 (2 subunits) | Escherichia coli |

FIG. 3 (CONTINUATION)
Legend for Figure 3

| Rxn # | Enzyme/Gene | E.C. # | Accession Number | Organism[b] |
|---|---|---|---|---|
| (11) | pyruvate dehydrogenase complex | 1.2.4.1 | NP_414656.1, NP_414657.1, and NP_414658.1 (3 subunits) | *Escherichia coli* |
|  | pyruvate formate-lyase | 2.3.1.54 | NP_415423.1 | *Escherichia coli* |
|  | pyruvate:flavodoxin/ferredoxin oxidoreductase | 1.2.7.1 | NP_415896.1 | *Escherichia coli* |
| (12a) | acetyl-CoA carboxylase (*accABCD*) | 6.4.1.2 | NP_414727.1, NP_417721.1, NP_417722.1, and NP_416819.1 (4 subunits) | *Escherichia coli* |
| (12b) | malonyl-CoA:pyruvate carboxytransferase | 2.1.3.1 | CBL57378.1, YP_003688799.1, and CBL57376.1 (3 subunits) | *Propionibacterium freudenreichii* |
| (13) | malic enzyme | 1.1.1.38 | NP_415996.2 | *Escherichia coli* |
|  |  | 1.1.1.40 | NP_416958.1 | *Escherichia coli* | a: Represents common carbon utilization and glycolytic pathways general to all organisms
b: When available, representative enzyme/gene from *E. coli* selected although in the majority of cases these enzymes are not limited to *E. coli*

References
Glyoxylate oxidase: Ghisla S and Massey V. 1980. J. Biol. Chem. 255:5688-5696.; Kasai T, Suzuki I, and Asai T. 1962. Koso Kogaku Shimpojiumii 17:77-81.; Akamatsu Y and Shimada M. 1994. Phytochemistry 37:649-653.
Glyoxylate dehydrogenase: Singh, R.; Lemire, J.; Mailloux, R.J.; Chenier, D.; Hamel, R.; Appanna, V.D.; *PLoS ONE 4*, e7344 (2009); Quayle J.R. and Taylor G.A. 1961. Biochem. J. 78:611-615.
Oxalate CoA transferase: Quayle et al. Biochem J. 1961 78:225-236.
Oxalyl-CoA synthetase: Giovanelli, J. 1966. Biochim. Biophys. Acta. 118:124-143; Sehgal, D.; Santha, I.M.; Mehta, S.L. 1992. J. Plant Biochem. Biotechnol. 1:97-100
NADH Dependent Fumarate Reductase: Besteiro S, Biran M, Biteau N, Coustou V, Baltz T, Canioni P, Bringaud F. 2002. J. Biol. Chem. 277:38001-38012.

FIG. 4 (CONTINUATION)

Legend for Figure 4

| Rxn # | Enzyme | E.C. # | Accession Number | Organism |
|---|---|---|---|---|
| (1)[a] | N/A | | N/A | N/A |
| (2) | D-Glycerate-3-phosphate phosphohydrolase | 3.1.3.38 | See Refs | See Refs |
| (3) (2 Steps) | Glycerol-3-phosphate dehydrogenase | 1.1.1.8 1.1.1.94 | NP_010262.1 | Saccharomyces cerevisiae |
| | glycerol-3-phosphatase | 3.1.3.21 | NP_012211.2 NP_010984.3 | Saccharomyces cerevisiae Saccharomyces cerevisiae |
| (4) | Glycerol oxidoreductase | 1.1.1.21 1.1.1.72 | See Refs | See Refs |
| (5) | D-Glyceraldehyde oxidoreductase | 1.2.1.3 | See Refs | Bos taurus |
| | glyceraldehyde ferredoxin oxidoreductase | 1.2.7.5 | See Refs | Pyrococcus furiosus |
| (6) | D-Glycerate oxidoreductase | 1.1.1.29 1.1.1.81 | NP_415551.2 NP_418009.2 | Escherichia coli Escherichia coli |
| (7) | Pyruvate dehydrogenase complex (specific for hydroxypyruvate) | | See Refs | See Refs |
| (8) | Hydroxypyruvate decarboxylase | 4.1.1.40 | See Refs | Rattus norvegicus |
| (9) | glycolaldehyde oxidoreductase | 1.2.1.21 | NP_415933.1 | Escherichia coli |
| (10) | Engineered Enzyme | | | |
| (11)[a] | N/A | | N/A | N/A |
| (12) | phosphoenolpyruvate carboxylase | 4.1.1.31 | NP_418391.1 | Escherichia coli |
| | phosphoenolpyruvate | 4.1.1.49 | NP_417862.1 | Escherichia coli |

FIG. 4 (CONTINUATION)
Legend for Figure 4

| Rxn # | Enzyme | E.C. # | Accession Number | Organism |
|---|---|---|---|---|
| (13) | pyruvate carboxykinase carboxylase | 6.4.1.1 | AAF09095.1 | Lactococcus lactis |
| (13) | malate dehydrogenase | 1.1.1.37 | NP_417703.1 | Escherichia coli |
| (14) | malate synthase | 2.3.3.9 | NP_417450.1 | Escherichia coli |
| (15) | glyoxylate reductase | 1.1.1.79 | NP_415551.2 | Escherichia coli |
| | | | NP_418009.2 | Escherichia coli |
| (16) | Fumarate hydratase | 4.2.1.2 | NP_416129.1 | Escherichia coli |
| | | | NP_418546.1 | Escherichia coli |
| | | | NP_416128.1 | Escherichia coli |
| (17) | Fumarate Reductase | 1.3.5.4 | NP_418578.1, NP_418577.1, NP_418576.1, and NP_418575.1 (4 subunits) | Escherichia coli |
| | Succinate Dehydrogenase | 1.3.99.1 | NP_415251.1, NP_415252.1, NP_415249.1, and NP_415250.1 (4 subunits) | Escherichia coli |
| | NADH Dependent Fumarate Reductase | 1.3.1.6 | AAN40014.1 | Trypanosoma brucei |
| (18) | succinyl-CoA synthetase/ligase | 6.2.1.5 | AAC73822.1 and AAC73823.1 (2 subunits) | Escherichia coli |
| (19) | succinate-semialdehyde oxidoreductase | 1.2.1.76 | AAA92347.1 | Clostridium kluyveri |
| (20) | 4-Hydroxybutanoate oxidoreductase (succinate semialdehyde reducatse) | 1.1.1.61 | 1.1.1.61 | Escherichia coli |
| (21) | 4-hydroxybutyrate:CoA synthetase/ligase | 6.2.1.- | YP_0011191504.1 | Metallophaera sedula |
| | acetyl-CoA: 4-hydroxybutanoate CoA transferase | 2.8.3.- | CAB60036.2 | Clostridium aminobutyricum | a: Represents common carbon utilization and glycolytic pathways general to all organisms

FIG. 4 (CONTINUATION)

Legend for Figure 4

| Rxn # | Enzyme | E.C. # | Accession Number | Organism |
|---|---|---|---|---|

References

D-Glycerate-3-phosphate phosphohydrolase: Randall DD and Tolbert NE. 1971. J.Biol. Chem. 246:5510-5517.

Glycerol oxidoreductase: Toews CJ. 1967. Biochem. J. 105:1067-1073; Viswanath-Reddy M, Pyle JE, and Branch Howe E. 1978. J. Gen. Microbiol. 107, 289-296.

D-Glyceraldehyde oxidoreductase: Ting HH and Crabbe MJC. 1983. Biochem. J. 215:361-368.

Glyceraldehyde ferredoxin oxidoreductase : Mukund S and Adams MW. 1991. J. Biol. Chem. 266:14208-14216.

Pyruvate dehydrogenase complex (specific for hydroxypyruvate): Camp and Randal, 1985, Plant Physiol. 77:571-577

Hydroxypyruvate decarboxylase: Hendrick JL and Sallach HJ. 1964. Arch. Biochem. Biophys. 105:261-9.

NADH Dependent Fumarate Reductase: Besteiro S, Biran M, Biteau N, Coustou V, Baltz T, Canioni P, Bringaud F. 2002. J. Biol. Chem. 277:38001-38012.

succinate-semialdehyde oxidoreductase: Sohling B. and Gottschalk G. 1993. Eur. J. Biochem. 212, 121-127 acetyl-CoA: 4-hydroxybutanoate CoA transferase : Scherf U and Buckel W. 1991. Appl. Environ. Microbiol. 57:2699-2702.; Macieira S, Zhang J, Velarde M, Buckel W, and Messerschmidt A.2009. J. Biol Chem. 390:1251-63.

FIG. 5 (CONTINUATION)
Legend for Figure 5

| Rxn # | Enzyme/Gene | E.C. # | Accession Number | Organism |
|---|---|---|---|---|
| (1)[a] | N/A | N/A | N/A | N/A |
| (2) | D-lactate dehydrogenase (ldhA) | 1.1.1.28 | NP_415898.1 | Escherichia coli |
| (3) | propionate CoA-transferase | 2.8.3.1 | CAB77207.1 | Clostridium propionicum |
| (4) | lactoyl-CoA hydratase | 4.2.1.54 | JN244652.1 and JN244651.1 (2 subunits) | Clostridium propionicum |
| (5) | 3-Hydroxypropionyl-CoA dehydratase | 4.2.1.116 | YP_001192065.1 | Metallosphaera sedula |
| (6) | glycerol dehydratase | 4.2.1.30 | AAB48850.1, AAB48851.1, and AAB48852.1 (3 subunits) | Citrobacter freundii |
| (7) | g-glutamyl-g-aminobutyraldehyde dehydrogenase | 1.2.1.- | NP_415816.1 | Escherichia coli |
| (8) | 3-hydroxypropionate CoA synthase | 6.2.1.36 | ABP95613.1 ACJ71674.1 | Metallosphaera sedula Sulfolobus tokodaii |
| (9) | pyruvate dehydrogenase complex | 1.2.4.1 | NP_414656.1, NP_414657.1, and NP_414658.1 (3 subunits) | Escherichia coli |
|  | pyruvate formate-lyase (pflB) | 2.3.1.54 | NP_415423.1 | Escherichia coli |
|  | pyruvate:flavodoxin/ferredoxin oxidoreductase | 1.2.7.1 | NP_415896.1 | Escherichia coli |
| (10a) | acetyl-CoA carboxylase (accABCD) | 6.4.1.2 | NP_414727.1, NP_417721.1, NP_417722.1, and NP_416819.1 (4 subunits) | Escherichia coli |
| (10b) | malonyl-CoA:pyruvate carboxytransferase | 2.1.3.1 | CBL57378.1, YP_003688799.1, and CBL57376.1 (3 subunits) | Propionibacterium freudenreichii |

FIG. 5 (CONTINUATION)

Legend for Figure 5

| Rxn # | Enzyme/Gene | E.C. # | Accession Number | Organism |
|---|---|---|---|---|
| (11) | malic enzyme | 1.1.1.38 | NP_415996.2 | *Escherichia coli* |
|  |  | 1.1.1.40 | NP_416958.1 | *Escherichia coli* |
| (12) | malonyl CoA reductase | 1.2.1.75 | AAS20429.1 | *Chloroflexus aurantius* |
| (13) | malonate semialdehyde reductase | 1.1.1.59 | AAS20429.1 | *Chloroflexus aurantius* |
|  |  | 1.1.1.298 | YP_004408885.1 | *Metallosphaera cuprina* |
| (14) | Glycerol-3-phosphate dehydrogenase | 1.1.1.8 | NP_010262.1 | *Saccharomyces cerevisiae* |
|  |  | 1.1.1.94 |  |  |
| 2 Steps | glycerol-3-phosphatase | 3.1.3.21 | NP_012211.2 | *Saccharomyces cerevisiae* |
|  |  |  | NP_010984.3 | *Saccharomyces cerevisiae* | a: Represents common carbon utilization and glycolytic pathways general to all organisms

References lactoyl-CoA hydratase: Brunelle, S.L.; Abeles, R.H.; Bioorg. Chem. 21, 118-126 (1993)
3-Hydroxypropionyl-CoA dehydratase: Teufel, R.; Kung, J.; Kockelkorn, D.; Alber, B.; Fuchs, G.; J. Bacteriol. 191, 4572-4581 (2009)
3-hydroxypropionate CoA synthase: Alber, B.E.; Kung, J.W.; Fuchs, G.; J. Bacteriol. 190, 1383-1389 (2008)
malonyl CoA reductase and malonate semialdehyde reductase: Huegler, M.; Menendez, C.; Schaegger, H.; Fuchs, G.; J. Bacteriol. 184, 2404-2410 (2002)

FIG. 6 (CONTINUATION)

| Legend for Figure 6 | | | | |
|---|---|---|---|---|
| Reaction | Enzyme/Gene | E.C. # | Accession Number | Organism |
| (1) | Fatty acid oxidoreductase (ω-hydroxylating) | 1.14.15.3 | NP_000769.2 | Homo sapiens |
| | | 1.14.14.- | ABA61323.1 | Arabidopsis thaliana |
| | | | ACG43035.1 | Zea mays |
| | | | P10615.3 | Candida tropicalis |
| (2) | Alcohol oxidoreductase | 1.1.1.1 | See Refs | See Refs |
| | | 1.1.1.71 | | |
| | | 1.1.3.13 | | |
| | | 1.1.99.20 | | |
| (3) | Aldehyde oxidoreductase | 1.2.99.3/6/7 | See Refs | See Refs |
| | | 1.2.1.3/5 | | |
| (4) | Fatty Acid α-hydroxylase | 1.14.14.1 | ABF89872.1 | Myxococcus xanthus |
| | | | ZP_01460762.1 | Stigmatella aurantiaca |

References

Fatty Acid ω-hydroxylases (Cytochrome P450): Coon MJ. 2005. Biochem. Biophys. Res. Commun. 338: 378-385
Alcohol oxidoreductase: Kawai F, Yamanaka H, Ameyama M, Shinagawa E, Matsushita K, Adachi O. 1985. Agric. Biol. Chem. 49:1071-1076; Yasuda M, Cherepanov A, Duine JA. 1996. FEMS Microbiol. Lett. 138:23-28
Aldehyde oxidoreductase: Hommel R and Kleber HP 1984. FEMS Microbiol. Lett. 22, 139-142; Shinagawa E, Toyama H, Matsushita K, Tuitemwong P, Theeragool G, Adachi O. 2006. Biosci. Biotechnol. Biochem. 70:850-857; Groen B, Frank J, Duine JA. 1984. Biochem. J. 223: 921-924; Zarnt G, Schräder T, Andreesen JR. 2001 J. Bacteriol. 183:1954-1960
Fatty Acid α-hydroxylases: Ring MW, Schwar G, Bode HB. 2009. ChemBioChem 10:2003-20

FIG. 7 (CONTINUATION)

| Legend for Figure 7 | | | | |
|---|---|---|---|---|
| Reaction | Enzyme | E.C. # | Accession Number | Organism[a] |
| (1) | Thioesterase | 3.2.1.- | NP_415027.1 | *Escherichia coli* |
| | | | NP_414986.1 | *Escherichia coli* |
| | | | NP_415769.1 | *Escherichia coli* |
| | | | NP_414977.1 | *Escherichia coli* |
| | | | NP_416201.1 | *Escherichia coli* |
| | | | NP_415264.1 | *Escherichia coli* |
| | | | NP_415914.1 | *Escherichia coli* |
| | | | NP_415129.1 | *Escherichia coli* |
| | | | AAH05792.1 | *Mus musculus* |
| | | | AAR21571.1 | *Arabidopsis thaliana* |
| | | | AAD27617.1 | *Saccharomyces cerevisiae* |
| (2) | CoA-dependent aldehyde dehydrogenase | 1.2.1.- | YP_047869.1 | *Acinetobacter calcoaceticus* |
| | | | BAB85476.1 | *Acinetobacter sp.* Strain M-1 |
| | | | P38947.2 | *Clostridium kluyveri* |
| (3) | carboxylic acid reductase (CAR)/aldehyde dehydrogenase/ aldehyde oxidoreductase | 1.2.99.6 1.2.99.7 1.2.7.5 | AAR91681.1 | *Nocardia iowensis* |
| (4) | Transaminase | 2.6.1.- | NP_417148.1 | *Escherichia coli* |
| | | | NP_766549.2 | *Mus musculus* |
| | | | YP_257332.1 | *Pseudomonas fluorescens* |
| | | | NP_999428.1 | *Sus scrofa* |
| | | | YP_001823341.1 | *Streptomyces griseus* |
| | lysine-6-dehydrogenases | 1.4.1.18 | BAB39707.1 | *Geobacillus stearothermophilus* |
| | | | AAZ94428.1 | *Achromobacter denitrificans* |
| | | | NP_353966.1 | *Agrobacterium tumefaciens* |

FIG. 7 (CONTINUATION)

Legend for Figure 7

| Reaction | Enzyme | E.C. # | Accession Number | Organism[a] |
|---|---|---|---|---| a: When available, representative enzyme/gene from *E. coli* selected although in the majority of cases these enzymes are not limited to *E. coli*

References fatty acyl-CoA reductase from *Acinetobacter calcoaceticus*: Reiser and Somerville, 1997, J. Bacteriol. 179:2969-2975 fatty acyl-CoA reductase from *Acinetobacter* sp. Strain M-1: Ishige et al., 2002, Appl. Environ, Microbiol. 68:1192-1195

*sucD* gene from *Clostridium kluyveri*: Sohling and Gottschalk, 1996, J. Bacteriol. 178:871-880

CAR from *Nocardia*: Venkitasubramanian et al., 2008, Enzyme Microb.Technol. 42:130-137

Transaminases: Bartsch et al., 1990, J. Bacteriol. 172:7035-7042; Cooper, 1985,Methods Enzymol.113, 80-82; Scott and Jacoby, 1959, J. Biol. Chem. 234, 932-936; Yonaha et al., 1985, *Eur. J. Biochem.* 146:101-106.

Lysine Dehydrogenases: Heydari et al., 2004,Appl. Environ. Microbiol. 70, 937-942; Hashimoto et al., 1989,*Agric. Biol. Chem.* 53, 1175-1176; Ruldeekulthamrong et al., 2008,*BMB Rep.* 41, 790-795.

SEQUENCE LISTING

<160> NUMBER OF SEQ ID NOS: 46

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 1
ttaaagagga gaaaggtacc atgcaaacac aaatcaaagt                     40

<210> SEQ ID NO 2
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 2
ttaaagagga gaaaggtacc atgatgaact tcaacaatgt tttc                44

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 3
ttaaagagga gaaaggtacc atgagtcagg cgctaaaaaa                     40

<210> SEQ ID NO 4
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 4
ttaaagagga gaaaggtacc gtgaatacaa cgctgtttcg at                  42

<210> SEQ ID NO 5
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 5
ttaaagagga gaaaggtacc atgtctacaa cacataacgt ccc                 43

<210> SEQ ID NO 6
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 6
ttaaagagga gaaaggtacc atgattacta ttgacggtaa tggc                44

<210> SEQ ID NO 7
<211> LENGTH: 42
<212> TYPE: DNA
<213> ORGANISM: Artificial Sequence

```
<220> FEATURE:
<223> OTHER INFORMATION: Synthetic oligonucleotide

<400> SEQUENCE: 7
ttaaagagga gaaaggtacc atgatatgga aacggaaaat ca                42

<210> SEQ ID NO 8
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 8
gcagaagatc acgcgaaata aggaggaata aaccatggca atgtttacca cgac     54

<210> SEQ ID NO 9
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 9
tttaaccact acgcgaataa ggaggaataa accatggcaa tgtttaccac gac      53

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 10
ttaaatgctg cggccatcgg agatggttcc gtatg                         35

<210> SEQ ID NO 11
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 11
gaggaataaa ccatgaaaaa ttgtgtcatc gtca                          34

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
taagaattcg aagctgcgga ttcaggagac tgaca                         35

<210> SEQ ID NO 13
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 13
aaacggctta aagctaataa ggaggaataa accatggatt taatttaaa tgatgagcag  60
```

```
<210> SEQ ID NO 14
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 14
aaacggctta aagctaataa ggaggaataa accatggatt tttctttaac tgaagaaca        59

<210> SEQ ID NO 15
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 15
aaacggctta aagctaataa ggaggaataa accatggcaa tgtttaccac gac              53

<210> SEQ ID NO 16
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 16
aaacggctta aagctaataa ggaggaataa accatgatga ttttgagtat tctcgctac        59

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 17 cccttttcata tggaacaggt tgtcattgtc                                       30

<210> SEQ ID NO 18
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 18
cggcacatgg cccatgtgct ccacgccgcc aaccag                                 36

<210> SEQ ID NO 19
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 19
ctggttggcg gcgtggagca catgggccat gtgccg                                 36

<210> SEQ ID NO 20
<211> LENGTH: 34
<212> TYPE: DNA
<213> ORGANISM: Artificial Sequence
<220> FEATURE:
<223> OTHER INFORMATION: Synthetic oligonucleotide
```

```
<400> SEQUENCE: 20
ggaaaagcgg ccgcttaaac ccgctcaaac accg                                   34

<210> SEQ ID NO 21
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 21
ttttcccata tgctttacaa aggcgacac                                         29

<210> SEQ ID NO 22
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 22
cagcagccct tttagatccg attgctgttc cagcac                                 36

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 23
gtgctggaac agcaatcgga tctaaaaggg ctgctg                                 36

<210> SEQ ID NO 24
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 24
ggtcggcacc ggcaggtctt ccaggcgatt aaacac                                 36

<210> SEQ ID NO 25
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 25
gtgtttaatc gcctggaaga cctgccggtg ccgacc                                 36

<210> SEQ ID NO 26
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 26
ccaaaagcgg ccgcttaagc cgttttcagg tc                                     32

<210> SEQ ID NO 27
```

<210> SEQ ID NO 27
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 27
aaacccagat ctatgaaaaa ggtatgtgtt atag                          34

<210> SEQ ID NO 28
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 28
ttaaaactcg agttttgaat aatcgtagaa ac                            32

<210> SEQ ID NO 29
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 29
gaggaataaa ccatgcatca tcatcatcat catgcaatgt ttaccacgac cgcga    55

<210> SEQ ID NO 30
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 30
cccaagcttc gaattcttat tgctgtgctg cggacgg                       37

<210> SEQ ID NO 31
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 31
tgcctctagc acgcgtcgtt tacttaacca tctgctcca                     39

<210> SEQ ID NO 32
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 32
tgcctctagc acgcgttccg ttgctttatg agtcatg                       37

<210> SEQ ID NO 33
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 33
tgcctctagc acgcgtaaca gccggacggt tttc                34

<210> SEQ ID NO 34
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 34
tgcctctagc acgcgttcac tgcttaaact ccgcga                36

<210> SEQ ID NO 35
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 35
tgcctctagc acgcgtttca gtaagcagaa agtcaaaagc                40

<210> SEQ ID NO 36
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 36
tgcctctagc acgcgtgcat ttaatcggtg ttgcttt                37

<210> SEQ ID NO 37
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 37
tgcctctagc acgcgtggtg acaacgtcac aaaatgg                37

<210> SEQ ID NO 38
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 38
tgcctctagc acgcgtgcgg ccgcttattg ctgtgctgcg gac                43

<210> SEQ ID NO 39
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 39
tgcctctagc acgcgtgcgg ccgcttattg ctgtgctgcg gac                43

<210> SEQ ID NO 40
<211> LENGTH: 37
<212> TYPE: DNA

<213> ORGANISM: Artificial Sequence
<220> FEATURE:
<223> OTHER INFORMATION: Synthetic oligonucleotide

<400> SEQUENCE: 40
agcacgcgtg cggccgccat gattagccgt agcgaaa                37

<210> SEQ ID NO 41
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 41
cccaagcttc gaattcttaa ttcaaccgtt caatcac                37

<210> SEQ ID NO 42
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 42
gttcgggccc aagctttaag ccgttttcag gtcgc                  35

<210> SEQ ID NO 43
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 43
gttcgggccc aagcttgcgg ccgccggact tagcggtatt gctt        44

<210> SEQ ID NO 44
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 44
gttcgggccc aagcttgcgg ccgctgcaga ttatttgttc tgatagtctt t    51

<210> SEQ ID NO 45
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 45
gttcgggccc aagcttgcgg ccgcttattg ctgtgctgcg gac         43

<210> SEQ ID NO 46
<211> LENGTH: 44
<212> TYPE: DNA

```
<213> ORGANISM: Artificial Sequence
<220> FEATURE:
<223> OTHER INFORMATION: Synthetic oligonucleotide

<400> SEQUENCE: 46
gttcgggccc aagcttgcgg ccgccattta cgcggcttca actt                    44
```

FUNCTIONALIZED CARBOXYLIC ACIDS AND ALCOHOLS BY REVERSE FATTY ACID OXIDATION IN ENGINEERED MICROBES

PRIOR RELATED APPLICATIONS

This application is a continuation of PCT/US2012/054230, filed Sep. 7, 2012, and claims priority to U.S. Ser. No. 61/531,911, filed Sep. 7, 2011. This application claims priority for US purposes only to U.S. Ser. No. 61/440,192, filed Feb. 7, 2011. All of these applications are incorporated by reference in their entirety.

FEDERALLY SPONSORED RESEARCH STATEMENT

This invention was made with government support under CBET-1134541 awarded by the National Science Foundation. The government has certain rights in the invention.

FIELD OF THE INVENTION

The invention relates to engineered microorganisms that can make various chemicals for industrial use. In particular, the fatty acid oxidation pathway is driven in reverse, converting fatty acids to feedstock and specialty chemicals having fewer carbons.

BACKGROUND OF THE INVENTION

We have already demonstrated that the engineered reversal of the β-oxidation cycle can be used to generate straight-chain aliphatic carboxylic acids and n-alcohols with side chains of different lengths and functionalities (61/440,192 and PCT/US12/24051, filed Feb. 7, 2012 and both incorporated by reference herein in their entireties). In all cases the synthesized molecules were primary n-alcohols or carboxylic acids with a methyl group at the omega end. The present invention continues the research developed in the reverse β-oxidation application, and allows further diversification of products.

To summarize the prior ground breaking work, the methodology used to drive the reversed β-oxidation cycle involved the following three steps: 1) functionally expressing the β-oxidation cycle enzymes in the absence of its naturally inducing substrates (i.e. absence of fatty acids) and presence of a non-fatty acid carbon source (e.g. presence of glucose); 2) driving the β-oxidation cycle in the reverse/biosynthetic direction (as opposed to its natural catabolic/degradative direction); and 3) expressing termination enzymes that act on the appropriate intermediate of the β-oxidation cycle to make desired products.

In more detail, the recombinant engineering was:

1) Express the β-Oxidation Cycle in the Absence of its Naturally Inducing Substrates (i.e. Absence of Fatty Acids) and Presence of a Non-Fatty Acid Carbon Source (e.g. Presence of Glucose):

In order to express the β-oxidation cycle, i) mutations fadR and atoC(c) enabled the expression of the genes encoding beta oxidation enzymes in the absence of fatty acids; ii) an arcA knockout (ΔarcA) enabled the expression of genes encoding beta oxidation cycle enzymes/proteins under anaerobic/microaerobic conditions (microaerobic/anaerobic conditions are used in the production of fuels and chemicals but lead to repression of beta oxidation genes by ArcA); and iii) replacement of native cyclic AMP receptor protein (crp) with a cAMP-independent mutant (crp*) enabled the expression of genes encoding beta oxidation cycle enzymes/proteins in the presence of a catabolite-repressing carbon source such as glucose (glucose is the most widely used carbon source in fermentation processes and represses the beta oxidation genes).

2) Driving the Beta Oxidation Cycle in the Reverse/Biosynthetic Direction (as Opposed to its Natural Catabolic/Degradative Direction).

In addition to functionally expressing the β-oxidation cycle, reverse operation of this pathway was accomplished by driving acetyl-CoA and its precursors towards the beta oxidation cycle and preventing A-coA use elsewhere. Specifically, iv) the use of microaerobic/anaerobic conditions minimized the metabolism of acetyl-CoA through the TCA cycle and made acetyl-CoA available to drive the beta oxidation cycle in the reverse/biosynthetic direction; v) pta (or ackA or both), poxB, adhE, yqhD, and eutE knockouts reduced the synthesis of acetate (Δpta or ΔackA and poxB) and ethanol (ΔadhE, ΔyqhD, and ΔeutE) from acetyl-CoA and therefore make acetyl-CoA available to drive the beta oxidation cycle in the reverse/biosynthetic direction; vi) overexpression of thiolases, the first step in the reversal of the beta oxidation cycle, enabled the channeling of acetyl-CoA into this pathway and hence its operation in the reverse direction; vii) ldhA, mgsA, and frdA knockouts reduced the synthesis of lactate (ΔldhA and ΔmgsA) and succinate (ΔfrdA) from pyruvate and phosphoenolpyruvate, respectively, making more phosphoenolpyruvate and pyruvate available for the synthesis acetyl-CoA and therefore making acetyl-CoA available to drive the beta oxidation cycle in the reverse/biosynthetic direction; viii) overexpression of pyruvate:flavodoxin oxidoreductase (ydbK) and acyl-CoA dehydrogenase (ydiO and ydiQRST) enables the coupling of pyruvate oxidation (pyruvate→acetyl-CoA+$CO_2$+$Fd_{red}$) and trans-$\Delta^2$-enoyl-CoA reduction (trans-$\Delta^2$-enoyl-CoA+$Fd_{red}$→acyl-CoA) and hence drive the beta oxidation in the reverse direction.

3) Conversion of CoA Thioester Intermediates to the Desired End Products.

Several termination enzymes that pull reaction intermediates out of the reverse β-oxidation cycle and produce the desired end product were described:

i) CoA thioester hydrolases/thioesterases, or acyl-CoA: acetyl-CoA transferases, or phosphotransacylases and carboxylate kinases for carboxylic acids (i.e. short, medium, and long-chain monocarboxylic acids, β-keto acids, β-hydroxy acids, trans-$\Delta^2$-fatty acids), ii) alcohol-forming CoA thioester reductases for alcohols (i.e. short, medium, and long-chain n-alcohols, β-keto alcohols, 1,3-diols, trans-$\Delta^2$-alcohols), iii) aldehyde-forming CoA thioester reductases and alcohol dehydrogenases which together form alcohols (i.e. short, medium, and long-chain n-alcohols, β-keto alcohols, 1,3-diols, trans-$\Delta^2$-alcohols), iv) aldehyde-forming CoA thioester reductases and aldehyde decarbonylases (which together form alkanes or terminal alkenes of different chain lengths), and v) olefin-forming enzymes (which together form aliphatic internal alkenes or terminal alkenes or trienes or alkenols).

One or more of these termination enzymes can be overexpressed, as needed depending on the desired end product.

4. Regulation of Product Chain Length.

The chain length of thioester intermediates determines the length of end products, and was controlled by using appropriate termination enzymes with the desired chain-length specificity. Additionally, chain elongation can be inhibited or promoted by reducing or increasing the activity of thiolases with the desired chain-length specificity. These two methods can be used together or independently. For example:

i) knockout of fadA, fadI, and paaJ to avoid chain elongation beyond 1-to-2 turns of the cycle (generates 4- & 6-carbon intermediates and products, or 5- & 7-carbon intermediates and products, depending on the use of acetyl-CoA or propionyl-CoA as primer/starter molecule) and overexpression of the short-chain thiolases yqeF or atoB or short chains alcohol dehydrogenases such as fucO or yqhD;

ii) overexpression of fadB, fadI, and paaJ to promote chain elongation and overexpression of long-chain thiolases tesA, tesB, fadM, ybgC or yciA or long chain alcohol dehydrogenases such as ucpA, ybbO, yiaY, betA, ybdH or eutG.

The term "appropriate" is used herein to refer to an enzyme with the required specificity toward a given intermediate (i.e. acyl-CoA, enoyl-CoA, hydroxyacyl-CoA, and ketoacyl-CoA) of a specific chain length. Please note that the chain length of the thioester intermediates can be controlled by manipulating thiolases (as described above), and hence only thioesters of the desired chain length will be available to the termination enzymes.

We have now modified the above work to make a better platform, which also allows the initiating chemical to include many more primers than just acetyl-coA or propionyl co-A, as well as using an appropriate termination enzyme at step 3 to produce many more additional chemicals.

SUMMARY OF THE INVENTION

The initial reverse beta oxidation work employed acetyl-CoA (for even length products) and propionyl-CoA (for odd chain length products) as primers and corresponding termination pathways that then lead to the synthesis of carboxylic acids and alcohols as products.

By contrast, the current invention uses e.g., one of 14 primers, none of them being acetyl-CoA or propionyl-CoA (although acetyl-coA does condense with the primer, acting as extender unit, to add two carbon units thereto). These, in combination with different termination pathways, lead to the synthesis of diols, dicarboxylic acids, hydroxy acids, carboxylated alcohols, amines, amino acids, hydroxylated amines, diamines, amides, carboxylated amides, hydroxylated amides, diamides, hydroxamic acids and their β-substituted derivatives thereof.

In one embodiment, the invention is a genetically engineered bacteria comprising:
a. an overexpressed thiolase;
b. an overexpressed 3-hydroxyacyl-CoA dehydrogenase;
c. an overexpressed enoyl-CoA hydratase or 3-hydroxyacyl-CoA dehydratase;
d. an overexpressed acyl-CoA dehydrogenase or trans-enoyl-CoA reductase;
e. an overexpressed termination enzyme selected from the group consisting of:
  i. a thioesterase, or an acyl-CoA:acetyl-CoA transferase, or a phosphotransacylase and a carboxylate kinase, or
  ii. an alcohol-forming coenzyme-A thioester reductase, or
  iii. an aldehyde-forming CoA thioester reductase and an alcohol dehydrogenase, or
  iv. an aldehyde-forming CoA thioester reductase and an aldehyde decarbonylase, or
  v. an olefin-forming enzyme, or
  vi. an aldehyde-forming CoA thioester reductase and a transaminase; and f. reduced expression of fermentation enzymes leading to reduced production of lactate, acetate, ethanol and succinate;
wherein said bacteria have a reverse beta oxidation pathway running in an anabolic direction.

In the termination enzymes, the alcohol-forming coenzyme-A (CoA) thioester reductase includes but not limited to adhE2;
the aldehyde-forming CoA thioester reductase and alcohol dehydrogenase include but not limited to *Acinetobacter calcoaceticus* acrM, *Acinetobacter* sp. Strain M-13 acrI, *Clostridium kluyveri* sucD, *E. coli* ybbO, ucpA, mhpF and eutE, *Clostridium beijerinckii* ald, *Salmonella typhimurium* eutE for the aldehyde-forming CoA thioester reductases and *E. coli* fucO, betA, eutG, yiaY for the alcohol dehydrogenase;
the aldehyde-forming CoA thioester reductase and aldehyde decarbonylase includes but not limited to aldehyde-forming CoA thioester reductase same as above and PCC7942_orf1593 from *Synechococcus elongatus* PCC7942 and PMT9312_0532 from *Prochlorococcus marinus* MIT9313 for the aldehyde decarbonylase;
the olefin-forming enzyme includes but not limited to oleA, oleB, oleC, and oleD from *Xanthomonas campestris*; and
the aldehyde-forming CoA thioester reductase and transaminase includes but not limited to aldehyde-forming CoA thioester reductase same as above and gabT from *E. coli* and *Pseudomonas fluorescens*, abat from *Mus musculus* and *Sus scrofa*, and SGR_1829 from *Streptomyces griseus* for the transaminases.

In another embodiment, the invention is an engineered bacteria, comprising a reverse beta oxidation cycle, said microorganism comprising:
a. a pathway for the synthesis of CoA thioesters that can act as primer units of a reverse beta-oxidation cycle;
b. overexpressed enzymes that enable the synthesis of intermediates in the beta-oxidation reversal including i) a thiolase, ii) a 3-hydroxyacyl-CoA dehydrogenase, iii) an enoyl-CoA hydratase or a 3-hydroxyacyl-CoA dehydratase, and iv) an acyl-CoA dehydrogenase or a trans-enoyl-CoA reductase;
c. one or more overexpressed termination enzymes that convert a reverse beta oxidation cycle intermediate to a desired product.

Preferably, the native fermentation pathways in said organism have been reduced and less acetate, lactate, ethanol and succinate are thereby produced.

Another embodiment of the invention, is an engineered *Escherichia* cell, comprising:
a. ΔadhE, (Δpta or ΔackA or ΔackApta), ΔpoxB, ΔldhA, and ΔfrdA,
b. plus one overexpression of i) a thiolase; ii) a 3-hydroxyacyl-CoA dehydrogenase; iii) an enoyl-CoA hydratase or a 3-hydroxyacyl-CoA dehydratase; and iv) an acyl-CoA dehydrogenase or a trans-enoyl-CoA reductase; wherein enzymes i-iv) together create a reverse beta oxidation anabolic cycle; and
c. an expression vector providing an overexpressed termination enzyme that converts a reverse beta oxidation cycle intermediate to a desired product.

As used herein, overexpression of a gene/protein/enzyme can be achieved by known methods in the field, for example by using a controllable expression vector or by overexpression of the gene in the chromosome or other methods.

Other embodiments are methods of making a desired product, comprising growing a genetically engineered bacteria as described herein in a culture broth, extending an acetyl-coA charged primer by using a reverse beta oxidation pathway to produce a product at least two carbons longer than said primer, and isolating said product, wherein the primer is selected from those listed in Table 3A-B. Both, the primer and products can selected from those listed in Table 3A-B, and preferably primer, products and bacteria genotypes are all selected from those listed in Table 3A-B.

By "primer" what is meant is an initiator or starter molecule that is or becomes charged with CoA, and then condenses with another acetyl-coA in the reverse beta oxidation cycle, thus making the primer longer by two carbons. Such molecules include: i) oxalyl-CoA, malonyl-CoA, succinyl-CoA, ii) hydroxyacetyl-CoA, 3-hydroxypropionyl-CoA, 4-hydroxybutyryl-CoA, iii) 2-aminoacetyl-CoA, 3-aminopropionoyl-CoA, 4-aminobutyryl-CoA, and iv) isobutyryl-CoA, 3-methyl-butyryl-CoA, 2-hydroxypropionyl-CoA, 3-hydroxybutyryl-CoA, 2-aminopropionyl-CoA. Such primers can be provided to the cell or precursors therefor can be provided, or the cell can be engineered to produce same as shown in FIGS. 3-5.

By "reverse beta oxidation cycle" or "RBOx cycle" what is meant is the normal catabolic fatty acid oxidation cycle is driven in reverse, or anabolic direction, thus making intermediates longer by two carbons per cycle. The normal beta oxidation cycle reactions proceed as shown in FIG. 15, and generally includes i) dehydrogenation to make a double bond, ii) hydration to convert the double bond to —OH, iii) dehydrogenation to convert the —OH to a carbonyl group, and iv) loss of two carbons as acetyl-coA. The reverse beta oxidation cycle instead includes i) condensation of two carbon as acetyl-coA to primer, ii) hydrogenation of carbonyl to —OH, iii) loss of water to form double bond, and iv) hydrogenation to remove the double bond. See e.g., FIG. 8.

By "termination enzyme" what is meant herein are enzymes that catalyze a reaction taking reverse beta oxidation intermediates out of the RBOx cycle, thus "terminating" the running of the cycle. Termination enzymes include, but are not limited to i) thioesterases, or acyl-CoA:acetyl-CoA transferases, or phosphotransacylases and carboxylate kinases (which form carboxylic acids) or ii) alcohol-forming coenzyme-A thioester reductases (which make alcohols) or iii) aldehyde-forming CoA thioester reductases and alcohol dehydrogenases (which together form alcohols) or iv) aldehyde-forming CoA thioester reductases and aldehyde decarbonylases (which together form alkanes or terminal alkenes) or v) olefin-forming enzymes (such as OleA, OleB, OleC, OleD, which together form internal alkenes or terminal alkenes or trienes or alkenols).

Exemplary gene/protein/species are provided herein. However, gene, protein and enzyme nomenclature varies widely, thus any protein that catalyzes the same reaction can be substituted herein. Further, while exemplary protein sequence accession numbers are provided herein, each is linked to the corresponding DNA sequence, and to related sequences. Further, related sequence can be identified easily by homology search and requisite activities confirmed as shown herein.

*E. coli* gene and protein names (where they have been assigned) can be ascertained through ecoliwiki.net/ and enzymes can be searched through brenda-enzymes.info/. Many similar databases are available including PROSITE; EC2PDB; ExplorEnz; PRIAM; KEGG Ligand; IUBMB Enzyme Nomenclature; IntEnz; MEDLINE; and MetaCyc, to name a few.

By convention, genes are written in italic, and corresponding proteins in regular font. E.g., ackA is the gene encoding AckA or acetate kinase A.

As used herein + refers to an overexpressed enzymatic activity, meaning at least 150% wild type activity, and preferably 200, 500, 1000% or more. Overexpressed activity can be achieved by upregulating the endogenous gene, removing repressors, adding in a gene encoding an enzyme with higher Km, or preferably by adding in a gene under a controllable promoter.

The symbol delta Δ means the activity is not detectable or insignificant. Gene activity can be made non-detectable by use of stop mutations, deletions, frameshifts and the like.

Reference to "activity" herein means reference to the enzymatic activity of a protein, or a gene encoding that protein.

Reduced activity means at least 75% reduction in enzymatic activity levels, as compared with the wild type at that locus.

The invention generally relates to the functionalization of the alpha and omega (ω) carbons of products produced by reverse beta oxidation by introducing carboxylic and/or alcohol groups. This, in turn, would generate omega-hydroxylated carboxylic acids, omega-carboxylated n-alcohols, dicarboxylic acids, diols, and the following alpha-hydroxylated derivatives: alpha-hydroxylated and omega-carboxylated n-alcohols, alpha-hydroxylated dicarboxylic acids, and 1,2,n-triols.

In all cases, products of different chain lengths can be obtained: i.e. products with an internal/spacer chain between the alpha and omega ends of different lengths, depending on the number of turns of the cycle, and containing different functionalities, depending on the β-oxidation intermediate used as precursor for their synthesis. The latter includes a hydroxy or keto group in the beta carbon and an α,β unsaturation.

Two general approaches are used in the invention to functionalize the alpha and omega carbons:
i) use of a primer or starter with a functionalized omega carbon, along with the appropriate set of β-oxidation and termination enzymes able to act upon ω-functionalized thioesters intermediates and
i) functionalizing the alpha/omega carbon of an intermediate or a product of the engineered reversal of the β-oxidation cycle. The latter could take place before or after the intermediates of the engineered reversal of the β-oxidation cycle have been converted to carboxylic acids and n-alcohols by the appropriate termination enzymes. Enzymes functioning in the required alpha/omega-functionalizing pathway should be expressed, along with the required β-oxidation and termination enzymes.

A list of potential primers and products (along with exemplary genotypes) is provided as Tables 3A-B, and additional possibilities are provided in Tables 4A-E.

NADPH→glycolate+NADP) [EC: 1.1.1.79]; (16) malate: NAD/NADP dehydrogenase [EC:1.1.1.37/EC:1.1.1.299]; (17) FADH2-/NADH/ubiquinol/menaquinol-dependent fumarate reductase [EC:1.3.99.1/EC:1.3.1.6/EC:1.3.1.5/EC: 1.3.1.4]; (18) succinyl-CoA synthetase/ligase (ATP+Succinate+CoA<=>ADP+Orthophosphate+Succinyl-CoA) [EC: 6.2.1.5], succinyl-CoA: acetoacetate CoA-transferase (Succinyl-CoA+Acetoacetate<=>Succinate+Acetoacetyl-CoA) [EC: 2.8.3.5]; (19) succinate-semialdehyde:NADP+ oxidoreductase (Succinyl-CoA+NADPH+H+<=>Succinate semialdehyde+NADP++CoA) [EC: 1.2.1.76]; (20) 4-Hydroxybutanoate:NAD+oxidoreductase (4-Hydroxybutanoic acid+NAD+<=>Succinate semialdehyde+NADH+H+) [EC: 1.1.1.61] or succinate semialdehyde reductase (NADPH) (4-Hydroxybutanoic acid+NADP+<=>Succinate semialdehyde+H++NADPH) [EC:1.1.1.-]; (21) 4-hydroxybutyrate: CoA ligase (AMP-forming) (4-Hydroxybutanoic acid+ATP+CoA<=>4-Hydroxybutyryl-CoA+AMP+Diphosphate) [EC: 6.2.1.-] or acetyl-CoA: 4-hydroxybutanoate CoA transferase (4-Hydroxybutanoic acid+Acetyl-CoA<=>4-Hydroxybutyryl-CoA+Acetate) [EC: 2.8.3.-]. The omega-hydroxylated keto-acyl-CoAs resulting from the condensation of hydroxyacetyl-CoA and 4-hydroxybutyryl-CoA with acetyl-CoA undergo reduction and dehydration steps in the β-oxidation reversal to generate the omega-hydroxylated intermediates, which in turn support the synthesis of omega-hydroxylated n-alcohols and carboxylic acids.

Figure 5:
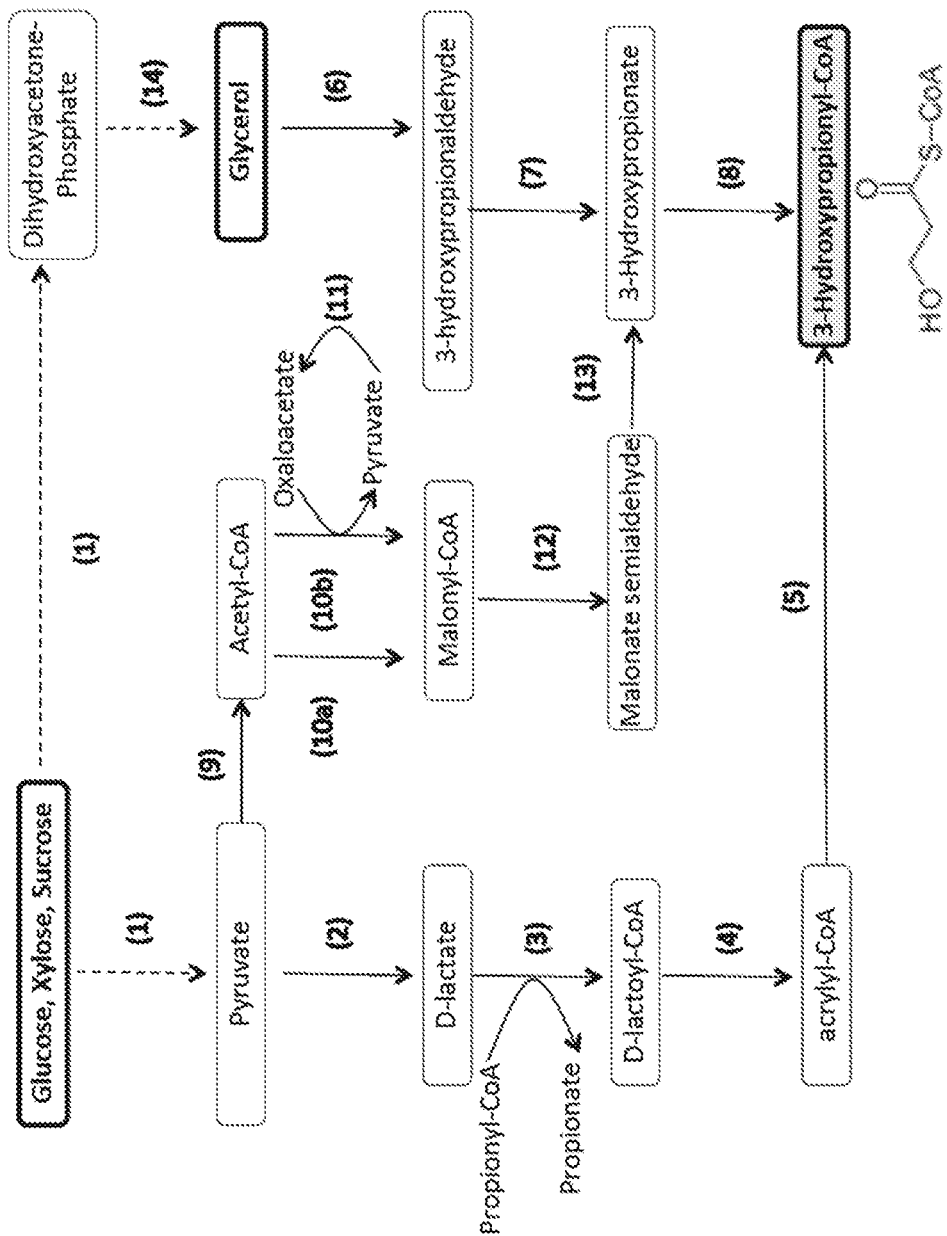

FIG. 5. Synthesis of omega-hydroxylated acyl-CoAs from 3-hydroxypropionyl-CoA primer. Numbers indicate enzymes catalyzing the indicated conversions. (1) enzymes catalyzing carbon-utilization and glycolytic pathways; (2) D-lactate dehydrogenase [EC:1.1.1.28]; (3) lactoyl-CoA: propanoate CoA-transferase (Lactoyl-CoA+Propanoate<=>(S)-Lactate+Propanoyl-CoA) [EC:2.8.3.1] or propionate CoA-transferase (Lactoyl-CoA+Acetate<=>(S)-Lactate+Acetyl-CoA) [EC:2.8.3.1]; (4) Lactoyl-CoA hydro-lyase (Lactoyl-CoA<=>Propenoyl-CoA+H2O) [EC:4.2.1.54]; (5) 3-Hydroxypropionyl-CoA hydro-lyase (3-Hydroxypropionyl-CoA<=>Propenoyl-CoA+H2O) [EC:4.2.1.116]; (6) glycerol dehydratase (Glycerol→3-hydroxypropionaldehyde+H2O) [EC:4.2.0.30]; (7) γ-glutamyl-γ-aminobutyraldehyde dehydrogenase β-hydroxypropionaldehyde+NAD++H2O→3-hydroxypropionate+2H+) [EC:1.2.1.-]; (8) 3-hydroxypropionate:CoA ligase (AMP-forming) (3-Hydroxypropionyl-CoA+Diphosphate+AMP<=>3-Hydroxypropanoate+CoA+ATP) [EC: 6.2.1.36]; (9) pyruvate dehydrogenase complex [EC: 1.2.4.1], pyruvate formate-lyase [EC:2.3.1.54], pyruvate:flavodoxin/:ferredoxin oxidoreductase [EC: 1.2.7.1]; (10a) Acetyl-CoA:carbon-dioxide ligase (ATP+Acetyl-CoA+HCO3-<=>ADP+Orthophosphate+Malonyl-CoA) [EC:6.4.1.2]; (10b) Malonyl-CoA:pyruvate carboxytransferase (Malonyl-CoA+Pyruvate<=>Acetyl-CoA+Oxaloacetate) [EC:2.1.3.1]; (11) malic enzyme [EC: 1.1.1.40/EC:1.1.1.38] and malate dehydrogenase ((S)-Malate+NAD+/NADP+<=>Oxaloacetate+NADH/NADPH+H+) [EC:1.1.1.37/EC:1.1.1.82]; (12) malonyl CoA reductase (malonate semialdehyde-forming) (CoA-malonylating) (malonate semialdehyde+coenzyme A+NADP+=malonyl-CoA+NADPH+H+) [EC:1.2.1.75]; (13) 3-hydroxypropionate:NADP+ oxidoreductase (3-Hydroxypropanoate+NAD+/NADP+<=>3-Oxopropanoate+NADH/NADPH+H+) [EC:1.1.1.59/EC:1.1.1.298]; (14) Glycerol-3-phosphate dehydrogenase [EC:1.1.1.8/1.1.1.94] and glycerol-3-phosphatase [EC:3.1.3.21] (Two-steps with glycerol-3-phosphate intermediate). The 5-hydroxy 3-oxo-pentanoyl-CoA resulting from the condensation of 3-hydroxypropionyl-CoA with acetyl-CoA undergoes reduction and dehydration steps in the β-oxidation reversal to generate odd-chain omega-hydroxylated intermediates, which in turn support the synthesis of odd-chain omega-hydroxylated n-alcohols and carboxylic acids.

Figure 6:
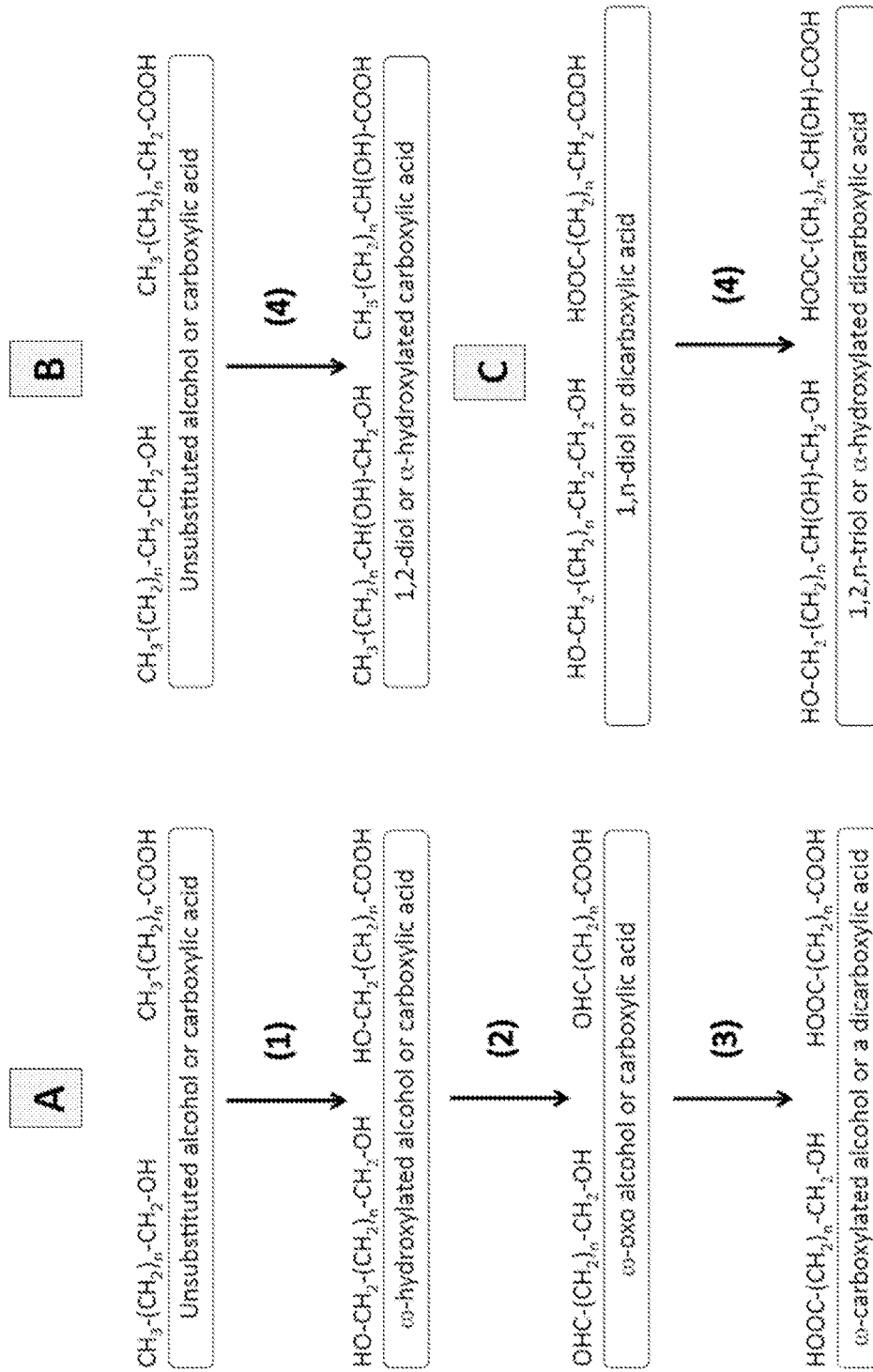

FIG. 6A-C. Alpha- and omega-functionalization of carboxylic acids and alcohols obtained from the beta-oxidation reversal using the omega oxidation (A) and alpha oxidation (B and C) pathways. Numbers indicate enzymes catalyzing the indicated conversions. (1) Fatty acid, reduced rubredoxin:oxygen oxidoreductase (omega-hydroxylating) (Fatty acid+Oxygen+Reduced rubredoxin<=>omega-Hydroxy fatty acid+Oxidized rubredoxin+H2O) [EC: 1.14.15.3] or Omega-hydroxylase/Alkane, reduced-rubredoxin:oxygen 1-oxidoreductase (Alkane+Reduced rubredoxin+Oxygen<=>Oxidized rubredoxin+Primary alcohol+H2O) [EC: 1.14.15.3]; (2) primary alcohol:NAD+oxidoreductase (Primary alcohol+NAD+/NADP+/O2/Acceptor<=>Aldehyde+NADH/NADPH/H2O2/Reduced Acceptor+H+) [EC:1.1.1.1/EC:1.1.1.71/EC:1.1.3.13/EC: 1.1.99.20]; (3) aldehyde:(pyrroloquinoline-quinone) oxidoreductase (an aldehyde+acceptor/NAD+/NADP++H2O=a carboxylate+reduced acceptor/NADH/NADPH) [EC:1.2.99.3/6/7/EC:1.2.1.3//EC:1.2.1.5]; (4) Fatty acid, reduced-flaboprotein:oxygen oxidoreductase (RH-hydroxylating or -epoxidizing) (Reduced flavoprotein+Fatty acid+Oxygen<=>alpha-Hydroxy fatty acid+Oxidized flavoprotein+H2O) [EC:1.14.14.1].

Figure 7:
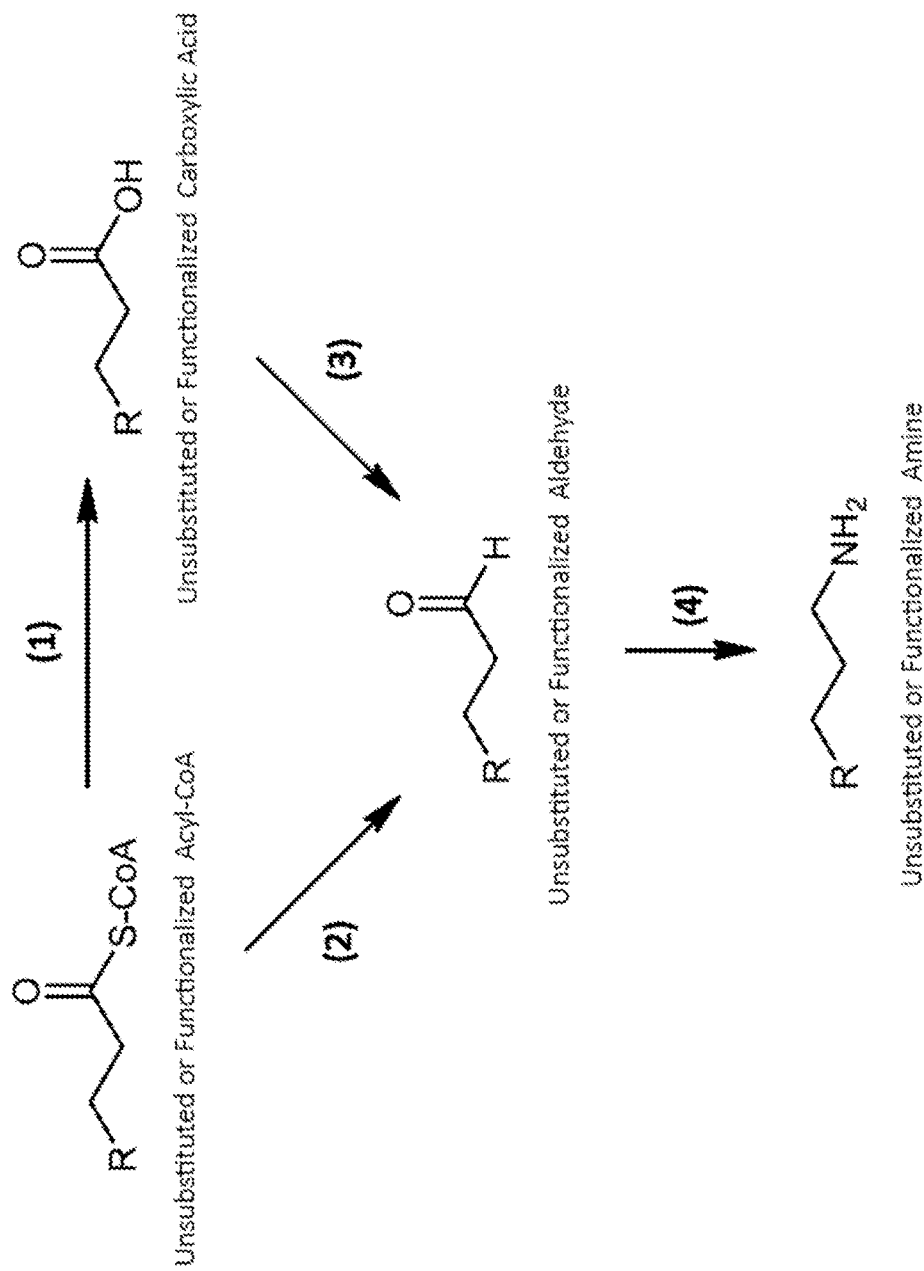

FIG. 7. Amine-functionalization of acyl-CoA intermediates and carboxylic acids obtained from the beta-oxidation reversal. "R" groups represent both additional carbon length and functionalized groups obtained from the β-oxidation reversal. Numbers indicate enzymes catalyzing the indicated conversions. (1) thioesterases [EC: 3.1.2.-] such as *E. coli* TesA, TesB, YciA, FadM, YdiI, YbgC, PaaI, and YbdB; (2) CoA-dependent aldehyde dehydrogenase [EC: 1.2.1.-] such as the fatty acyl-CoA reductases from *Acinetobacter calcoaceticus* (Reiser and Somerville, 1997, J. Bacteriol. 179: 2969-2975), and *Acinetobacter* sp. Strain M-1 (Ishige et al., 2002, Appl. Environ, Microbiol. 68:1192-1195), and the sucD gene from *Clostridium kluyveri* (Sohling and Gottschalk, 1996, J. Bacteriol. 178:871-880); (3) carboxylic acid reductase (CAR)/aldehyde dehydrogenase [EC: 1.2.99.6/7] or aldehyde oxidoreductase [EC: 1.2.7.5] such as the CAR from *Nocardia* sp. NRRL 5646 (Venkitasubramanian et al., 2008, Enzyme Microb. Technol. 42:130-137); and (4) transaminases [EC: 2.6.1-] such as gamma-aminobutyrate transaminase from *E. coli* (Bartsch et al., 1990, J. Bacteriol. 172:7035-7042), *Mus musculus* (Cooper, 1985, Methods Enzymol. 113, 80-82), *Pseudomonas fluorescens* (Scott and Jacoby, 1959, J. Biol. Chem. 234, 932-936), and *Streptomyces griseus* (Yonaha et al., 1985, *Eur. J. Biochem.* 146:101-106) or lysine-6-dehydrogenases [EC: 1.4.1.18] from organisms such as *Geobacillus stearothermophilus* (Heydari et al., 2004, Appl. Environ. Microbiol. 70, 937-942), *Agrobacterium tumefaciens* (Hashimoto et al., 1989, *Agric. Biol. Chem.* 53, 1175-1176), and *Achromobacter denitrificans* (Ruldeekulthamrong et al., 2008, *BMB Rep.* 41, 790-795).

Figure 8:
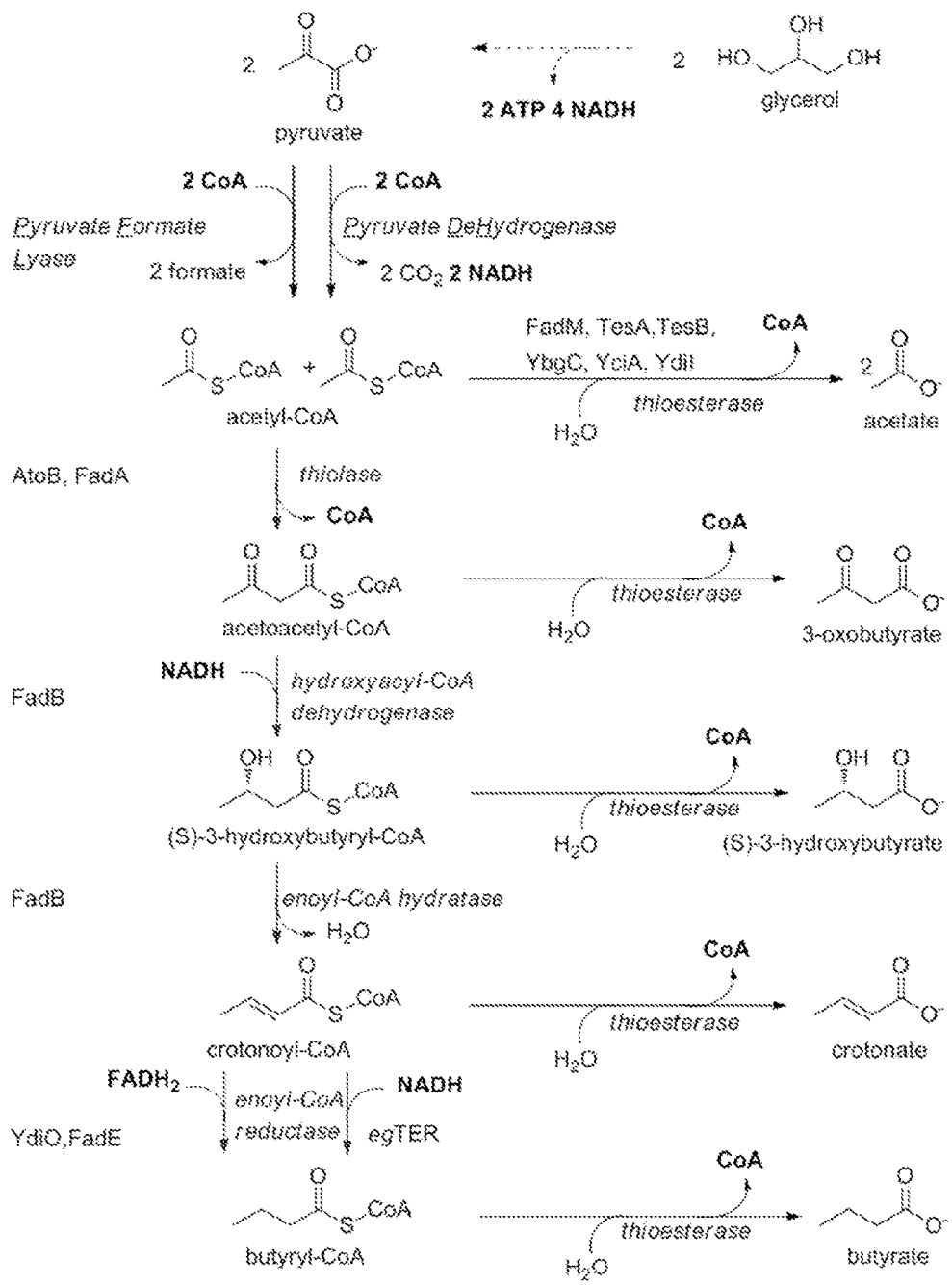

FIG. 8. Reverse Beta Oxidation Cycle: One-turn functional reversal of the β-oxidation cycle with 4-C carboxylic acids as a proxy for product synthesis. Core pathway enzymes are circled in broken line, with thioesterase termination pathways resulting in carboxylic acid formation from each cycle intermediate. A multiple turn cycle involves the condensation of the end acyl-CoA molecule (butyryl-CoA from a one-turn reversal) with acetyl-CoA resulting in a 2-carbon elongation.

Figure 9A:
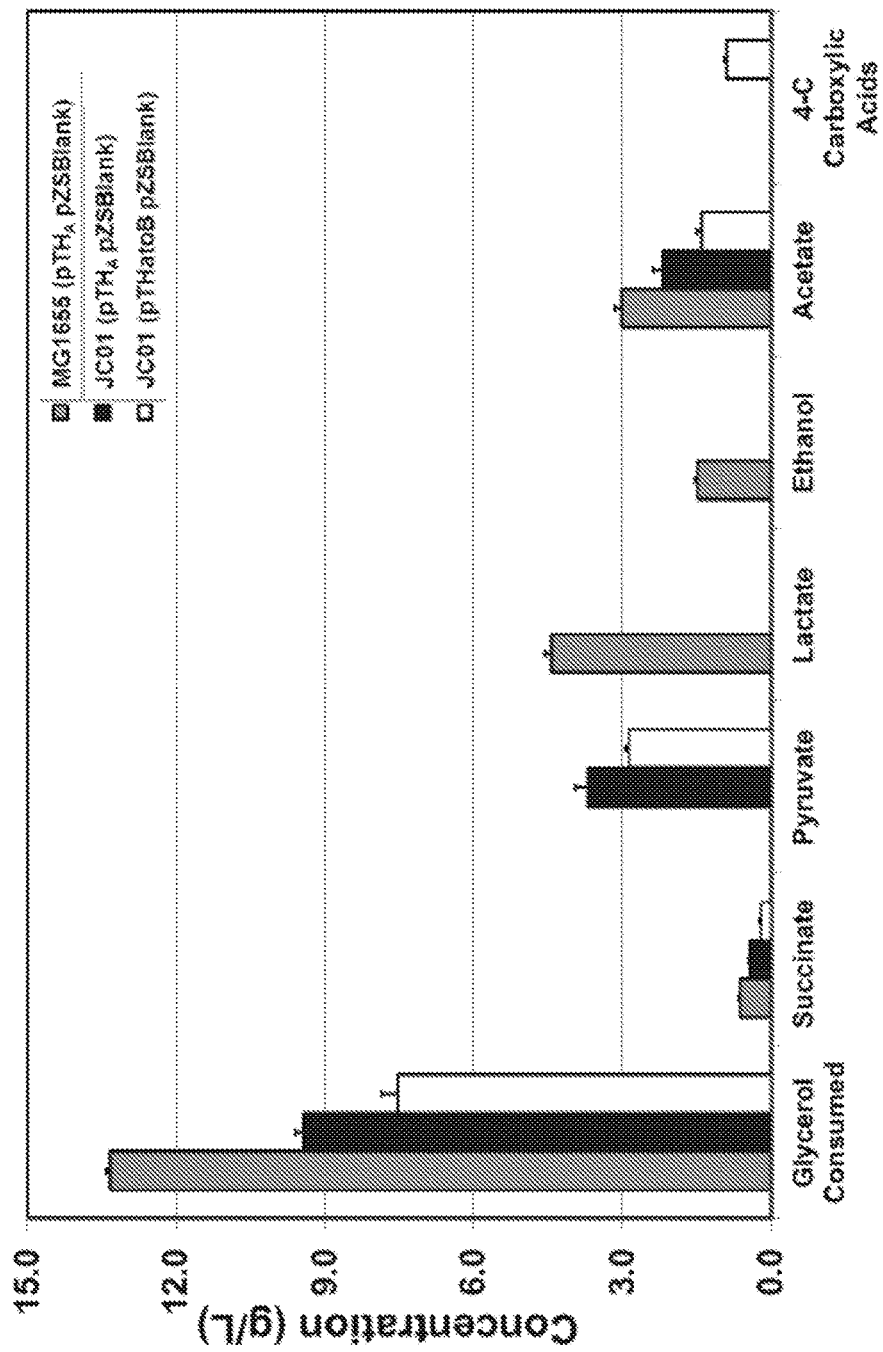
Figure 9B:
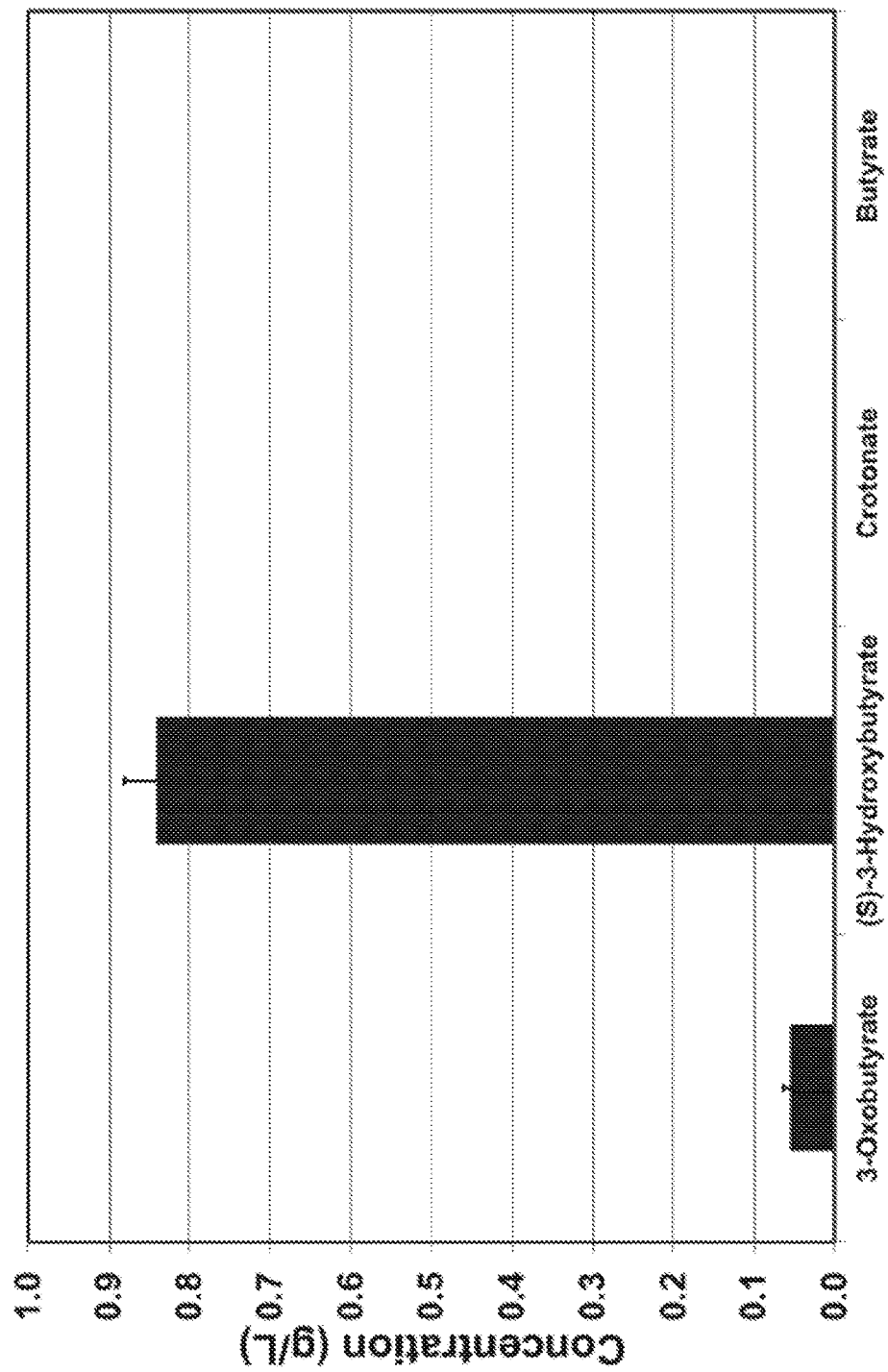

FIG. 9A-B. Re-programming host metabolism for the in vivo assembly of the individual components of a β-oxidation reversal. (A) Glycerol consumption and product synthesis in wild-type *E. coli* MG1655 and engineered strain JC01 (MG1655 ΔldhAΔpoxBΔptaΔadhEΔfrdA) with control vectors pTH$_4$ and pZSBlank, and JC01 with thiolase (AtoB) overexpression. (B) Distribution of 4-C carboxylic acids produced upon thiolase overexpression in JC01, i.e. JC01 (pTHatoB pZSBlank). Gene overexpression apparent from plasmid names (i.e. pTHatoB expressing atoB).

Figure 10A:
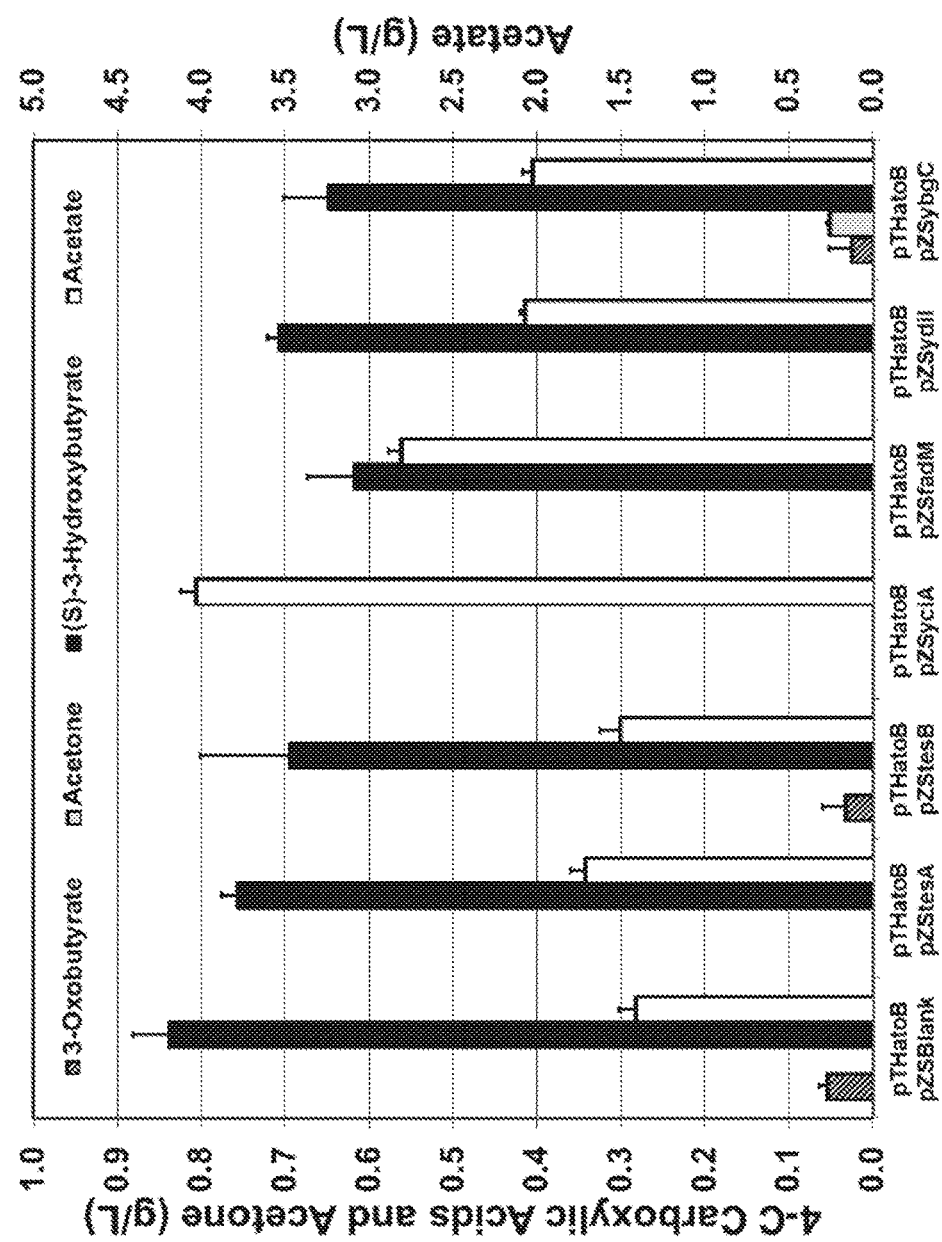
Figure 10B:
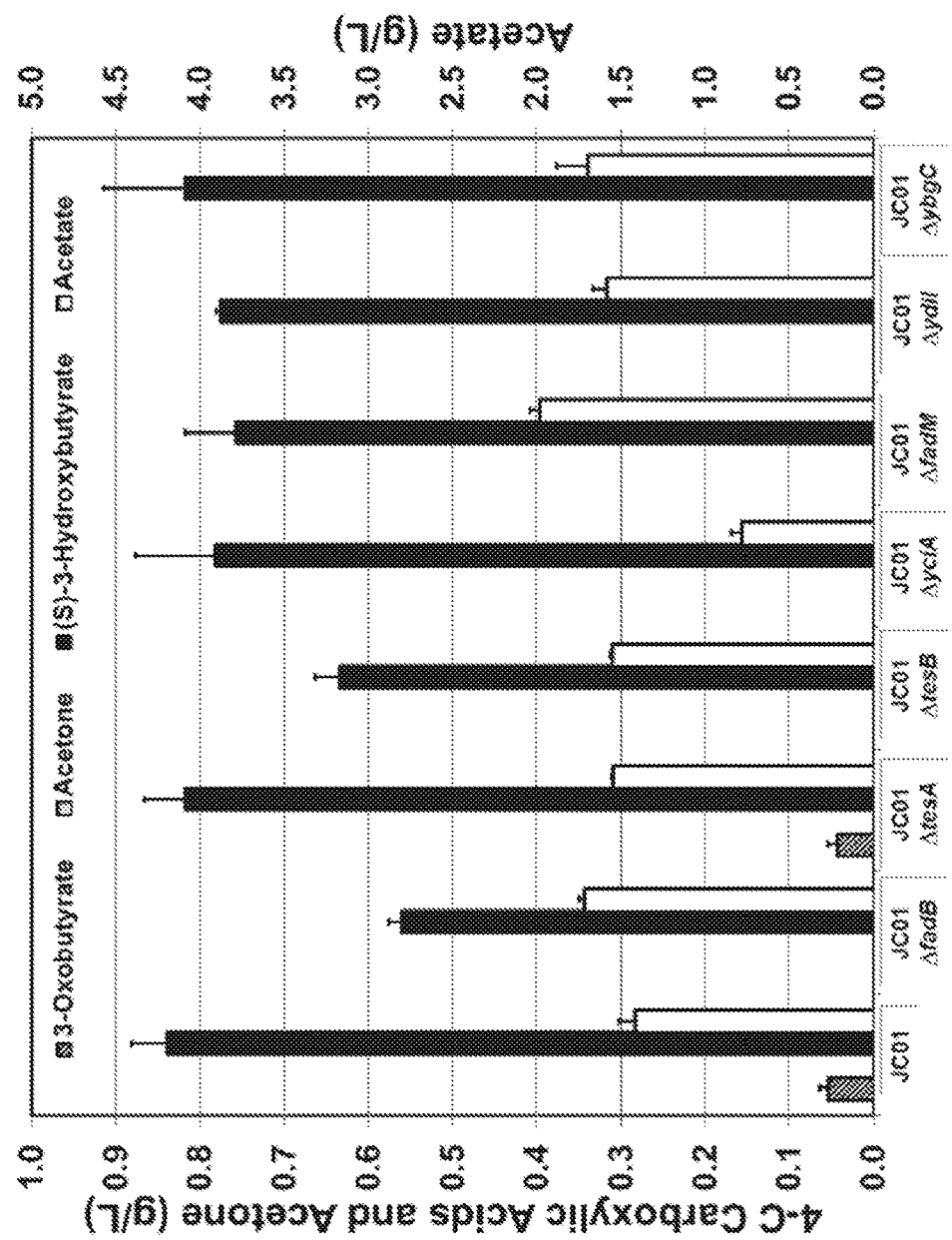

FIG. 10A-B. Impact of thiolase overexpression and termination pathway manipulation (A) 4-C carboxylic acid and acetone production in JC01 upon thiolase (AtoB) overexpression in combination with thioesterase overexpression (B) 4-C carboxylic acid and acetone production in JC01 harboring pTHatoB and pZSBlank with native 3-hydroxyacyl-CoA dehydrogenase (FadB) or thioesterase chromosomal deletion. Gene overexpression apparent from plasmid names (i.e. pZStesA expressing tesA). "Δgene" represents gene deletion.

Figure 11A:
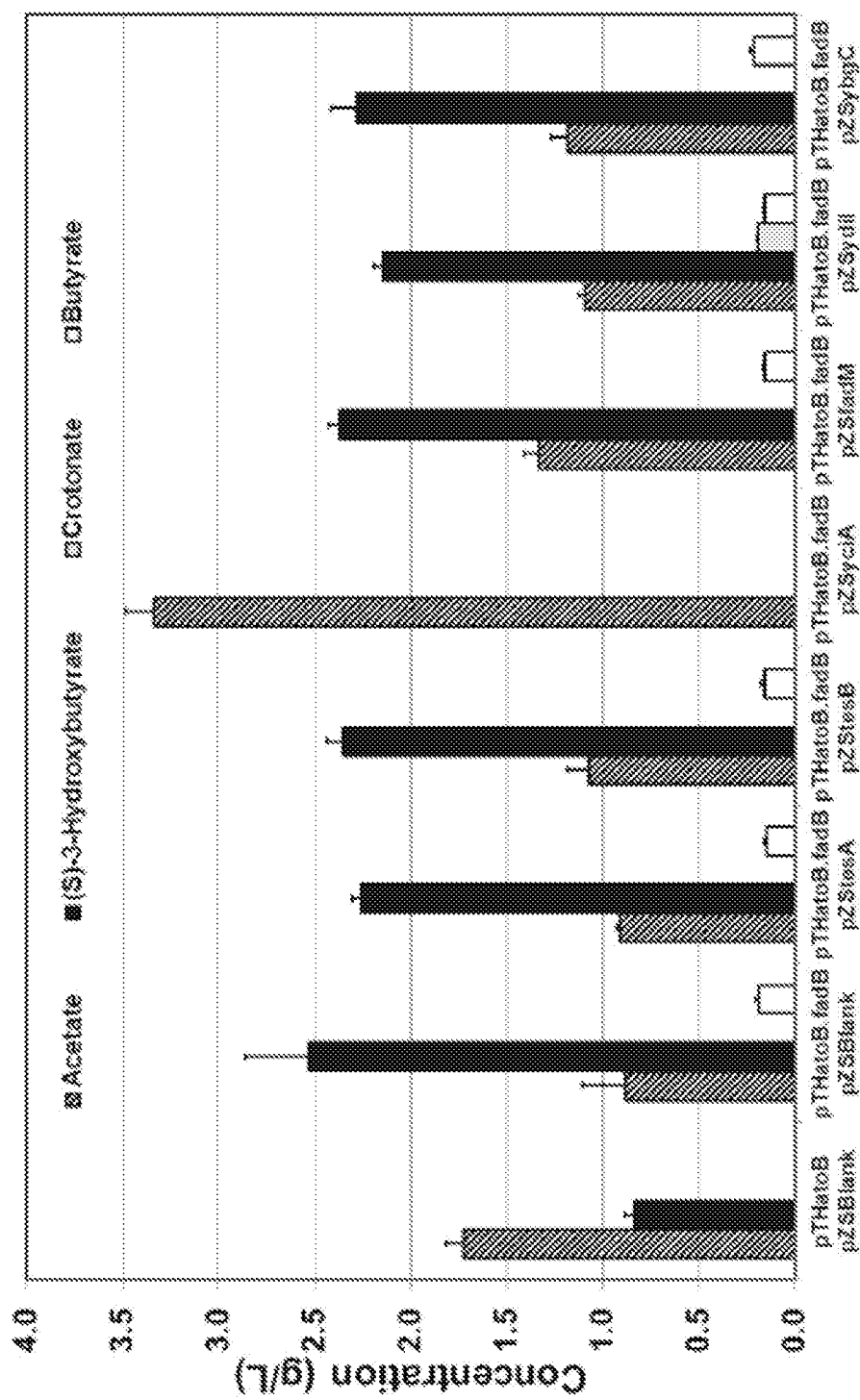
Figure 11B:
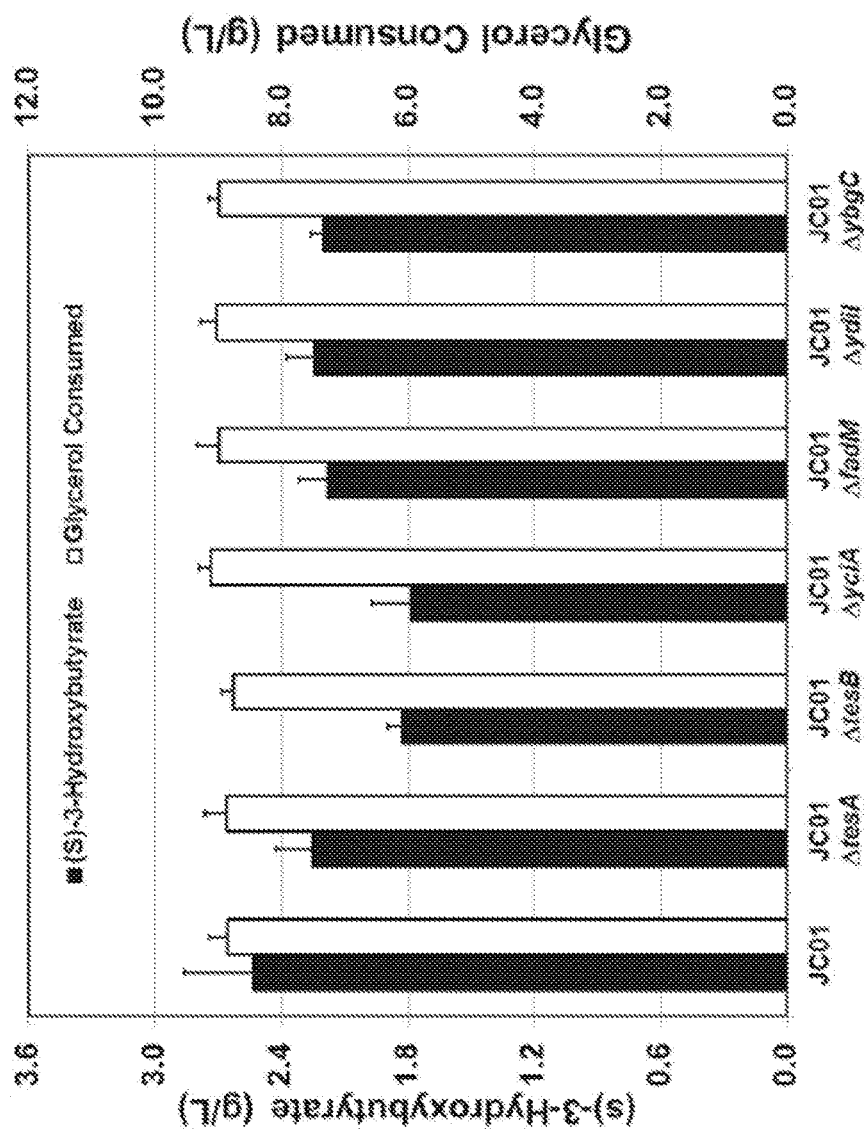

FIGS. 11A-B. In vivo assembly of the thiolase, 3-hydroxyacyl-CoA dehydrogenase, and enoyl-CoA hydratase components of a one-turn β-oxidation reversal. (A) 4-C carboxylic acid and acetate production in JC01 with AtoB and FadB expression in conjunction with thioesterase overexpression. (B) Impact of native thioesterase chromosomal deletion on 4-C carboxylic acid and acetone production in the host strain harboring pTHatoB.fadB and pZSBlank. Gene overexpression apparent from plasmid names (i.e. pZStesA expressing tesA). "Δgene" represents gene deletion.

Figure 12:
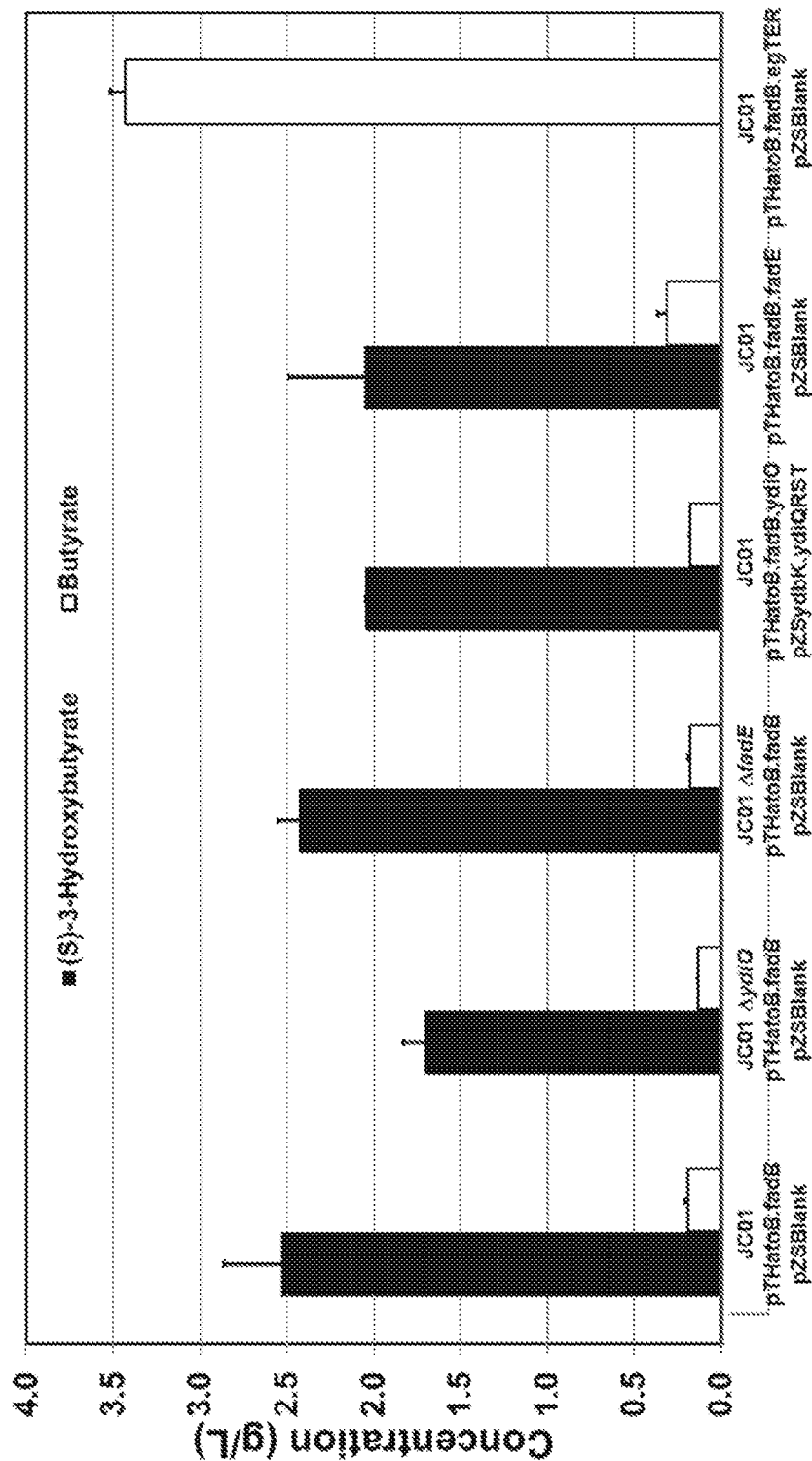

FIG. 12. Functional assessment of candidate acyl-CoA dehydrogenase/trans-enoyl-CoA reductase enzymes during the in vivo assembly of a full one-turn β-oxidation reversal. (S)-3-hydroxybutyrate and butyrate production with AtoB and FadB overexpression in the host strain combined with native acyl-CoA dehydrogenase (fadE, ydiO) chromosomal deletion or acyl-CoA dehydrogenase/trans-enoyl-CoA reductase (egTER) expression. Gene overexpression apparent from plasmid names (i.e. pTHatoB.fadB.egTER expressing atoB, fadB, and egTER). "Δgene" represents gene deletion.

Figure 13A:
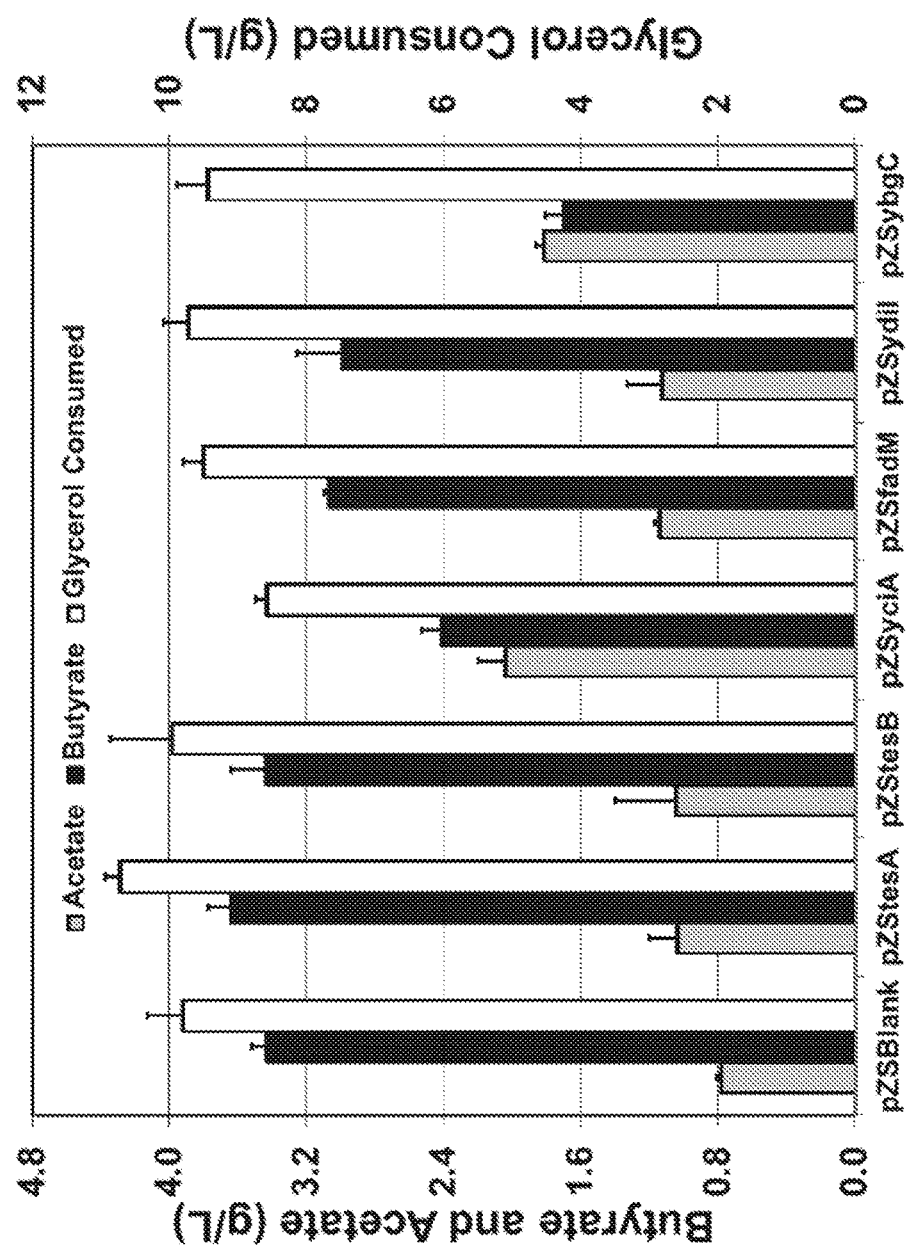
Figure 13B:
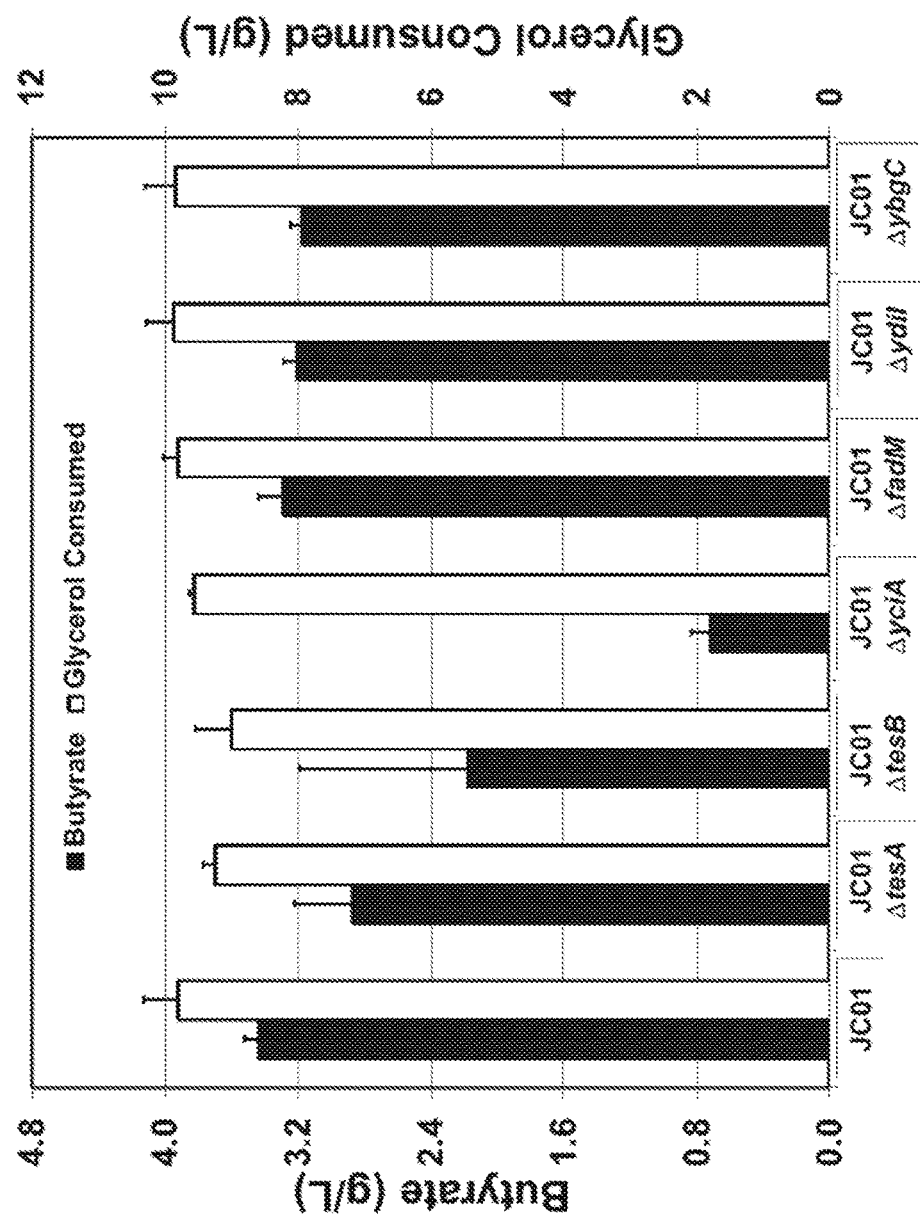

FIG. 13A-B. Termination pathway manipulation with a functional full one-turn β-oxidation reversal. (A) Glycerol consumption, butyrate, and acetate production in JC01 upon thiolase (AtoB), 3-hydroxyacyl-CoA dehydrogenase (FadB), enoyl-CoA hydratase (FadB), and trans-enoyl-CoA reductase (egTER) expression (i.e. pTHatoB.fadB.egTER) in combination with thioesterase overexpression via controllable construct. (B) Glycerol consumption and butyrate production in JC01 harboring pTHatoB.fadB.egTER and pZSBlank with native thioesterase chromosomal deletion. Gene overexpression apparent from plasmid names (i.e. pTHatoB.fadB.egTER expressing atoB, fadB, and egTER). "Δgene" represents gene deletion.

Figure 14:
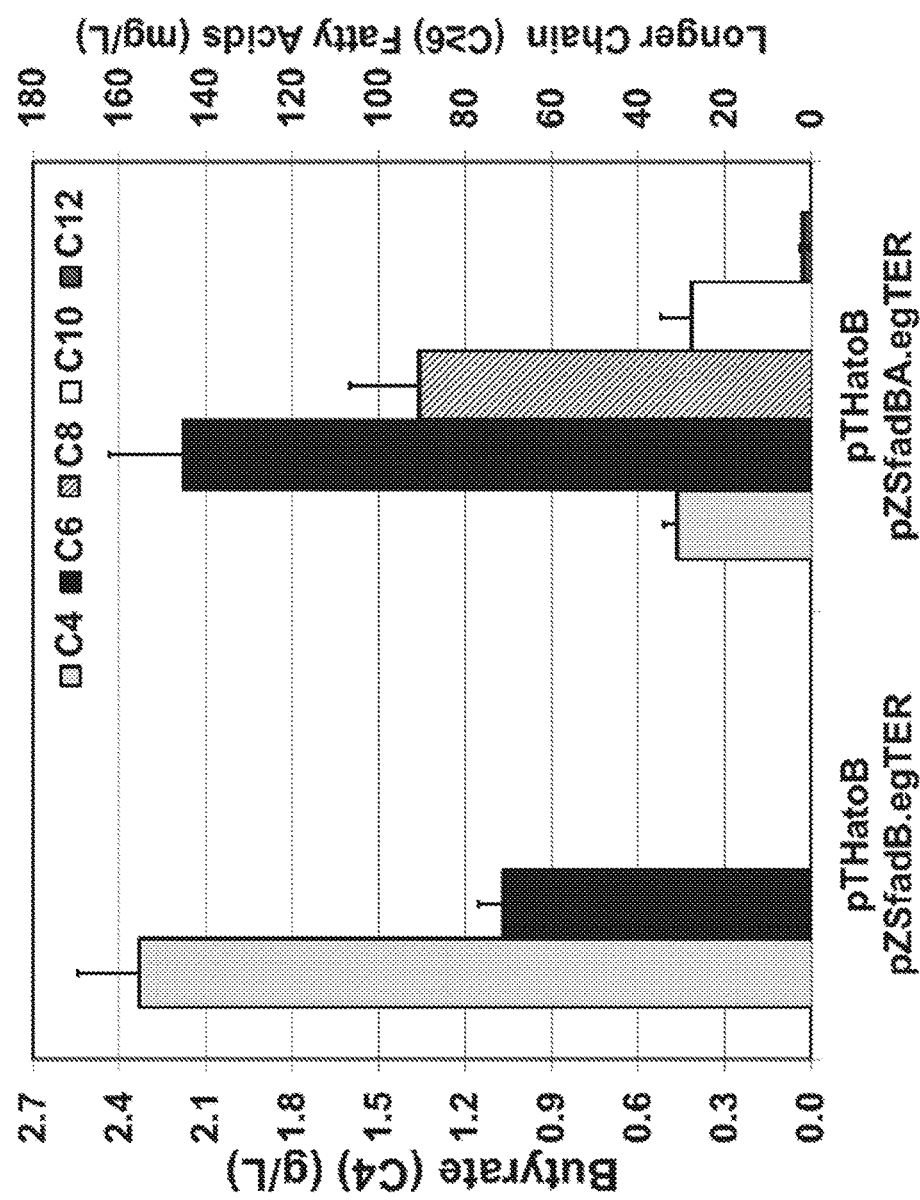

FIG. 14. Operation of multiple cycle turns during a functional reversal of the β-oxidation cycle for the synthesis of longer chain products. Distribution of extracellular fatty acid production by JC01 upon the expression of the functional units for a full one turn reversal (pTHatoB pZSfadB.egTER) and with the inclusion of the long-chain specific thiolase FadA (pTHatoB pZSfadBA.egTER). C6, hexanoic (caproic) acid; C8, octanoic (caprylic) acid; C10, decanoic (capric) acid; C12, dodecanoic (lauric) acid. Gene overexpression apparent from plasmid names (i.e. pZSfadBA.egTER expressing fadB, fadA, and egTER).

Figure 15:
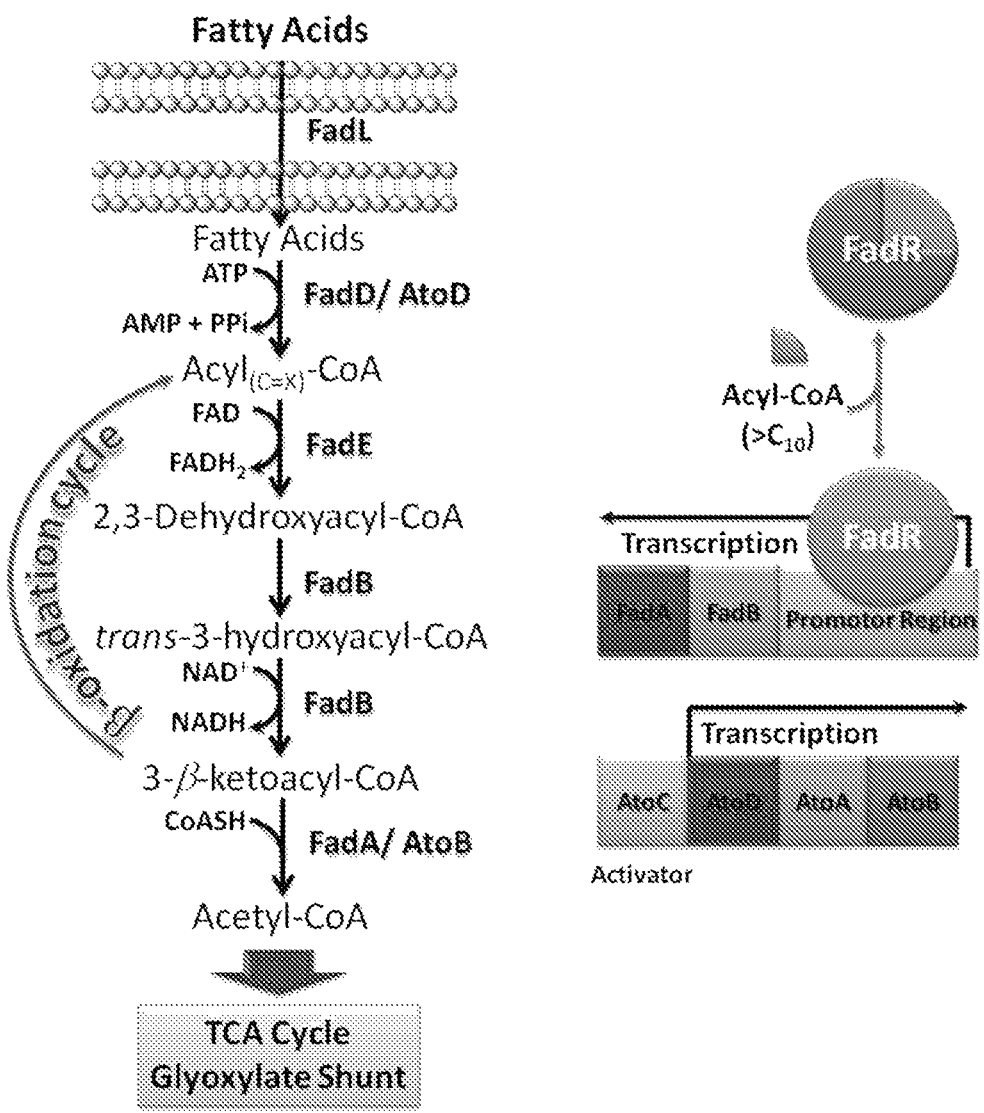
Figure 16A:
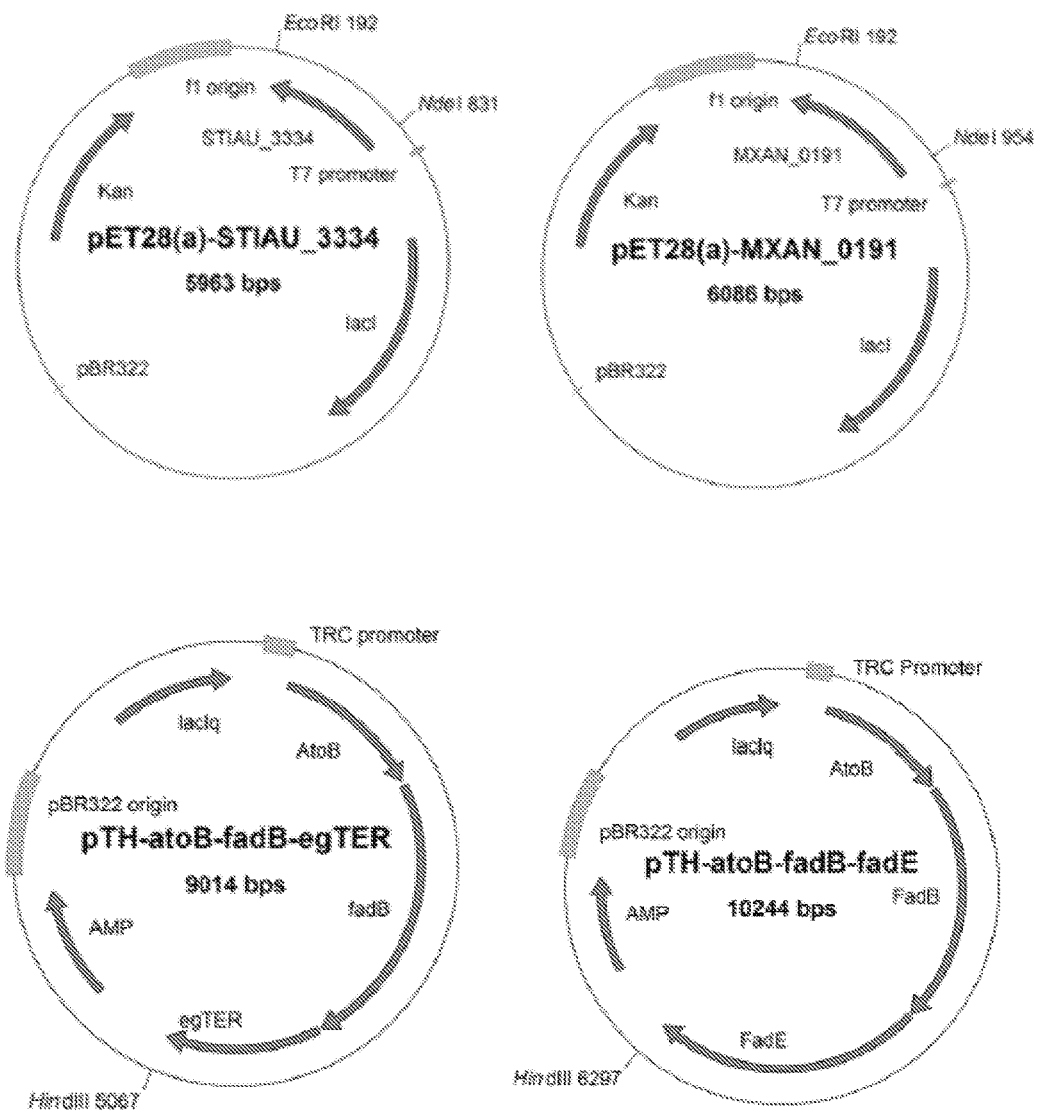
Figure 16B:
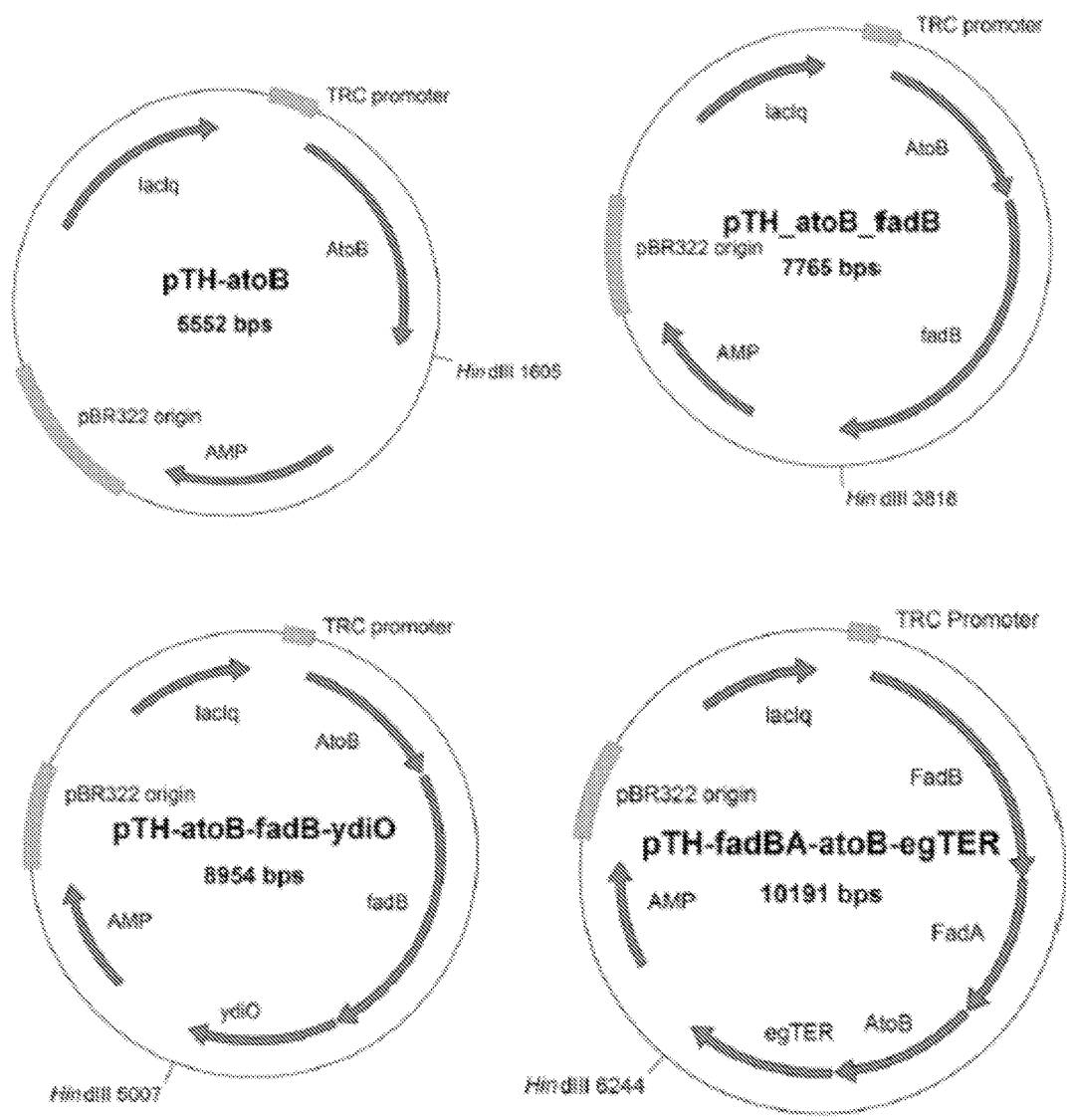
Figure 16C:
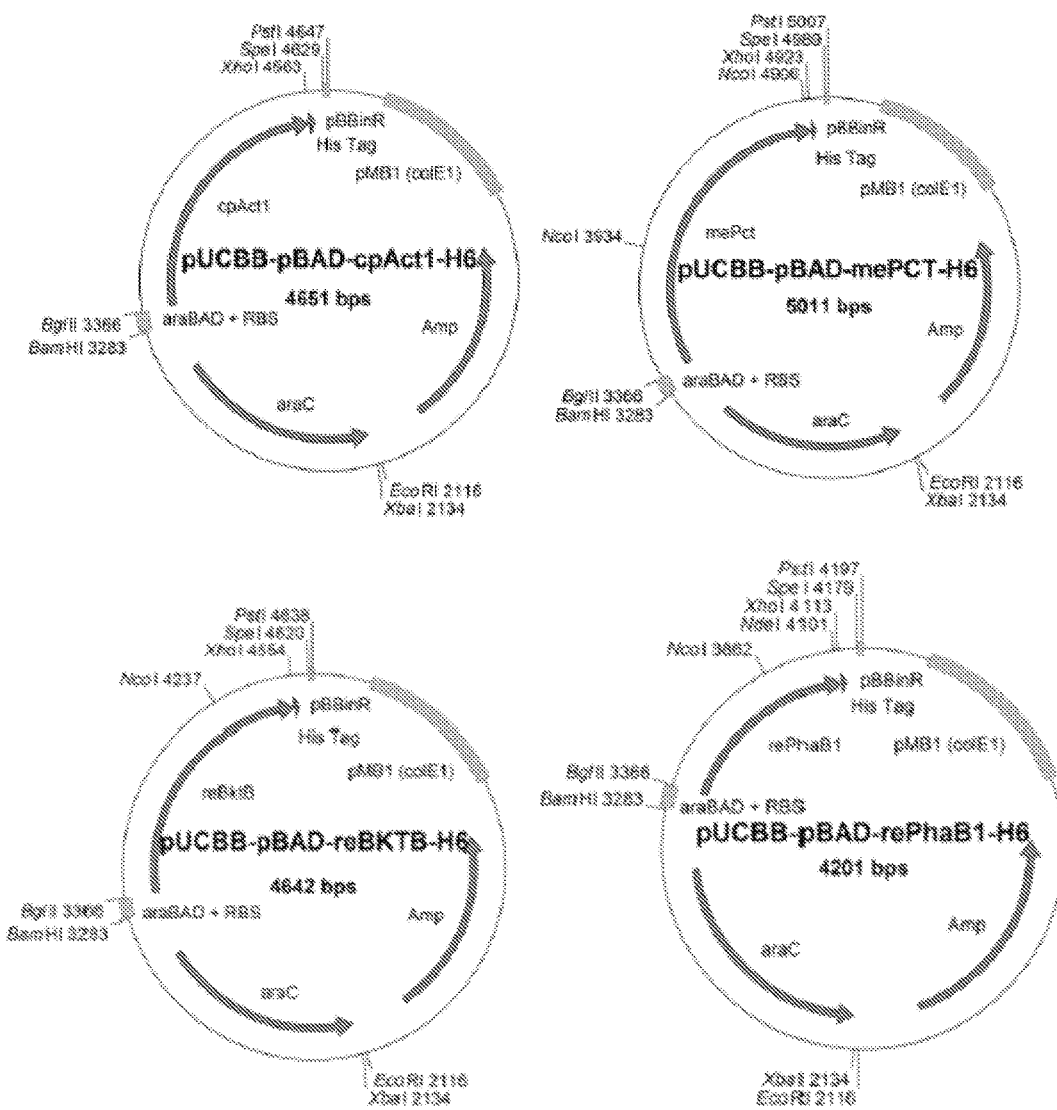
Figure 16D:
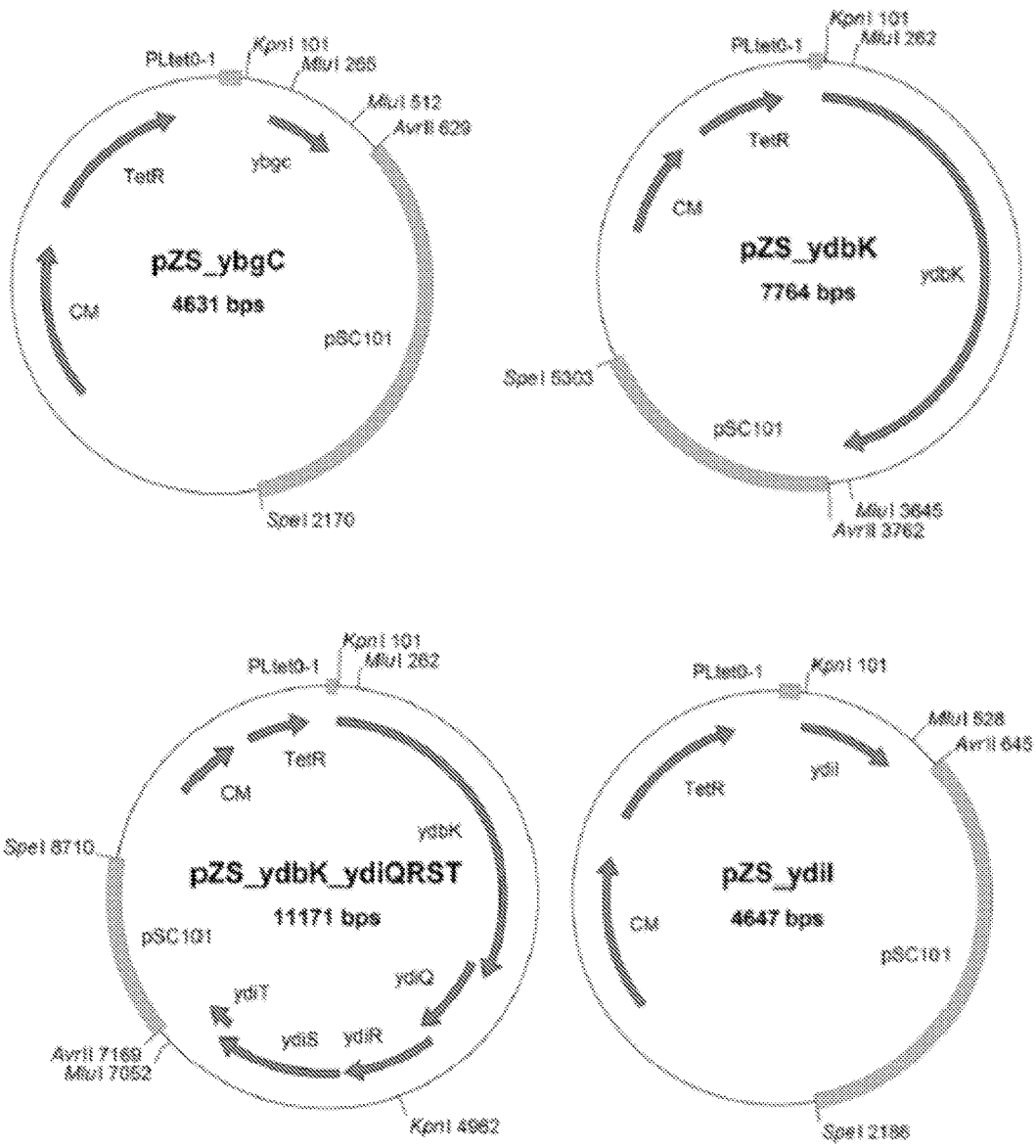
Figure 16E:
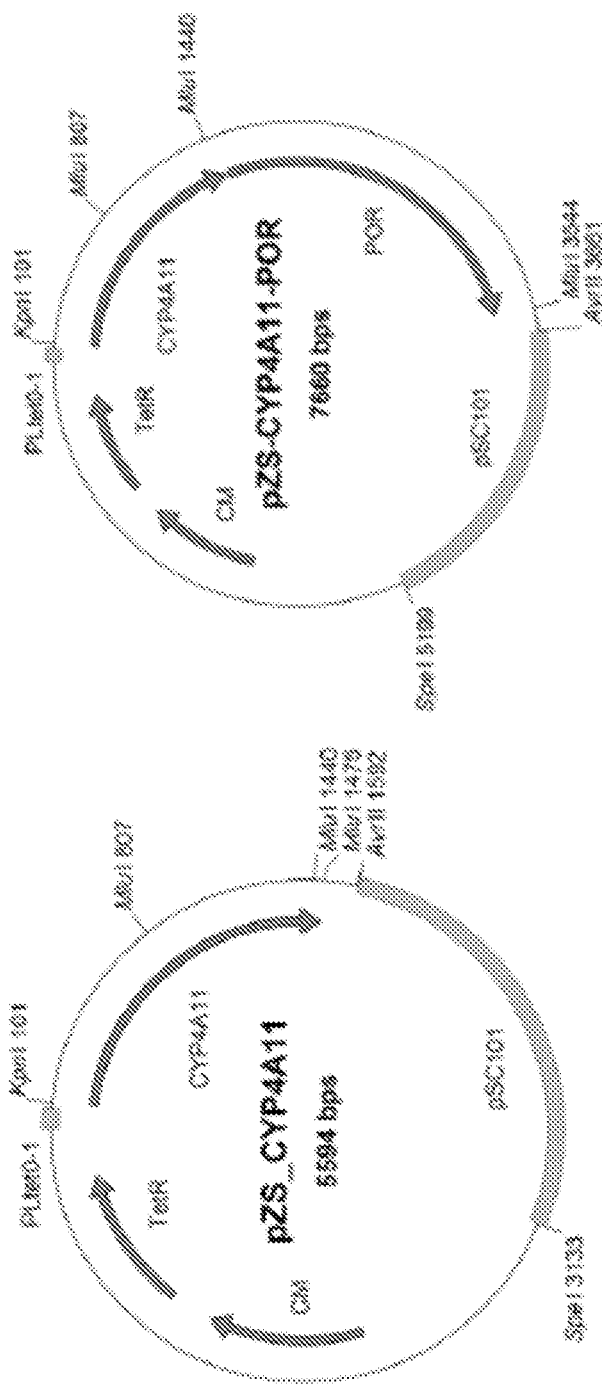
Figure 16F:
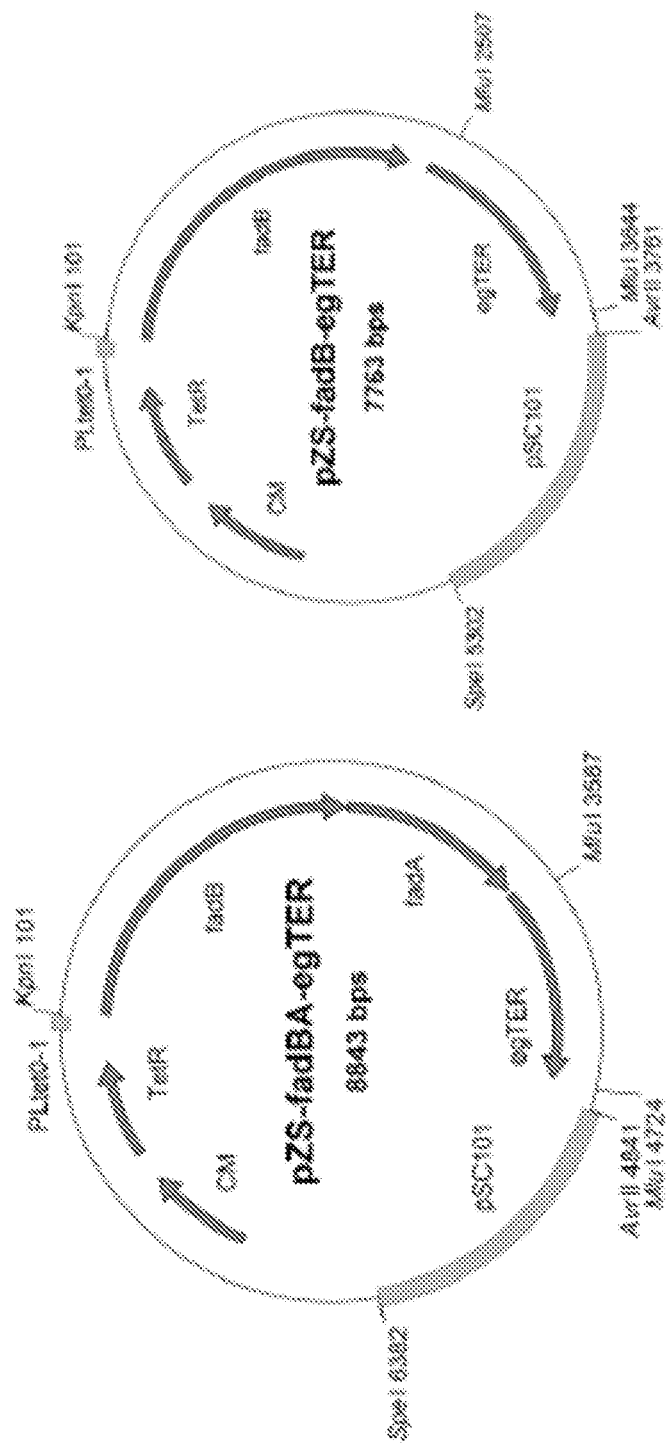
Figure 16G:
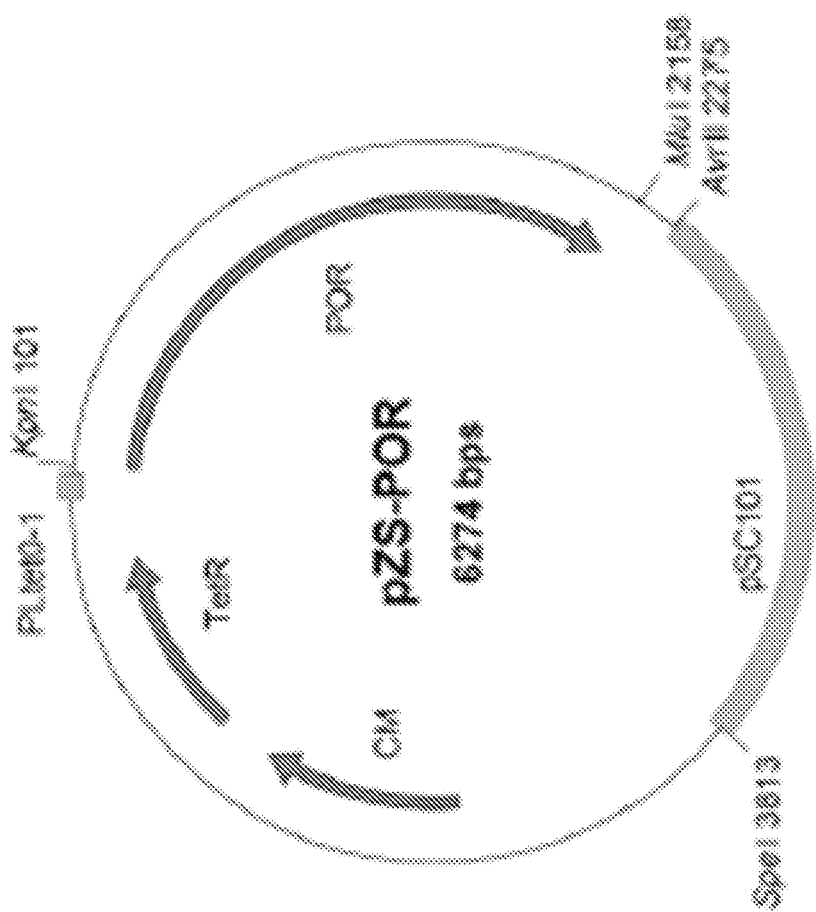

FIG. 15. β-oxidation cycle for the catabolism of fatty acids.

FIG. 16A-G. Representative expression vectors constructed for the engineering of the β-oxidation reversal to use the different primers and termination pathways outlined in this invention. Overexpressed genes are evident from the vector name (i.e. pTH-atoB.fadB.fadE expressing the atoB, fadB, and fadE genes) and details on each gene can be found in the representative Tables and throughout the specification.

DETAILED DESCRIPTION OF THE INVENTION

Two general approaches are used in the invention to functionalize the alpha and omega carbons:
 i) use of a primer or starter with a functionalized omega carbon, or
 ii) functionalizing the alpha/omega carbon of an intermediate or a product of the engineered reversal of the β-oxidation cycle.

The latter could take place before or after the intermediates of the engineered reversal of the β-oxidation cycle have been converted to carboxylic acids and n-alcohols by the appropriate termination enzymes.

These two approaches are detailed below.

Use of Omega Hydroxylated and Omega Carboxylated Primer/Starter Molecules in the Engineered Reversal of the β-Oxidation Cycle:

The "normal/standard" starter/primer used in the engineered reversal of the β-oxidation cycle is acetyl-CoA, which leads to the synthesis of even-chain n-alcohols and carboxylic acids (61/440,192). Propionyl-CoA can also be used as starter unit/primer by thiolase(s) thus enabling the synthesis of odd-chain carboxylic acids and n-alcohols (61/440,192).

A methyl group is always found at the omega end (omega or ω is the carbon most distant from the carboxyl group of the fatty acid) of both of the aforementioned starter/primer molecules. The use of starter/primer molecules with an omega hydroxylated or omega carboxylated carbon (i.e. a functionalized omega end) will then lead to the synthesis of carboxylic acids and alcohols through the β-oxidation reversal that will contained a functionalized omega end: e.g., omega-hydroxylated carboxylic acids, omega-carboxylated n-alcohols, dicarboxylic acids, and diols.

Figure 1A:
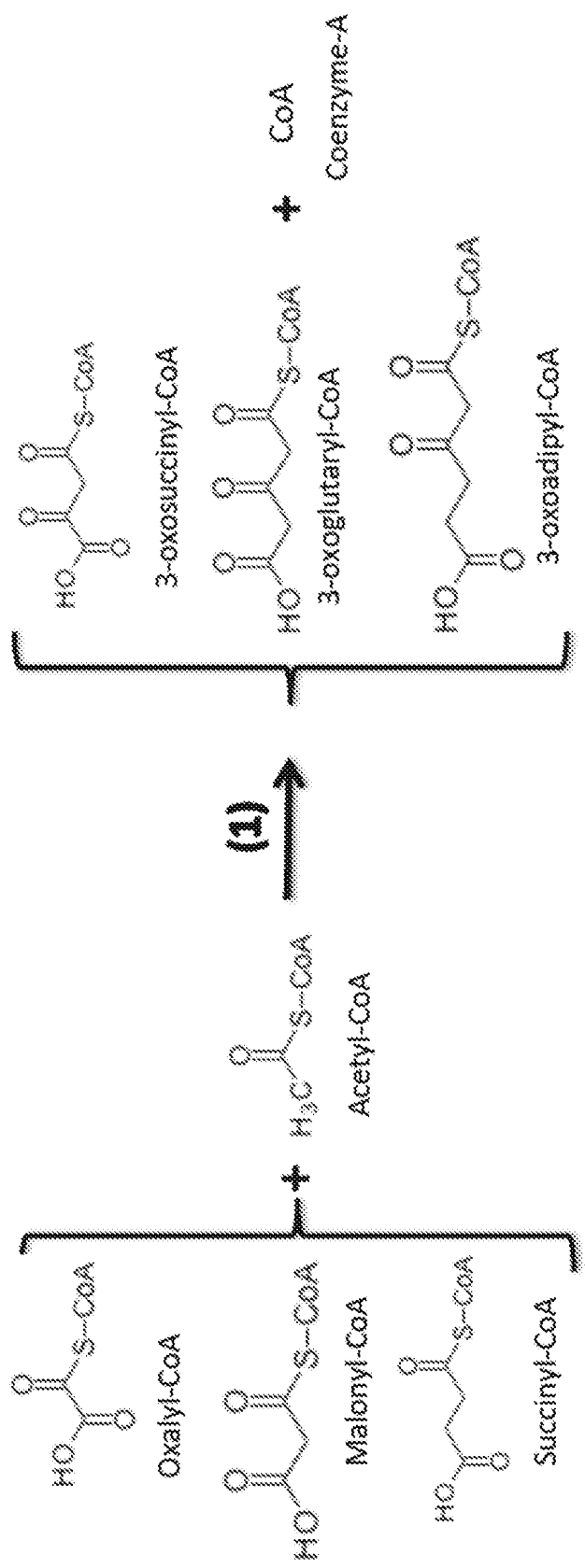
FIGS. 1A-C. Native and engineered thiolases capable of using omega-carboxylated (A), omega-hydroxylated (B), and omega-aminated (C) primers or starter molecules. The resulting omega-carboxylated, omega-hydroxylated, and omega-aminated keto-acyl-CoAs then undergo reduction and dehydration steps in the beta-oxidation reversal and support the synthesis of omega-hydroxylated, omega-carboxylated, and omega-aminated n-alcohols and carboxylic acids. (1) indicates native or engineered thiolases capable of using oxalyl-CoA, malonyl-CoA, and succinyl-CoA as primers or starter molecules. The following 3-oxoadipyl-CoA thiolases [EC:2.3.1.16/EC:2.3.1.174] are examples of such enzymes and catalyze the reversible conversion of 3-oxoadipyl-CoA to succinyl-CoA and acetyl-CoA during the degradation of aromatic compounds: *E. coli* PaaJ (Mascaraque et al., 2010, PNAS 107:14390-14395; Nogales et al., 2007, Microbiology 153:357-365), *Pseudomonas* sp. Strain B13 CatF (Gobel et al., 2002, J. Bacteriol. 184:216-223), *Rhodococcus opacus* PcaF and CatF (Eulberg et al., 1998, J. Bacteriol. 180:1072-1081), and *Streptomyces* sp. 2065 PcaF (Iwagami et al., 2000, Appl. Environ. Microbiol. 66:1499-1508). (2) indicates native or engineered thiolases capable of using hydroxyacetyl-CoA, 3-hydroxypropionyl-CoA, and 4-hydroxybutyryl-CoA as primers or starter molecules. (3) indicates native or engineered thiolases capable of using 2-aminoacetyl-CoA, 3-aminopropionoyl-CoA, and 4-aminobutyryl-CoA as primers or starter molecules. In addition to those enzymes listed in (1) above, several native beta-ketothiolases [EC: 2.3.1.9] shown to condense acyl-CoA molecules with acetyl-CoA could potentially catalyze the above reactions (1, 2, or 3), such as *E. coli* AtoB (Sato et al., 2007, J. Biosci. Bioeng. 103:38-44), YqeF, and FadA (Dellomonaco et al., 2011, Nature 476, 355-359), *Ralstonia eutropha* PhaA (Sato et al., 2007, J. Biosci. Bioeng. 103:38-44) and BktB (Slater et al., 1998, J Bacteriol. 180:1979-1987), and *Clostridium acetobutylicum* ThlA and ThlB (Winzer et al., 2000, J. Mol. Microbiol. Biotechnol. 2:531-541). Also, BktB has been shown to condense acetyl-CoA and propionyl-CoA and also has been used to condense some functionalized (omega-hydroxylated) CoA molecules with acetyl-CoA (WO2010101651).
Figure 1B:
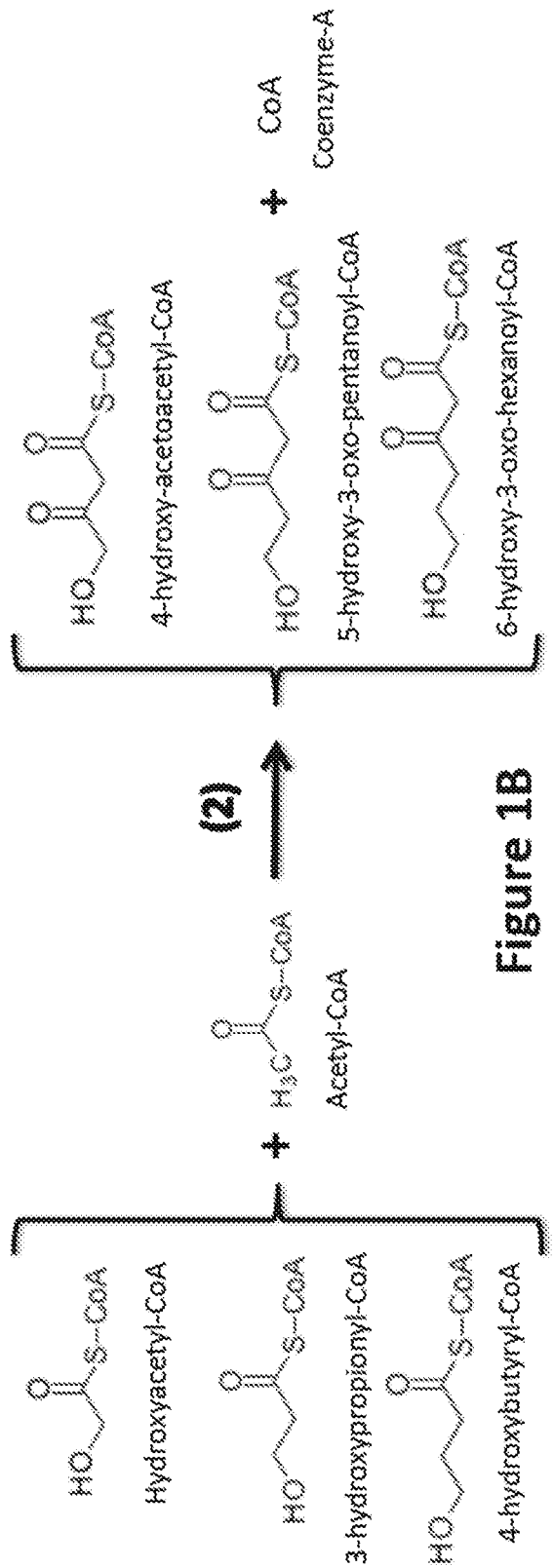
Figure 1C:
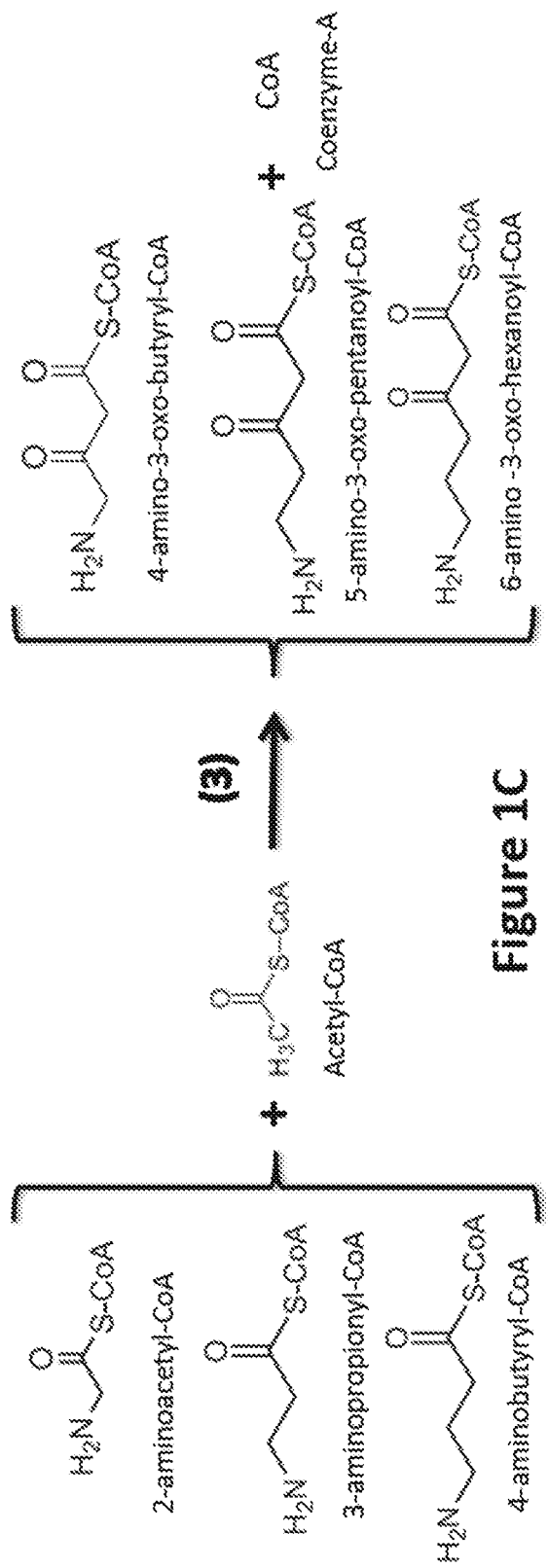
Figure 2:
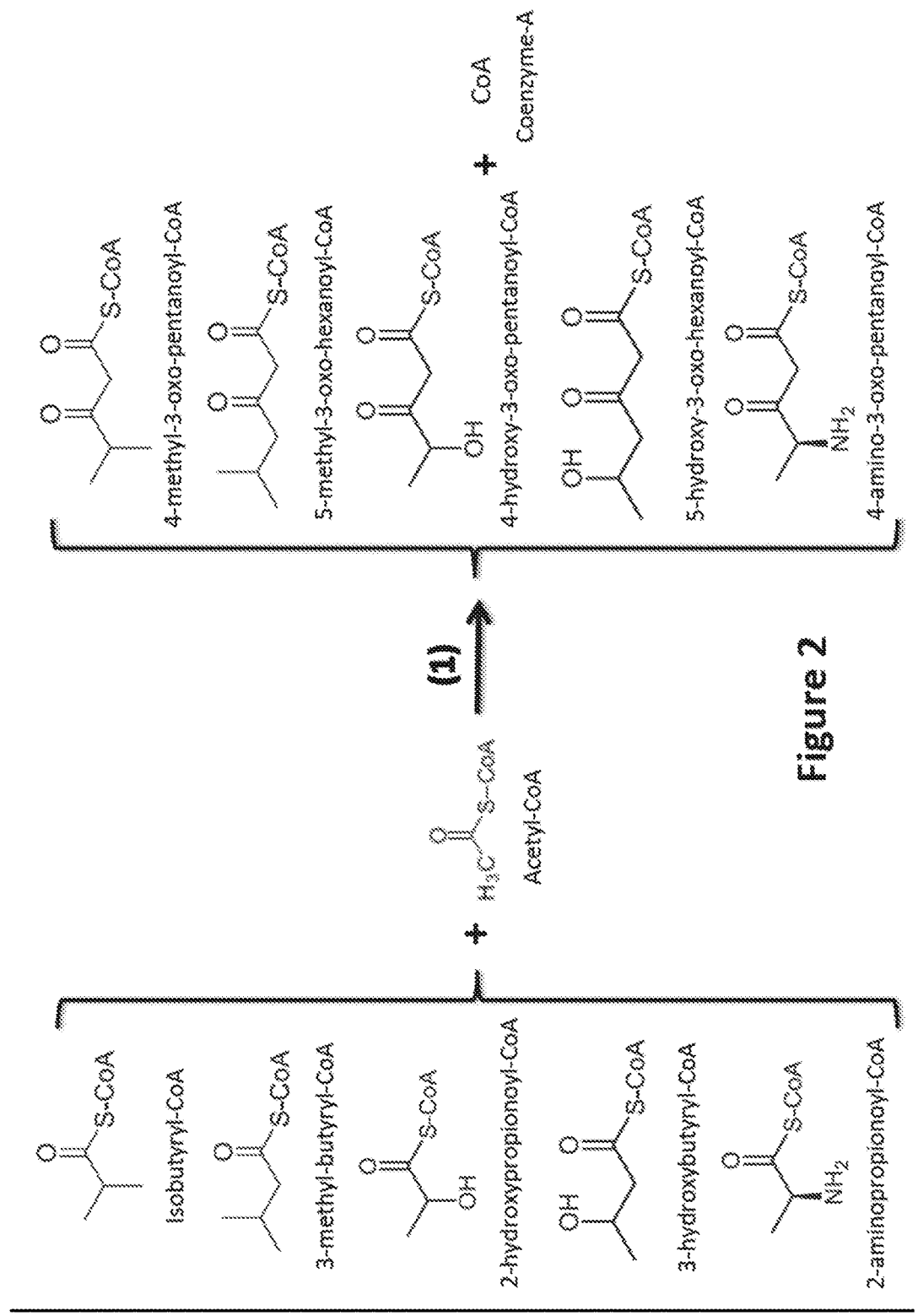
FIG. 2. Native and engineered thiolases capable of using non-terminal/secondary carbon functionalized compounds such as branched, hydroxylated, or aminated functionalized molecules as primers or starter molecules. The resulting functionalized keto-acyl-CoAs then undergo reduction and dehydration steps in the beta-oxidation reversal and support the synthesis of non-terminal/secondary carbon functionalized n-alcohols and carboxylic acids. (1) indicates native or engineered thiolases capable non-terminal/secondary carbon compounds such as isobutyryl-CoA, 3-methyl-butyryl-CoA, 2-hydroxypropionyl-CoA, 3-hydroxybutyryl-CoA, and 2-aminopropionyl-CoA as primers or starter molecules. The thiolases listed in FIG. 1 are all possible candidates for performing these condensation reactions.
Figure 3:
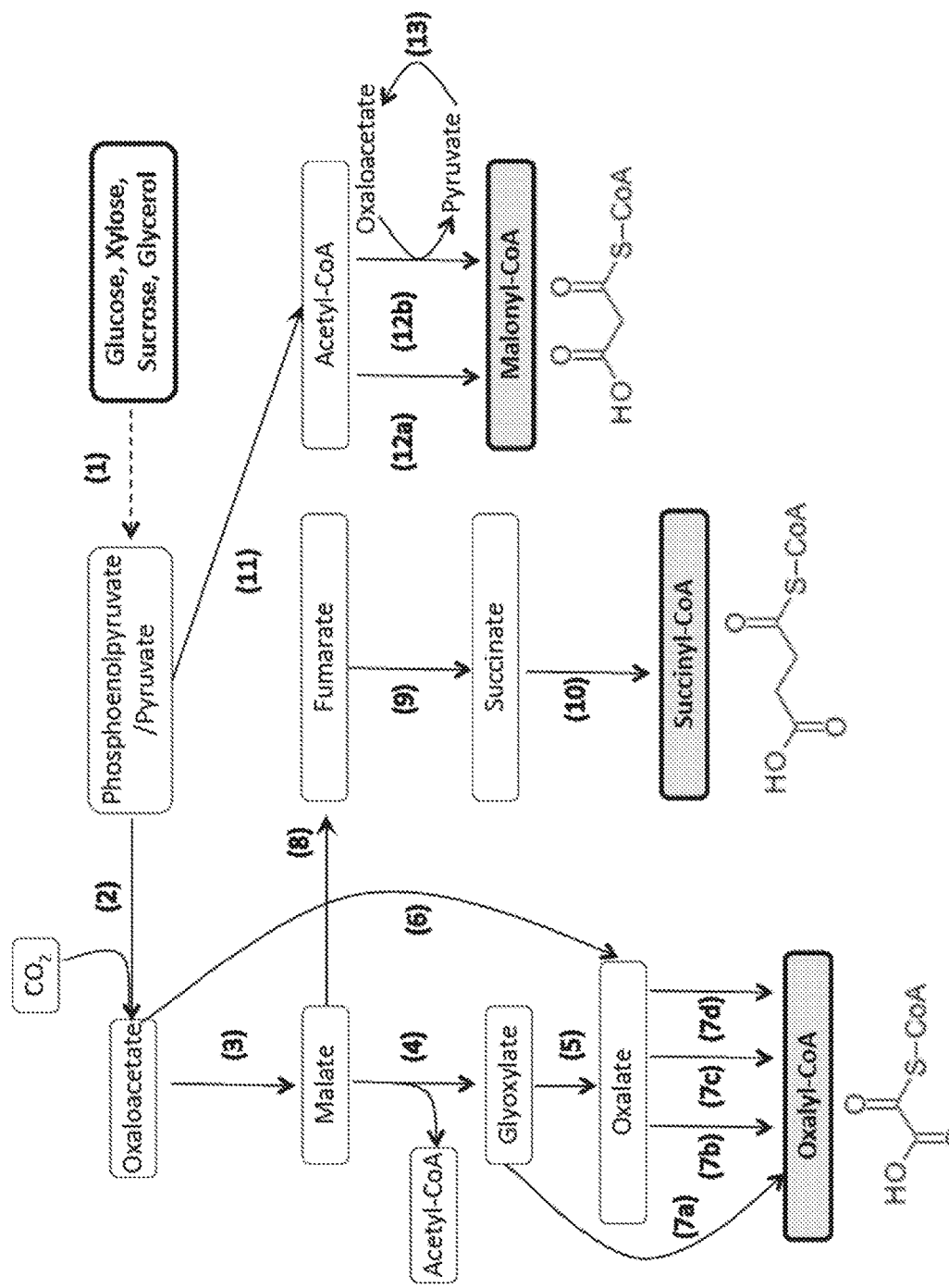
FIG. 3. Synthesis of omega-carboxylated acyl-CoAs oxalyl-CoA, malonyl-CoA, and succinyl-CoA, which can then function as primers in the reverse beta-oxidation cycle. Numbers indicate enzymes catalyzing the indicated conversions. (1) carbon utilization and glycolytic pathways; (2) phosphoenolpyruvate carboxylase [EC:4.1.1.31] or phosphoenolpyruvate carboxykinase [EC:4.1.1.49] or pyruvate carboxylase [EC:6.4.1.1]; (3) malate dehydrogenase [EC:1.1.1.37]; (4) acetyl-CoA:glyoxylate C-acetyltransferase (thioester-hydrolysing, carboxymethyl-forming)/L-Malate glyoxylate-lyase (CoA-acetylating) [EC:2.3.3.9]; (5) Glyoxylate:oxygen oxidoreductase/glyoxylate oxidase (glyoxylate+oxygen+H2O=hydrogen peroxide+oxalate+H+) [EC:1.2.3.5]; (6) *Botryotinia fuckeliana* oxaloacetate acetylhydrolase, oahA (oxaloacetate+H2O→oxalate+acetate+H+) [EC: 3.7.1.1]; (7a) Glyoxylate:NADP+ oxidoreductase (CoA-oxalylating) (Glyoxylate+CoA+NADP+ <=>Oxalyl-CoA+NADPH+H+) [EC:1.2.1.17]; (7b) *Cupriavidus oxalaticus* succinyl-CoA:oxalate CoA-transferase (oxalate+succinyl-CoA→oxalyl-CoA+succinate) [EC:2.8.3.2]; (7c) *E. coli* or *Oxalobacter formigenes* formyl-CoA transferase, frc (formyl-CoA+oxalate→formate+oxalyl-CoA) [EC:2.8.3.16]; (7d) oxalyl-CoA synthetase (oxalate+ATP+coenzyme A=oxalyl-CoA+diphosphate+AMP) [EC:6.2.1.8]; (8) fumarase [EC:4.2.1.2]; (9) FADH2-/NADH/ubiquinol/menaquinol-dependent fumarate reductase [EC:1.3.99.1/EC:1.3.1.6/EC:1.3.5.4]; (10) succinyl-CoA synthetase/ligase (ATP+Succinate+CoA<=>ADP+Orthophosphate+Succinyl-CoA) [EC:6.2.1.5], succinyl-CoA: acetoacetate CoA-transferase (Succinyl-CoA+Acetoacetate<=>Succinate+Acetoacetyl-CoA) [EC:2.8.3.5]; (11) pyruvate dehydrogenase complex [EC:1.2.4.1], pyruvate formate-lyase [EC:2.3.1.54], pyruvate:flavodoxin/:ferredoxin oxidoreductase. [EC:1.2.7.1]; (12a) Acetyl-CoA:carbon-dioxide ligase (ATP+Acetyl-CoA+HCO3-<=>ADP+Orthophosphate+Malonyl-CoA) [EC:6.4.1.2]; (12b) Malonyl-CoA:pyruvate carboxytransferase (Malonyl-CoA+Pyruvate<=>Acetyl-CoA+Oxaloacetate) [EC:2.1.3.1]; (13) malic enzyme [EC:1.1.1.40/EC:1.1.1.38] and malate dehydrogenase ((S)-Malate+NAD+/NADP+ <=>Oxaloacetate+NADH/NADPH+H+) [EC:1.1.1.37/EC:1.1.1.82]. The omega-carboxylated keto-acyl-CoAs resulting from the condensation of oxalyl-CoA, malonyl-CoA, and succinyl-CoA with acetyl-CoA undergo reduction and dehydration steps in the β-oxidation reversal to generate the omega-carboxylated intermediates, which in turn supports the synthesis of omega-carboxylated n-alcohols and carboxylic acids.
Figure 4:
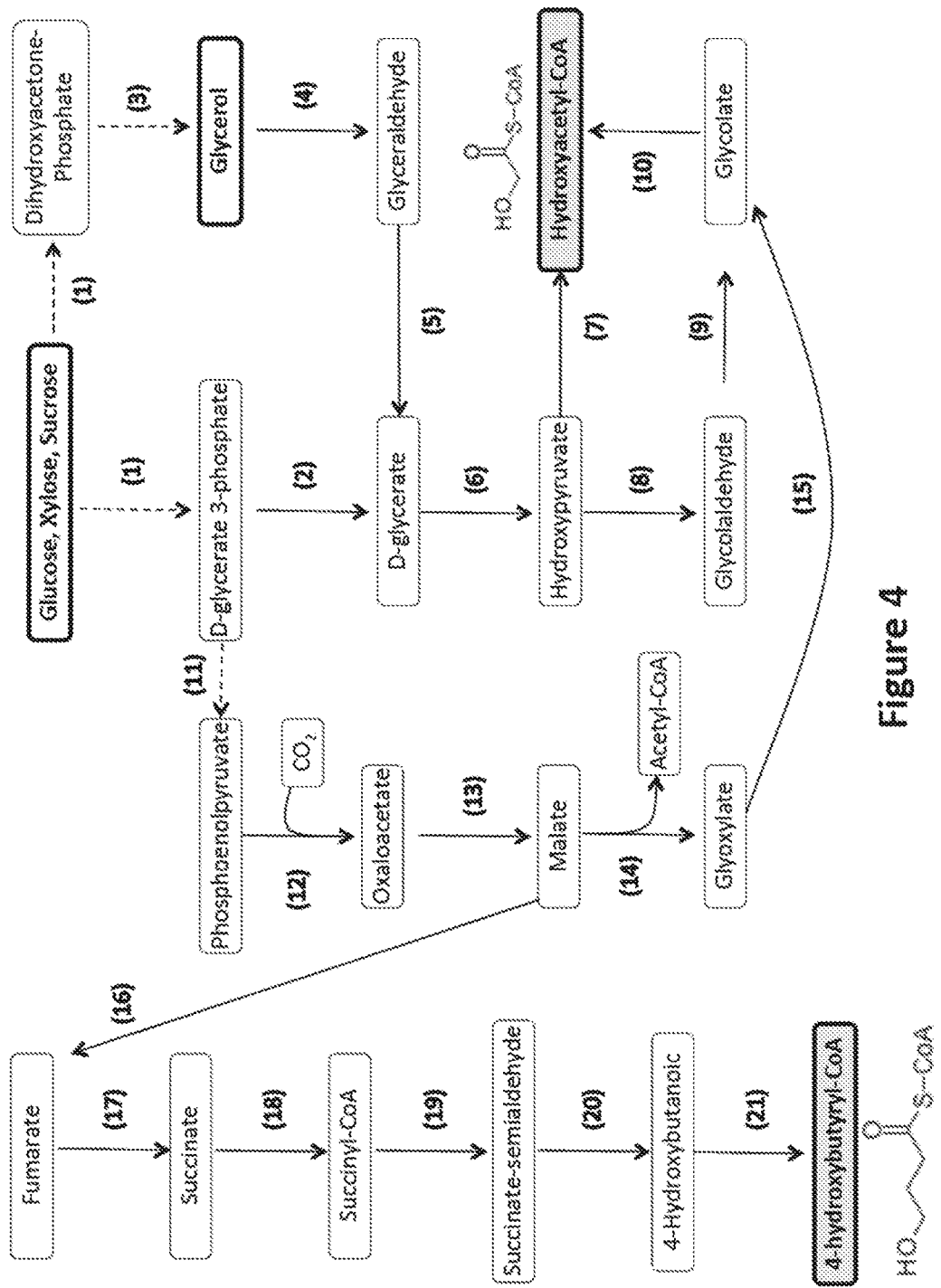
FIG. 4. Synthesis of omega-hydroxylated acyl-CoAs from hydroxyacetyl-CoA and 4-hydroxybutyryl-CoA primers. Numbers indicate enzymes catalyzing the indicated conversions. (1) enzymes catalyzing carbon-utilization and glycolytic pathways; (2) D-Glycerate-3-phosphate phosphohydrolase (3-Phospho-D-glycerate+H2O<=>D-Glycerate+Orthophosphate) [EC:3.1.3.38]; (3) Glycerol-3-phosphate dehydrogenase [EC:1.1.1.8/1.1.1.94] and glycerol-3-phosphatase [EC:3.1.3.21] (Two-steps with glycerol-3-phosphate intermediate); (4) Glycerol:NAD+/NADP+ oxidoreductases (Glycerol+NAD+/NADP+<=>D-Glyceraldehyde+NADH/NADPH+H+) [EC:1.1.1.21/EC:1.1.1.72]; (5) D-Glyceraldehyde:NAD+ oxidoreductase (D-Glyceraldehyde+NAD++H2O<=>D-Glycerate+NADH+H+) [EC: 1.2.1.3] or glyceraldehyde ferredoxin oxidoreductase (D-Glyceraldehyde+H2O+Oxidized ferredoxin<=>D-Glycerate+H++Reduced ferredoxin) [EC:1.2.7.5]; (6) D-Glycerate:NAD+/NADP+2-oxidoreductases (D-Glycerate+NAD+/NADP+ <=>Hydroxypyruvate+NADH/NADPH+H+) [EC:1.1.1.29/EC:1.1.1.81]; (7) Pyruvate dehydrogenase complex, PDHC (Hydroxypyruvate+NAD++CoA→Hydroxyacetyl-CoA+NADH+CO2): PDHC from pea chloroplast exhibits activity on hydroxypyruvate (Camp and Randal, 1985, Plant Physiol. 77:571-577); (8) hydroxypyruvate carboxy-lyase (Hydroxypyruvate<=>Glycolaldehyde+CO2) [EC:4.1.1.40]; (9) glycolaldehyde:NAD+oxidoreductase (Glycolaldehyde+NAD++H2O<=>Glycolate+NADH+H+) [EC:1.2.1.21]; (10) engineered glyoxylate:NADP+ oxidoreductase, succinyl-CoA:oxalate CoA-transferase, formyl-CoA transferase, or oxalyl-CoA synthetase to use glycolate as substrate (Glycolate+ATP+CoA→Hydroxyacetyl-CoA+ADP); (11) common glycolytic steps; (12) phosphoenolpyruvate carboxylase [EC:4.1.1.31] or phosphoenolpyruvate carboxykinase [EC:4.1.1.49] or pyruvate carboxylase [EC:6.4.1.1]; (13) malate dehydrogenase [EC:1.1.1.37]; (14) acetyl-CoA:glyoxylate C-acetyltransferase (thioester-hydrolysing, carboxymethyl-forming)/L-Malate glyoxylate-lyase (CoA-acetylating) [EC:2.3.3.9]; (15) glyoxylate reductase: ghrB (*Escherichia coli* K-12 substr. MG1655); glyoxylate reductase/hydroxypyruvate reductase: ghrA (*Escherichia coli* K-12 substr. MG1655) (Glyoxylate+

The use of omega-hydroxylated and omega-carboxylated starter/primer molecules requires: i) a native or engineered thiolase that will use them as substrates to initiate the reversal of the β-oxidation cycle (FIG. 1), and ii) the metabolic synthesis/generation of these primers (FIG. 2-4).

In one scenario, the invention includes having two separate thiolases: a short-chain thiolase/acyltransferase with high affinity for the desired primer/starter molecule (native enzyme with desired properties or engineered AtoB/YqeF) (FIG. 1) and a thiolase with broad chain length specificity (e.g. β-oxidation complexes FadBA and FadJI) (61/440, 192).

In some cases YqeF/AtoB will need to be engineered to obtain mutants with preference for hydroxyacetyl-CoA, hydroxypropionyl-CoA, hydroxybutyryl-CoA, oxalyl-CoA, malonyl-CoA or succinyl-CoA as a primer/starter molecule over acetyl-CoA.

Some of these thiolases are already available in nature; for example *E. coli* PaaJ (Mascaraque et al., 2010, PNAS 107:14390-14395; Nogales et al., 2007, Microbiology 153:

357-365), *Pseudomonas* sp. Strain B13 CatF (Gobel et al., 2002, J. Bac. 184: 216-223), *Rhodococcus opacus* PcaF and CatF (Eulberg et al., 1998, J. Bacteriol. 180:1072-1081), and *Streptomyces* sp. PcaF (Iwagami et al., 2000, Appl. Environ. Microbiol. 66:1499-1508) are 3-oxoadipyl-CoA thiolases that catalyze the reversible conversion of 3-oxoadipyl-CoA to succinyl-CoA and acetyl-CoA during the degradation of aromatic compounds and hence can use succinyl-CoA as a primer/starter molecule.

Metabolic routes that would support the synthesis of the aforementioned omega-carboxylated and omega-hydroxylated primer/starter molecules are shown in FIGS. 2-4 and briefly described below:

Omega Carboxylated Primers—Oxalyl-CoA, Malonyl-CoA or Succinyl-CoA:

The use of malonyl-CoA as starter/primer molecule will support the synthesis of odd-chain dicarboxylic acids and omega-carboxylated n-alcohols. The use of oxalyl-CoA and succinyl-CoA as primers/starter molecules will support the synthesis of even-chain dicarboxylic acids and omega-carboxylated n-alcohols.

FIG. 3 shows engineered pathways to obtain oxalyl-CoA, malonyl-CoA or succinyl-CoA. This strategy will employ engineered thiolases capable of using oxalyl-CoA, malonyl-CoA or succinyl-CoA as primers/starter molecules in a condensation reaction with acetyl-CoA (FIG. 1A). An engineered AtoB or YqeF will be used to start the cycle and then FadBA and YdiO-YdiQRST will function in the other steps for all turns of the cycle.

Omega Hydroxylated Primers—Hydroxyacetyl-CoA, Hydroxypropionyl-CoA, and Hydroxybutyryl-CoA:

The use of hydroxyacetyl-CoA and hydroxybutyryl-CoA as starters/primer molecules will lead to the synthesis of even-chain 1,n-diols and omega-hydroxylated carboxylic acids. FIG. 4 shows engineered pathways to obtain these omega-hydroxylated acyl-CoAs. The use of hydroxypropionyl-CoA as the starter/primer molecule will lead to the synthesis of odd-chain 1,n-diols and omega-hydroxylated carboxylic acids.

FIG. 5 shows engineered pathways to obtain hydroxypropionyl-CoA. Two key aspects of this part of the invention are: i) a native or engineered acyl-CoA ligase to generate hydroxyacetyl-CoA from hydroxyacetate/glycolate, and ii) a native or engineered pyruvate dehydrogenase (FIG. 4, step 7) that preferentially converts hydroxypyruvate to hydroxyacetyl-CoA (instead of converting pyruvate to acetyl-CoA).

In the case of the thiolase reaction, engineered thiolases capable of using hydroxyacetyl-CoA, hydroxypropionyl-CoA and hydroxybutyryl-CoA as primers/starter molecules in a condensation reaction with acetyl-CoA (FIG. 1B) will be used. For example, an engineered AtoB or YqeF will be used to start the cycle and then FadBA and YdiO-YdiQRST will function in the other steps for all turns of the cycle.

Functionalization of Omega Carbons Using the ω-Oxidation Pathway:

Alkanes and long chain fatty acids are metabolized by industrially important yeasts and bacteria using the ω-oxidation pathway, a minor pathway for medium chain fatty acids. The methyl group at the ω carbon is first oxidized to a hydroxyl group, then to an oxo group, and finally to a carboxyl group. The long chain dicarboxylates derived from ω-oxidation then enter the β-oxidation cycle for further degradation. These enzymes are used in this invention to functionalize the ω carbon of carboxylic acids and n-alcohols generated by the β-oxidation reversal using as primer/starter one of the following molecules: acetyl-CoA, hydroxyacetyl-CoA, hydroxypropionyl-CoA, hydroxybutyryl-CoA, oxalyl-CoA, malonyl-CoA or succinyl-CoA. The functionalization involves the introduction of hydroxyl, aldehyde, or carboxylic groups in the ω carbon.

Omega Oxidation as the Key Pathway:

oxidation of an omega methyl group to either alcohol (1 step, generating a hydroxylated end) or carboxylic acid (2 steps from hydroxy to oxo to carboxy, generating a carboxylated end). The omega oxidation enzymes will act on the ω carbon of carboxylic acids or alcohols generated by the action of thioesterases and aldehyde-forming acyl-CoA reductases and alcohol dehydrogenases, respectively, on the different intermediates of the β-oxidation reversal.

The three enzymatic steps employed in this part of the invention are summarized below and are shown in FIG. 6A:

(1) Hydroxylation (Omega-Hydroxylation):
Fatty acid+2 NADPH+O2→ω-hydroxy fatty acid+ 2NADP+H2O
    long-chain fatty acid ω-hydroxylase: CYP704B1 (*Arabidopsis thaliana* col)
Laurate+NADPH/NADH+O2→ω-hydroxy laurate+ NADP/NAD+H2O
    laurate monooxygenase (*Helianthus tuberosus*) NADPH-dependent
    laurate monooxygenase: IMT-2 (*Petunia×hybrida*) NADPH-dependent
    lauric acid dehydroxylase: CYP76J1 (*Petunia×hybrida*) NADPH-dependent
    laurate ω-hydroxylase (*Pisum sativum*): NADH-dependent
a fatty acid+2 NADPH+oxygen<=>a in-chain hydroxy fatty acid+2 NADP++H2O Many other examples of P450 hydroxylases are provided in: Pinot F, Beisson F. (2011). Cytochrome P450 metabolizing fatty acids in plants: characterization and physiological roles. FEBS J, 278 (2), 195-205.

(2) Alcohol Oxidation
ω-hydroxy fatty acid+O2→ω-oxo fatty acid+H2O2
    omega-hydroxy fatty acid oxidase: AtFAO3 (*Arabidopsis thaliana* col)
    ω-hydroxy fatty acid oxidase: fao2 (*Candida cloacae*)
    ω-hydroxy fatty acid oxidase: fao1 (*Candida cloacae*)

(3) Keto Oxidation
ω-oxo fatty acid+NAD→dicarboxylic acid+NADH

Representative aldehyde oxidoreductases capable of this enzymatic step are provided in the following references: Hommel R and Kleber H P 1984. FEMS Microbiol. Lett. 22, 139-142; Shinagawa E, Toyama H, Matsushita K, Tuitemwong P, Theeragool G, Adachi O. 2006. Biosci. Biotechnol. Biochem. 70:850-857; Groen B, Frank J, Duine J A. 1984. Biochem. J. 223: 921-924; Zarnt G, Schrader T, Andreesen J R. 2001 J. Bacteriol. 183:1954-1960.

Functionalization of Alpha-Carbons Using the α-Oxidation Pathway:

Alpha oxidation (α-oxidation) is a process by which certain fatty acids are broken down by removal of a single carbon from the carboxyl end. Since 3-methyl fatty acids cannot be degraded through the β-oxidation cycle, the terminal carboxyl group is first removed by alpha-oxidation. Alpha-oxidation pathways are exemplified in FIGS. 6B and 6C.

The enzymatic steps involved in the alpha-oxidation pathway have been reported elsewhere (Jansen and Wanders: Biochimica et Biophysica Acta 1763 (2006) 1403-1412, see also en.wikipedia.org/wiki/Alpha_oxidation). Alpha-oxidation of phytanic acid has been investigated in detail. The pathway involves first the activation of phytanic acid to phytanoyl-CoA followed by 2-hydroxylation of phytanoyl-CoA by phytanoyl-CoA hydroxylase (PhyH/Pahx) to form 2-hydroxyphytanoyl-CoA.

Fatty acid α hydroxylases from *Myxococcus xanthus* (MXAN_0191) and *Stigmatella aurantiaca* (STIAU_3334) (Ring M W, Schwar G, Bode H B. 2009. ChemBioChem 10:2003-20) represent candidate enzymes for performing alpha hydroxylation on the products generated from a reversal of the β-oxidation cycle

THEORY OF THE INVENTION

The exploitation and engineering of biological systems enabling carbon-chain elongation has garnered significant attention in recent years due to the growing demand for the development of new technologies capable of producing advanced (long-chain) fuels and chemicals from renewable materials[1-4]. While the use of the fatty acid biosynthesis pathway has attracted the most attention[5-7], a recently engineered reversal of the β-oxidation cycle shows great promise as a metabolic platform for the synthesis of alcohols and carboxylic acids of varying carbon lengths and functionalities[8]. In contrast to the fatty acid biosynthesis pathway, this pathway operates with coenzyme A (CoA) intermediates and directly uses acetyl-CoA for acyl-CoA chain elongation, characteristics that could enable product synthesis at maximum carbon and energy efficiency[8].

Our previous work on engineering a functional reversal of the β-oxidation cycle in *Escherichia coli* focused on a top-down/system-level strategy that involved the manipulation of several global regulators[8]. A mutation that rendered FadR non-functional, in combination with a mutation in the cytoplasmic response regulator AtoC of the AtoSC two-component regulatory system, enabled the constitutive expression of all enzymes in the β-oxidation cycle in the absence of its natural substrate (fatty acids)[8]. Since several operons encoding β-oxidation cycle enzymes are also activated by the cyclic-AMP (cAMP) receptor protein (CRP)-cAMP complex and hence repressed by the presence of alternative carbon sources, we replaced the native crp gene with a cAMP-independent mutant (crp*) that confers a derepressed phenotype. Finally, since the anaerobic/microaerobic conditions used in the production of fuels and chemicals would lead to ArcA-mediated repression of most operons encoding the β-oxidation cycle, the arcA gene was deleted[8].

These system-level manipulations were then combined with a small set of local perturbations (elimination of native fermentation pathways and expression of selected termination pathways) to achieve the synthesis of desired products. While effective, this system-level approach has some limitations due to the ill-defined nature of the individual components of the engineered pathway. This, in turn, limits the ability to effectively manipulate such individual components to fine-tune the synthesis of specific products and prevents the transfer of the engineered pathways to other host organisms (i.e. "equivalent" global regulators would need to be engineered in other hosts to implement a functional reversal of the β-oxidation cycle).

In order to overcome these limitations, the approach taken here focuses on a synthetic biology strategy in which the target pathway is built from well-defined and self-contained functional units that can be assembled in different combinations to achieve the synthesis of a wide array of products. This bottom-up approach implies that an effective design is created through the assembly of pre-defined components or building blocks (i.e. each functional units/enzymes composing the pathway)[9]. Thus, the reconstruction of a functional reversal of the β-oxidation cycle can be accomplished without engineering global regulators and hence creating a "clean" platform that can be readily transferred to other hosts/organisms.

The implementation of the above approach entails i) in vitro kinetic characterization of individual components of the pathway, and ii) in vivo assembly and characterization of the functional pathway. To this end, suitable enzyme(s) for each functional unit comprising the thiolase, 3-hydroxyacyl-CoA dehydrogenase, enoyl-CoA hydratase/3-hydroxyacyl-CoA dehydratase, and acyl-CoA dehydrogenase/trans-enoyl-CoA reductase elements of the core pathway (FIG. 8) were purified and tested through in vitro kinetic characterization. We initially focused our efforts on a one-turn reversal of the β-oxidation cycle as the basic platform but selected enzymes that could also serve as a functional component of a multiple turn cycle reversal.

While these four principle components encompass the entire reversal of the β-oxidation cycle, product synthesis also requires the integration of a termination pathway into the modular framework. In order to provide a functional assessment of each core unit as the pathway is built, thioesterases capable of converting each CoA pathway intermediate into their respective carboxylic acid counterpart were selected and utilized as the termination pathway(s). This approach enabled the use of carboxylic acids as proxy for product synthesis (e.g. 4-C carboxylic acids produced during a functional one-turn reversal of the β-oxidation cycle).

Once identified and characterized, the assembly and in vivo characterization of each functional unit of the core pathway was conducted. We selected *E. coli* as the initial chassis for pathway assembly due to its advantageous traits for industrial biofuel and biochemical production[10] and as a chassis for synthetic biology applications[9]. In addition, to demonstrate the feedstock-independent nature of the functional components (i.e. only requires the generation of acetyl-CoA from a given carbon source), glycerol was selected as the carbon source. Finally, the metabolism of *E. coli* was re-programmed and tailored for the synthesis 4-C and longer chain products through local perturbations and the modular assembly of each individual component. This reconstructed pathway can now be used for the synthesis of a wide-range of products by engineering the priming (using different primers) and termination (using different termination pathways) steps, as described in this invention.

Reverse Beta Oxidation

A functional reversal of the β-oxidation cycle results in the two-carbon elongation of an acyl-CoA intermediate per cycle of operation. This metabolic process requires the integration of 4 key components for core pathway function: i) a thiolase that catalyzes the condensation of acetyl-CoA with an acyl-CoA, yielding a ketoacyl-CoA; ii) a hydroxyacyl-CoA dehydrogenase that reduces ketoacyl-CoA to hydroxyacyl-CoA; iii) an enoyl-CoA hydratase/3-hydroxyacyl-CoA dehydratase that generates transenoyl-CoA from hydroxyacetyl-CoA; and iv) an acyl-CoA dehydrogenase/trans-enoyl-CoA reductase that reduces trans-enoyl-CoA to an acyl-CoA two carbons longer than the initial acyl-CoA (FIG. 8).

In its simplest form, a one-turn reversal, these reactions result in the elongation of the initial acetyl-CoA molecule to butyryl-CoA. In addition to the aforementioned components, product synthesis also requires the integration of a termination pathway capable of converting each CoA pathway intermediate into the desired product. Thus, these elongated components can be functionalized or used as intermediates in another turn, as shown in FIG. 7.

In the work reported here we used thioesterases to convert CoA thioesters intermediates into their respective carboxylic acid counterpart (FIG. 8). Each component is addressed in turn below.

Thiolase

Four *E. coli* thiolases involved in the β-oxidation of fatty acids[11] (atoB, yqeF, fadA, fadI) can potentially catalyze the condensation of acetyl-CoA with acyl-CoA of various chain lengths. Among them, AtoB and FadA have been studied the most. AtoB exhibits higher specificity for short-chain acyl-CoA molecules[12,13], while FadA is part of the FadBA multienzyme complex with broad chain-length specificity for acyl-CoA substrates[14].

Considering their well-studied nature, AtoB and FadA were selected as the most viable thiolase candidates and further in vitro characterization were undertaken to ensure their compatibility in the framework of a functional β-oxidation reversal. Upon purification and kinetic characterization, AtoB was shown to effectively catalyze the condensation of two acetyl-CoA molecules with a $k_{cat}/K_M$ of $3.55 \times 10^3$ $M^{-1}s^{-1}$ showing its potential as a short-chain specific thiolase component for initiation of a one-turn β-oxidation reversal (Table 1), and hence priming a cycle of multiple turns. On the other hand, while substrate saturation with FadA during the kinetic characterization was not possible, the estimated (See Methods) $k_{cat}/K_M$ of 7.47 $M^{-1}s^{-1}$ for the condensation of acetyl-CoA molecules shows FadA is not a viable candidate for this initial condensation reaction (Table 1).

It is important to note however that when one considers multiple turns of the functional reversal of the β-oxidation cycle with longer chain length intermediates, the broad chain-length specificity of FadA for longer-chain acyl-CoA substrates[14] could convey the ability to facilitate multiple cycle turns with a single enzyme after the initial priming of the cycle by AtoB. Also of note is the fact that both AtoB and FadA appear to be more efficient in the catabolic direction (i.e. conversion of acetoacetyl-CoA into 2 acetyl-CoA molecules) (Table 1). This could pose an issue during in the in vivo assembly of components without appropriate driving forces, such as the thermodynamic driving force of metabolite pools of substrates and products[15], in place to ensure the biosynthetic reaction is favored.

3-Hydroxyacyl-CoA Dehydrogenase

Three *E. coli* enzymes could potentially encode 3-hydroxyacyl-CoA dehydrogenase activity: two hydroxyacyl-CoA dehydrogenases (fadB and fadJ), which are involved in the β-oxidation of fatty acids[11], and a 3-hydroxyadipyl-CoA dehydrogenase (paaH) that participates in the degradation of phenylacetate[16]. While involved in degradative pathways, these three enzymes catalyze reversible reactions and hence were considered viable candidates.

Of the potential candidates, FadB, the second member of the FadBA multienzyme complex, is the most studied and has been shown to possess both hydroxyacyl-CoA dehydrogenase and enoyl-CoA hydratase activity with broad chain-length specificity[17,18]. Considering both of these activities are required for a functional reversal of the β-oxidation cycle and multiple cycle turns would require enzymes able to act on intermediates of varying carbon length, these key traits of FadB make it a promising candidate for in vitro characterization. As seen in Table 1, upon purification, FadB exhibits efficient 3-hydroxyacyl-CoA dehydrogenase activity for the NADH dependent reduction of acetoacetyl-CoA with a $k_{cat}/K_M$ of $6.65 \times 10^4$ $M^{-1}$ $s^{-1}$, providing initial evidence towards its inclusion as a member of the integrated set of components.

Enoyl-CoA Hydratase

Three members of the enoyl-CoA hydratase family involved in β-oxidation reactions should be able to act as 3-hydroxybutyryl-CoA dehydratase: aerobic (fadB) and anaerobic (fadJ) enoyl-CoA hydratases that participate in the β-oxidation of fatty acids[11], and a 2,3-dehydroadipyl-CoA hydratase (paaF) involved in phenylacetate degradation[16]. Despite the primary role of these enzymes in degradative pathways, the reversible nature of the reactions they catalyze indicates their potential for the dehydration of hydroxyacyl-CoAs.

With the previous selection of FadB as the 3-hydroxybutyryl-CoA dehydrogenase component of a one-turn reversal of the β-oxidation cycle, this protein represents the natural choice for an enoyl-CoA hydratase β-hydroxybutyryl-CoA dehydratase in the context of a one turn reversal), as it is reported to encode both hydroxyacyl-CoA dehydrogenase and enoyl-CoA hydratase activities[17,18]. The selection of this enzyme would also provide the advantage of minimizing the number of required components of the integrated framework.

As with 3-hydroxybutyryl-CoA dehydrogenase activity, the kinetic properties of purified FadB for 3-hydroxybutyryl-CoA dehydratase activity were evaluated (Table 1), and provided ample evidence for the ability of FadB to serve as the enoyl-CoA hydratase component in the modular framework. Although substrate saturation proved difficult, FadB did exhibit the required activity with an estimated (See Methods) $k_{cat}/K_M$ of $3.19 \times 10^3$ $M^{-1}s^{-1}$ for the hydration of crotonyl-CoA, demonstrating its potential to function as a key component during the in vivo assembly of a functional reversal of the β-oxidation cycle.

Acyl-CoA Dehydrogenase/Trans-Enoyl-CoA Reductase

Two β-oxidation enzymes were chosen as enzymes that can potentially catalyze the last step of the reversal of the cycle: an acyl-CoA dehydrogenase (fadE), involved in the aerobic catabolism of fatty acids[11] and a predicted acyl-CoA dehydrogenase (ydiO) proposed to be part of the β-oxidation of fatty acids under anaerobic conditions[19].

While there is evidence of YdiO[8] and FadE[20] playing roles in the reduction of crotonoyl-CoA to butyryl-CoA under certain conditions, the complexity of these enzymes make their in vitro characterization and in vivo assembly/function difficult. YdiO shares high homology with the crotonobetainyl-CoA reductase CaiA[8], an enzyme that catalyzes the reduction of crotonobetainyl-CoA to γ-butyrobetainyl-CoA[21], a reaction similar to the reduction of crotonyl-CoA to butyryl-CoA in the one-turn reversal of the β-oxidation cycle. Moreover, the fixABCX operon encoding flavoproteins and a ferredoxin required for the transfer of electrons to CaiA[22, 23] shows a high sequence similarity to those encoded by the ydiQRST operon[8].

This suggests that as with CaiA, YdiO requires auxiliary flavoproteins and a ferredoxin for the transfer of electrons during the reduction of enoyl-CoA to acyl-CoA making their modular assembly and in vivo function complicated. A further caveat for the use of these enzymes is the involvement of a ferredoxin, which is oxidized during electron transfer. Reduced ferredoxin would have to be regenerated with an additional reaction to enable continued turnover of electron transfer and hence the entire functional reversal of the β-oxidation cycle. For this purpose, a predicted pyruvate:flavodoxin oxidoreductase (ydbK)[24] could be utilized to couple pyruvate dissimilation with ferredoxin reduction, thus enabling the continued ferredoxin-aided electron transfer to the enoyl-CoA reduction step.

While the acyl-CoA dehydrogenase FadE does not catalyze a ferredoxin mediated reduction, the operation of this enzyme in its physiological direction (i.e. catabolism of fatty acids) is coupled to the electron transfer chain by flavoproteins and is thought to represent the only irreversible step in the catabolic operation of the β-oxidation cycle[11]. This direct coupling to the electron transfer chain with the use of FadE makes an overall one-turn functional reversal of the β-oxidation cycle unfavorable from a standard thermodynamic sense[8]. Although an electron transfer system similar to that of YdiO could be compatible with FadE, making the reaction more thermodynamically favorable, this adds a similar level of complexity to that described above for YdiO.

Given the aforementioned complexities of YdiO and FadE, we faced significant challenges during their in vitro purification and characterization. Upon purification, no detectable activities were measured with either enzyme, although we were able to measure their activities in crude extract of cells expressing them (Table 1). These results could reflect the requirement for auxiliary enzymes for proper function and underlie the potential challenges for their use as a key component in the modular framework.

To address these issues, we used a trans-2-enoyl-CoA reductase from the photosynthetic flagellate *Euglena gracilis* (egTER), shown to reduce the double bond in C4 and C6 enoyl-CoA intermediates to produce acyl-CoA via a NAD(P)H dependent mechanism[25]. This approach eliminates the requirement for auxiliary and coupling enzymes for proper function.

Interestingly, egTER is a key enzyme of an anaerobic metabolic process in the mitochondrion of *E. gracilis* that leads to the synthesis of wax esters via the malonyl-CoA-independent synthesis of fatty acids (the latter a process equivalent to a functional reversal of the β-oxidation cycle)[26]. This mitochondrial process synthesizes products of chain length 8-18, suggesting the ability of egTER to catalyze reduction of enoyl-CoA molecules of various chain lengths[26, 27]. Considering the physiological role of egTER as a functional unit of a core process similar to the reversal of the β-oxidation cycle and its broad chain-length specificity, the inclusion of this enzyme in our design holds great promise. Purification and in vitro characterization of egTER further demonstrated the validity of this enzyme as the reduction of crotonyl-CoA with NADH as a co-factor proceeded efficiently with a $k_{cat}/K_M$ of $1.16 \times 10^4$ $M^{-1}s^{-1}$ (Table 1).

Termination: Thioesterases

The combination of the four steps described above entail the functional units that form a reversal of the β-oxidation cycle. However, product synthesis from this process requires the use of termination pathways capable of converting the CoA intermediates of the core pathway to desired products. While a wide array of products with varying functionalities can be synthesized from the cycle intermediates through the selection and integration of various termination pathways[8], the use of thioesterases provides arguably the simplest termination pathway for the in vivo characterization of a functional one-turn reversal and also enables the assessment of each functional unit as the pathway is sequentially built. Thioesterases, part of the larger sub-family of hydrolase enzymes acting on ester bonds, catalyze the hydrolytic cleavage of thioester bonds. In the context of the functional reversal of the β-oxidation cycle, thioesterases cleave the thioester bond of the CoA intermediates converting them to their carboxylic acid components.

*E. coli* thioesterases encoded by tesA[28], tesB[29], yciA[30], fadM[31], ydiI[32], and ybgC[32] were selected for further characterization and integration with the framework of the in vivo assembly due to their varying substrate specificities. In vitro characterization through specific activity measurements of crude cell extract of strains expressing these various thioesterases showed YciA has the highest activity on 4-C CoA intermediates of the cycle (Table 2). However, each of the tested thioesterases showed increased activity with the longer chain intermediate decanoyl-CoA (Table 2).

While the high activity of YciA for the relevant 4 carbon CoA intermediates is promising, one possible issue revealed in this characterization is the fact that YciA also appears to have significant activity toward acetyl-CoA (Table 2), which could result in competition between the cycle initiation (thiolase) and the termination pathway in this case. This was confirmed through a full kinetic characterization of YciA, as the $K_M$ for acetyl-CoA (42.7 µM) was significantly lower than the $K_M$ for acetyl-CoA of AtoB (892 µM) (Table 1). In addition, this analysis revealed that YciA exhibits significant catalytic efficiency for all potential CoA intermediates during a one turn reversal of the β-oxidation cycle (Table 1), suggesting its ability to serve as the termination pathway from any CoA intermediate during the integrated assembly of the modules. However, given the low $K_M$ and high catalytic efficiency of YciA for acetyl-CoA, overexpression of this enzyme could also limit the flux into the core pathway during the in vivo assembly of a functional reversal of the β-oxidation cycle, and thus the testing of all selected thioesterase components is required to determine optimal functionality.

Assembly of Functional Units

While the in vitro characterization of selected components provides evidence of the ability of these enzymes to perform the reactions required for a functional reversal of the β-oxidation cycle, only the in vivo assembly of these individual units in conjunction with selected thioesterases as termination pathways can provide an assessment of pathway functionality (i.e. synthesis of 4-C carboxylic acids) (FIG. 8). This type of synthetic/bottom-up approach also ensures that each pre-defined component or building block (i.e. each functional unit/enzyme composing the pathway) can be individually integrated enabling a true assessment of the role and functionality of each step in a one-turn reversal of the core pathway.

However, before this can be achieved, the metabolism of the host organism (e.g. *E. coli* for our purposes) must be re-programmed to ensure that the expression of the individual components of the core and termination pathways leads to the desired biochemical product(s). Considering glycerol as the carbon source of interest, this requires shifting *E. coli* metabolism away from native fermentation products (FIG. 9A) and ensuring the generation of acetyl-CoA to serve as the priming molecule of the core pathway (FIG. 8).

To this end, a strain containing deletions of genes encoding enzymes responsible for fermentative routes to ethanol (adhE), acetate (pta and poxB), lactate (ldhA), and succinate (frdA) was constructed. As a result of these key gene deletions, glycerol metabolism was shifted from a mixture of lactate, acetate, and ethanol to a mixture of pyruvate and acetate in the engineered host (MG1655 ΔldhAΔpoxBΔptaΔadhEΔfrdA=JC01) (FIG. 9A). This product profile indicates that metabolism within the engineered host/chassis is adequately tailored for the synthesis of the desired 4-C carboxylic acids from the core pathway, as both the production of pyruvate and acetate reflect the build-up of the acetyl-CoA pool (FIG. 8). As such, the expression of a thiolase with high specificity for short-chain acyl-CoA compounds (i.e. AtoB) within this host should provide an additional outlet for acetyl-CoA, serving as the initial priming step of the core pathway and enabling the in vivo assessment of the individual components required for a functional reversal of the β-oxidation cycle.

As expected, the individual overexpression of atoB in JC01 resulted in the production of 4-C carboxylic acids (FIG. 9A) demonstrating that AtoB can serve to initiate the cycle under these conditions as well as indicating that natively expressed thioesterase(s) are present to serve as the termination pathway for the initial in vivo assessment of the cycle.

However, somewhat unexpected was the distribution of 4-C carboxylic acid products resulting from atoB expression. 3-oxobutyrate, the carboxylic acid product of thiol cleavage of acetoacetyl-CoA, was only present in small amounts, while the majority of the 4-C carboxylic acid production was in the form of 3-hydroxybutyrate, the thioesterase cleavage product of 3-hydroxybutyryl-CoA (FIG. 9B). This result probably indicates that the natively expressed thioesterase(s) under these conditions could have a very low specificity for acetoacetyl-CoA and/or the accumulation of acetoacetyl-CoA prompts its reduction to 3-hydroxybutyryl-CoA through the action of a native 3-ketobutyryl-CoA dehydrogenase (FIG. 8).

In order to investigate these possibilities and provide further assessment of selected termination pathway enzymes, strains were constructed in which atoB overexpression was combined with either overexpression of a thioesterase (tesA, tesB, yciA, fadM, ydiI, ybgC) or their deletion from the chromosome of the host strain. While no clear indication of a key thioesterase for 3-oxobutyrate production was determined, as no single overexpression significantly increased or single deletion unambiguously abolished 3-oxobutyrate (FIG. 10A-B), several notable aspects are seen. First, while the expression of ybgC does not yield an increase in 3-oxobutyrate, acetone production is observed in this strain (FIG. 10A). Acetone, a highly volatile short-chain methyl ketone, can be formed from the spontaneous decarboxylation of 3-oxobutyrate under appropriate conditions[33]. Secondly, and perhaps most notable, is the fact that overexpression of yciA leads to the elimination of all 4-C carboxylic acid products of the core pathway and resulted in a nearly 3-fold increase in the production of acetate (FIG. 10A).

While the results of the in vitro analysis of YciA indicated that this thioesterase can act on the majority of pathway intermediates seen from a one-turn reversal of the β-oxidation cycle (Table 1), the large increase in acetate reinforces the conclusion from in vitro characterization that the lower $K_M$ and greater catalytic efficiency (Table 1) allows YciA to favorably compete with AtoB for acetyl-CoA when overexpressed at significant levels. In addition, the reversible nature of AtoB (Table 1) and lack of an individually expressed 3-ketobutyryl-CoA dehydrogenase to act on acetoacetyl-CoA (FIG. 8) could also underlie the increased acetate production upon yciA overexpression. This also indicates that the overall control of product formation in the case of the expression of individual components may lie within the core pathway as opposed to the termination pathway.

The latter scenario is reflected by the fact that significant amounts of 3-hydrobutyrate are observed upon atoB expression (FIG. 9B), even in the lack of independent expression of a 3-ketobutyryl-CoA dehydrogenase. This result also provides a means of further assessing native FadB function as 3-ketobutyryl-CoA dehydrogenase during a reversal of the β-oxidation cycle. For this purpose, the fadB gene was deleted from the host strain and 4-C carboxylic acid production tested upon overexpression of atoB (i.e. JC01 ΔfadB pTHatoB pZSBlank).

As seen in FIG. 10B, the deletion of fadB led to a ~1.5-fold decrease in 3-hydrobutyrate production when compared to JC01 pTHatoB pZSBlank, reflecting a significant role of natively expressed fadB in the conversion of acetoacetyl-CoA to 3-hydrobutyryl-CoA. However, the deletion of fadB did not completely abolish 3-hydrobutyrate production indicating that other enzymes could be playing a role in this conversion. As previously mentioned, possible candidates include an anaerobic hydroxyacyl-CoA dehydrogenase (fadJ) and a 3-hydroxyadipyl-CoA dehydrogenase (paaH), with the latter showing moderate specific activity toward the reduction of acetoacetyl-CoA when the purified enzyme was tested (data not shown). While these results provide an intriguing area for further assessment of enzymes capable of catalyzing this reaction, both the in vitro characterization and the role of FadB upon atoB overexpression reflect the potential for this enzyme to serve as a key functional unit of the reversal of the β-oxidation cycle.

In order to further assess FadB and integrate the 3-hydroxyacyl-CoA dehydrogenase and enoyl-CoA hydratase components into the modular framework, a controllable construct for both atoB and fadB expression (i.e. pTHatoB-.fadB) was assembled and tested in vivo for 4-C carboxylic acid production. Further demonstrating the ability for this enzyme to serve as a key component of the reversal of the β-oxidation cycle, the combined overexpression of atoB and fadB in JC01 lead to a 3-fold increase in 3-hydroxybutyrate production compared to atoB expression only, with 2.5 g/L of 3-hydroxybutyrate produced at a yield of 0.29 g/g (FIGS. 11A-B).

Interestingly, despite the fact the in vitro characterization of FadB (Table 1) indicates that this enzyme can serve as both a 3-ketobutyryl-CoA dehydrogenase and 3-hydroxybutyryl-CoA dehydratase during the reversal of the β-oxidation cycle, only increases to 3-hydroxybutyrate production were observed upon its expression with atoB, with no detectable crotonate, the thiol cleavage product of crotonoyl-CoA (FIG. 8) observed. This is likely a result of the specificity of the native thioesterase(s) active under these conditions rather than a reflection of the in vivo ability for FadB to perform the dehydration reaction, as small amounts of butyrate, requiring the reduction and subsequent thioesterase cleavage of crotonoyl-CoA (FIG. 8), are also seen with this strain (FIG. 11A).

This was further assessed through the combined expression of atoB and fadB with either selected thioesterase individual overexpression (FIG. 11A) or deletion (FIG. 11B). While no increases to 3-hydroxybutyrate were observed upon the overexpression of selected thioesterases, the overexpression of ydiI in conjunction with atoB and fadB resulted in the production of small amounts of crotonate (~0.2 g/L, FIG. 11A), suggesting the ability for this enzyme to serve as a termination pathway for crotonate production and further confirming the ability for FadB to catalyze both the first reduction and subsequent dehydration reactions of the cycle. Also of note is the fact that despite the high specific activities and catalytic efficiency of YciA for 3-hydroxybutyryl-CoA and crotonoyl-CoA (Table 1), the combined overexpression of yciA with atoB and fadB results in increased acetate production with complete elimination of 4-C carboxylic acid pathway products (FIG. 11A), mirroring the results upon yciA overexpression with atoB only (FIG. 10A).

These results again underlie the importance of placing the main level of control over product formation on the individual steps expressed from the core pathway and supplementing this structure with highly specific termination pathways leading to specific product formation (such as the case of ydiI expression and crotonate formation). The promiscuity of the selected thioesterases, specifically YciA, for multiple pathway intermediates (Table 1) as well as the competition for intermediates between enzymes within the core pathway and termination pathways creates an intricate balance between the expression levels of key enzymes.

For the purposes of 4-C carboxylic acid production, it appears to be better to utilize native host termination pathway(s) as a means of complementing the manipulation of the individual functional units of the core pathway as the overall control strategy for the synthesis of different products.

For the case of 3-hydroxybutyrate formation in *E. coli*, select thioesterase deletion in conjunction with atoB and fadB expression indicate that while native expression of tesB and yciA may play a role in its production, as evidenced by the slight decreases in production levels (FIG. 11B), no single native termination pathway from the selected thioesterases is solely responsible for 3-hydroxybutyrate production.

Further evidence to the control over product formation that the core pathway exerts is seen from the presence of butyrate when atoB and fadB are individually expressed (even in conjunction with selected thioesterases other than the aforementioned yciA, FIG. 11A). Similar to the production of 3-hydroxybutyrate with thiolase expression only, the production of butyrate upon the expression of atoB and fadB would require the native expression of enzymes capable of catalyzing core pathway reactions, specifically the presence of a butyryl-CoA dehydrogenase required for the reduction of crotonyl-CoA to butyryl-CoA (FIG. 8).

In an attempt to elucidate the native enzymes involved in this conversion, gene deletions of candidates, including an acyl-CoA dehydrogenase (fadE) and a predicted acyl-CoA dehydrogenase (ydiO), were singularly added to JC01 and tested in combination with the expression of atoB and fadB (FIG. 12). While no single deletion resulted in the complete elimination of butyrate production, the deletion of ydiO resulted in a ~30% decrease in butyrate concentration indicating a possible role for this predicted acyl-CoA dehydrogenase (FIG. 12).

To gain further insight to the possible role and ability of these enzymes to serve as a key component of a functional reversal of the β-oxidation cycle, constructs that enable the combined overexpression of fadE or ydiO in conjunction with the thiolase (AtoB), 3-hydroxyacyl-CoA dehydrogenase (FadB), and enoyl-CoA hydratase components (FadB) were developed (i.e. pTHatoB.fadB.fadE and pTHatoB.fadB.ydiO). It is also important to note that for the case of ydiO expression, a vector containing the predicted auxiliary enzymes required for proper enzyme/pathway function (See above) was also constructed (i.e. pZSydbK.ydiQRST) and tested with the aforementioned construct in the presence of 1 mM thiamine pyrophosphate (TPP), shown to increase YdbK activity[24]. As seen in FIG. 12, while the expression of ydiO, even with the co-expression of auxiliary enzymes, showed no increase in butyrate production over atoB and fadB expression only, the expression of fadE with the first two enzymes of the core pathway resulted in a ~60% increase in butyrate levels showing the ability of this enzyme to contribute during the reversal of the β-oxidation cycle. While these results indicate a role for YdiO and FadE, the low levels of butyrate and high levels of 3-hydroxybutyrate production by these strains reflect the complexities involved with the use of these enzyme systems (e.g. requirement for additional auxiliary enzymes and coupling partners such as YdbK and YdiQRST) (see above).

As previously discussed, an alternative component for this step is the use of the trans-2-enoyl-CoA reductase from *E. gracilis* (egTER), which not only shows favorable kinetic characteristics for the reduction of crotonyl-CoA (Table 1), but is also from an organism which has been shown to possess a metabolic process (synthesis of waxes) whose core pathway is essentially equivalent to a functional reversal of the β-oxidation cycle[26]. One advantage of this enzyme is that egTER does not require auxiliary enzymes or coupling reactions for proper function as NAD(P)H is used as the electron donor in the reaction[25].

While the lack of a requirement for auxiliary enzymes could help the efficiency of this enzyme when used with a variety of carbon sources, in the case of glycerol, the fact that NADH is used as the reducing equivalent also confers an advantage for the production of reduced compounds that can be achieved from the intermediates of the cycle. The reduced nature of glycerol dictates that the formation of one molecule of pyruvate generates twice the number of reducing equivalents (2 NADH) as that from glucose[34], representing the exact number of reducing equivalents required for each "turn" of the cycle (i.e. two reduction reactions from the ketoacyl-CoA to the acyl-CoA intermediate, FIG. 8). In contrast to the use of YdiO, which requires the re-generation of a reduced ferredoxin during pyruvate dissimilation due to the nature of the electron donor for these enzymes, the fact that egTER utilizes NADH results in the ability to use this enzyme in conjunction with pyruvate dissimilation through pyruvate formate lyase to avoid the accumulation of additional reducing equivalents.

Given these distinct advantages of egTER compared to other candidate butyryl-CoA dehydrogenases, we investigated the impact of the combined expression of atoB, fadB, and egTER, encoding all components required in the modular framework for an efficient one turn reversal of the β-oxidation cycle. As seen in FIG. 12, in stark contrast to the expression of either fadE or ydiO, the expression of egTER along with atoB and fadB resulted in significant butyrate levels (3.43 g/L at a yield of 0.35 g/g produced). In addition, no 3-hydroxybutyrate was produced by this strain (FIG. 12) showing both the efficiency of egTER for this reduction reaction, as well as further demonstrating the ability of the core pathway components to dictate product formation during a one-turn reversal of the β-oxidation cycle.

Additional confirmation to this second point was provided through the expression of the key components required for a full one-turn reversal in conjunction with individual thioesterase overexpression in the host strain. No significant increase in butyrate production was observed upon overexpression of any of the thioesterases (FIG. 13A), despite moderate specific activities for butyryl-CoA (Table 2). However, while yciA expression led to significant increases in acetate production, its expression did not completely eliminate 4-C carboxylic acid production as it had with atoB or atoB/fadB expression only (FIG. 13A). This likely reflects the strong driving force to butyryl-CoA synthesis the expression of egTER dictates (i.e. core pathway expression controlling overall product formation), in combination with the high catalytic efficiency and specific activity for butyryl-CoA YciA shows compared to other 4-C CoA intermediates (Table 1), thus minimizing the impact of YciA activity on acetyl-CoA. Also of note is the fact the ybgC expression, which had not previously shown an impact on 4-C carboxylic acid production, resulted in a significant decrease in butyrate concentration in this instance.

While the modular expression of the individual components of a functional reversal of the β-oxidation cycle appears to exert the most control over the products produced with thioesterase termination pathways, the subsequent deletion of native thioesterases in JC01 with atoB, fadB, and egTER expression does provide valuable insight into the identity of the native termination pathway to butyrate. Despite the ambiguous nature of thioesterase deletion with partial β-oxidation cycle component expression, for a full one-turn cycle reversal YciA appears to be the most critical thioesterase for butyrate production as the deletion of yciA resulted in a near 5-fold decrease in butyrate concentration and yield (FIG. 13B).

These results agree with the high catalytic efficiency observed for YciA when butyryl-CoA is used as a substrate compared to other 4-C CoA intermediates (Table 1) and the fact that no other thioesterase tested has near the levels of specific activity on butyryl-CoA as YciA (Table 2). Despite the fact that YciA appears critical for butyrate production and also exhibits high activity for all pathway intermediates of a one-turn reversal (Table 1), its overexpression actually resulted in a decrease in 4-C carboxylic acid product formation when combined with the expression of individual core pathway enzymes due to the promiscuous nature of this thioesterase for a broad range of substrates[30].

Overall, the in vivo assembly of the individual components of the cycle with 4-C carboxylic acids as the proxy for product synthesis demonstrated what functional units are required for the effective functioning of the pathway. This enabled the construction of a fully synthetic and transferable system for the core components of a one-turn reversal the β-oxidation cycle. With this in place, the determination of the key requirements and components needed to extend the core pathway for multiple turns can be assessed, thus expanding the scope of products that can be synthesized through a functional reversal of the β-oxidation cycle.

Longer-Chain Products

The operation of multiple turns of a reversal of the β-oxidation cycle requires the condensation of the acyl-CoA generated from a turn(s) of the cycle with an additional acetyl-CoA molecule to lengthen the acyl-CoA by 2 carbons each cycle turn (e.g. condensation of butyryl-CoA with acetyl-CoA in FIG. 8)[8]. Thus, the initiation and extension of multiple cycle turns requires the use of a thiolase(s) with specificity for longer chain acyl-CoA molecules combined with other core pathway enzymes capable of acting on intermediates of increasing carbon number. While the selection and functionality of E. coli FadB and egTER from E. gracilis for a one turn reversal of the β-oxidation cycle demonstrated the reversible nature and capability of these enzymes, another advantage of their selection is the fact that they have been shown to participate in metabolic processes involving intermediates of various chain lengths and hence should have the ability to act on a broad range of carbon length intermediates (see above).

Therefore, with the current module enabling a functional reversal of the β-oxidation cycle, the key step controlling the ability to operate multiple turns of cycle lies with the thiolase selected for the condensation of acyl-CoA intermediates. While AtoB was chosen for a one-turn reversal due to its higher specificity for short-chain acyl-CoA molecules[12, 13], this trait may limit its ability to operate for continued turns of the cycle involving increasing carbon length intermediates.

On the other hand, FadA exhibits broad chain-length specificity for acyl-CoA substrates[14], making this enzyme an ideal candidate to support multiple cycle turns and enabling the production of longer chain products. However, the low efficiency of FadA with acetyl-CoA as a substrate (Table 1) likely requires the presence of another thiolase with higher specificity for short-chain acyl-CoA molecules (such as AtoB) to perform the initial condensation reaction (i.e. priming of the cycle).

Utilizing these components, a platform for the operation of multiple turns of a functional reversal of the β-oxidation cycle was developed through the modular construction of vectors encoding AtoB, the FadBA operon, and egTER. When integrated in the host strain JC01, this design enabled synthesis of extracellular longer chain fatty acids up to C12 (dodecanoic acid) through the native expression of thioesterase termination pathways (FIG. 14).

The expression of fadA was important for this purpose, as the same integrated components produced significantly less total longer chain fatty acids (C≥6) in the absence of FadA, and no products greater than C6 were detected (FIG. 14). In addition, 5-times the amount of butyrate was observed when FadA was excluded as a modular component, indicating the difficulty for AtoB to efficiently operate multiple cycle turns (and the ability of FadA to outcompete termination at butyrate).

Representative expression vectors constructed for the engineering of the β-oxidation reversal to use the different primers and termination pathways outlined in FIG. 16A-G.

While this modular framework demonstrates the required components for the operation of multiple cycle turns during a functional reversal of the β-oxidation cycle, the overall low levels of longer chain fatty acids demonstrate the opportunity for future investigation into the overall integration of the core pathway components as well as the identification and incorporation of highly specific termination pathways enabling the production of a wide array of products with varying carbon length and functionality.

Conclusions

An engineered reversal of the β-oxidation cycle was constructed using a synthetic/bottom-up approach based on the in vitro kinetic characterization of individual functional units and their in vivo assembly. This strategy enabled the synthesis of a variety of 4-C carboxylic acids resulting from a one-turn functional reversal of the β-oxidation cycle, as the individual thiolase (AtoB), 3-hydroxyacyl-CoA dehydrogenase (FadB), enoyl-CoA hydratase (FadB), and acyl-CoA dehydrogenase/trans-enoyl-CoA reductase (egTER) components exerted the majority of the control over product formation with native thioesterase termination pathways.

Through the integration of a thiolase capable of acting on longer chain intermediates (FadA), the initiation of multiple cycle turns leading to the production of longer chain products was also demonstrated.

This modular framework for the synthesis of 4-C and higher compounds overcomes some limitations with the previously used system-level/top-down approach (due to the ill-defined nature of the individual components of the pathway), providing a "clean" platform that can be transferred to other hosts/organisms. The self-contained and host-independent functional units identified in this study provide the core metabolic platform required for the efficient production of a wide array of compounds attainable from key intermediates of the reversal of the β-oxidation cycle. Further identification and integration of selective termination pathways should provide the required functionality to expand the portfolio of components.

This combined with further optimization, should enable the integration of this pathway within other industrial hosts allowing the advantageous nature of a reversal of the β-oxidation cycle to be fully exploited for the synthesis of a wide array of drop-in biofuels and biochemicals.

It should be remembered that while butyrate and other simple fatty acids were chosen to exemplify a functional reverse pathway, these are to be considered exemplary only and many products can be made with the invention, such as those listed in Tables 3A-B.

Materials & Methods

Wild-type K12 *Escherichia coli* strain MG1655[35] was used as the host for all genetic modifications. Gene knockouts were introduced in MG1655 and its derivatives by P1 phage transduction[36, 37]. Single gene knockout mutants from the National BioResource Project (NIG, Japan)[38] were used as donors of specific mutations. All mutations were confirmed by polymerase chain reaction and the disruption of multiple genes in a common host was achieved as previously described[36]. All resulting strains used in this study are listed in Supplementary Table 51.

Gene overexpression was achieved by cloning the desired gene(s) in either low-copy (pZS[36]) or higher copy based vectors (pTrcHis2A, abbreviated pTH$_A$; Invitrogen, Carlsbad, Calif.) utilizing In-Fusion PCR cloning technology (Clontech Laboratories, Inc., Mountain View, Calif.). Cloning inserts were created via PCR of ORFs of interest from *E. coli* genomic DNA using the primers listed in Supplementary Table S2 with Phusion DNA polymerase under standard conditions described by the supplier (Thermo Scientific, Waltham, Mass.). Amplification of the trans-2-enoyl-CoA reductase gene from *E. gracilis* (egTER) was performed as above except using a plasmid harboring a codon-optimized egTER synthesized by GenScript (Piscataway, N.J.). When appropriate, a RBS was added via primer synthesis. Vector backbone was purified from *E. coli* cultures (Qiagen, Valencia, Calif.) and digested with the restriction enzymes listed in Supplementary Table S2 as according to the manufacturer (New England Biolabs, Ipswich, Mass.) to enable cloning. The resulting In-Fusion products were used to transform *E. coli* Stellar cells (Clontech Laboratories, Inc., Mountain View, Calif.) and positive clones confirmed by PCR, restriction digestion, and DNA sequencing.

All molecular biology techniques were performed with standard methods[37, 39] or by manufacturer protocol. Strains were kept in 32.5% glycerol stocks at −80° C. Plates were prepared using LB medium containing 1.5% agar, and appropriate antibiotics were included at the following concentrations: ampicillin (100 µg/mL), kanamycin (50 µg/mL), and chloramphenicol (34 µg/mL).

The minimal medium designed by Neidhardt et al.[40], with 100 mM MOPS and Na$_2$HPO$_4$ in place of K$_2$HPO$_4$, supplemented with 20 g/L glycerol, 10 g/L tryptone, 5 g/L yeast extract, 100 µM Feso$_4$, 5 mM calcium pantothenate, 1.48 mM Na$_2$HPO$_4$, 5 mM (NH$_4$)$_2$SO$_4$, and 30 mM NH$_4$Cl was used for all fermentations unless otherwise stated. Antibiotics (100 µg/mL ampicillin and 34 µg/mL chloramphenicol) and inducers (0.1 µM Isopropyl β-D-1-thiogalactopyranoside and 100 ng/mL anhydrotetracycline) were included when appropriate. All chemicals were obtained from Fisher Scientific Co. (Pittsburgh, Pa.) and Sigma-Aldrich Co. (St. Louis, Mo.).

Fermentations were conducted in 25 mL Pyrex Erlenmeyer flasks (narrow mouth/heavy duty rim, Corning Inc., Corning, N.Y.) filled with 20 mL of the above culture medium and sealed with foam plugs filling the necks. A single colony of the desired strain was cultivated overnight (14-16 hrs) in LB medium with appropriate antibiotics and used as the inoculum (1%) for all fermentations. After inoculation, flasks were incubated at 37° C. and 200 rpm in an NBS C24 Benchtop Incubator Shaker (New Brunswick Scientific Co., Inc., Edison, N.J.) until an optical density of ~0.3-0.5 was reached, at which point IPTG and anhydrotetracycline were added. Flasks were then incubated under the same conditions for 48 hrs post-induction unless otherwise stated.

Optical density was measured at 550 nm in a Thermo Spectronic Genesys 20 (Thermo Scientific, Waltham, Mass.) and used as an estimate of cell mass (1 O.D.$_{550}$=0.34 g dry weight/L)[41]. Identification of short chain (C≤4) metabolites was conducted through nuclear magnetic resonance (NMR) as previously described[8] while longer chain fatty acids were identified via gas chromatography-mass spectroscopy (GC-MS). Identification of fatty acids was performed on an Agilent 7890A GC system (Agilent Technologies, Santa Clara, Calif.), equipped with a 5975C inert XL mass selective detector (Agilent Technologies, Santa Clara, Calif.) and an Rxi-5Sil column (0.25 mm internal diameter, 0.10 µm film thickness, 30 m length; Restek, Bellefonte, Pa.), following the method: an initial temperature of 35° C. held for 1 min, 6° C./min to 200° C., 30° C./min to 270° C., held for 1 min. Extraction and derivatization procedures were as described below. Helium (2.6 mL/min, Matheson Tri-Gas, Longmont, Colo.) was used as the carrier gas. The injector and detector were maintained at 280° C. A 2 µL sample was injected using a 40:1 split ratio.

Quantification of glycerol and metabolic products in the culture supernatant was conducted through high-performance liquid chromatography (HPLC) and gas chromatography-flame ionization detection (GC-FID). The concentrations of glycerol, ethanol, and organic acids were determined via ion-exclusion HPLC using a Shimadzu Prominence SIL 20 system (Shimadzu Scientific Instruments, Inc., Columbia, Md.) equipped with an HPX-87H organic acid column (Bio-Rad, Hercules, Calif.) with operating conditions to optimize peak separation (0.3 ml/min flowrate, 30 mM H$_2$SO$_4$ mobile phase, column temperature 42° C.)[42].

Additional quantification of fatty acids (C4-C12) and fatty acid methyl esters (C14-C18) was carried out in a Varian CP-3800 gas chromatograph (Varian Associates, Inc., Palo Alto, Calif.), equipped with a flame ionization detector (GC-FID) and an HP-INNOWax capillary column (0.32 mm internal diameter, 0.50 µm film thickness, 30 m length; Agilent Technologies, Inc., Santa Clara, Calif.), following the method: 50° C. held for 3 min, 10° C./min to 250° C., and 250° C. held for 10 min. Helium (1.8 mL/min, Matheson Tri-Gas, Longmont, Colo.) was used as the carrier gas. The injector and detector were maintained at 220° C. and 275° C., respectively. A 1 µl sample was injected in splitless injection mode.

For the identification of fatty acids, supernatant aliquots of 2 mL were transferred to 5 mL glass vials (Fisher Scientific Co., Pittsburgh, Pa.). Samples were supplemented with 1.2 µL of 1-nonanol as internal standard, and extracted with 2 mL of hexane. Vials were tightly closed, vortexed for 30 s, and mixed in a Glas-Col rotator (Glas-Col, Terre Haute, Ind.) at 60 rpm for 2 hours. Samples were then vortexed again for 30 s and centrifuged at 8000 rpm at 4° C. for 1 min. Aliquots of 700 µL of the top organic layer were transferred to 2 mL borosilicate glass vials with PTFE/silicone screw caps (Fisher Scientific Co., Pittsburgh, Pa.) and mixed with 50 µL of pyridine and 50 µL of BSTFA (N,O-bis(trimethylsilyl)trifluoroacetamide). Samples were incubated in sealed vials at 70° C. for 30 min using an AccuBlock Digital Dry Bath (LabNet, Woodbridge, N.J.) and silylated samples were analyzed via GC-MS.

For the quantification of fatty acids and fatty acid methyl esters, supernatant aliquots of 2 mL were transferred to 5 mL glass vials (Fisher Scientific Co., Pittsburgh, Pa.). Samples were acidified with sulfuric acid, supplemented with 2 mg of tridecanoic acid as internal standard, and extracted with 2 mL of a mixture of hexane:chloroform (4:1, v/v). Vortex, rotation, and centrifugation were done as described above. For the quantification of short- and medium-chain fatty acids (C4-C12), 1 mL of the organic layer was aliquoted into 2 mL borosilicate glass vials with PTFE/silicone screw caps (Fisher Scientific Co., Pittsburgh, Pa.) and analyzed via GC-FID.

For the quantification of longer-chain fatty acids (C14-C18), 1 mL of the organic layer was transferred to 2 mL glass vials (Fisher Scientific Co., Pittsburgh, Pa.). Samples were nitrogen evaporated to near dryness, re-dissolved in 1 mL of a mixture of methanol:chloroform:sulfuric acid (30:3:1, v/v/v) and incubated in a sealed vial at 90° C. for 60 min using an AccuBlock Digital Dry Bath (LabNet, Woodbridge, N.J.). Water (1 mL) was added to each tube, and fatty acid methyl esters (FAMEs) were extracted with 2 mL of hexane:chloroform (4:1, v/v). After extraction, 1 mL of the organic layer was aliquoted into 2 mL borosilicate glass vials with PTFE/silicone screw caps (Fisher Scientific Co., Pittsburgh, Pa.) and analyzed via GC-FID.

Stearic ($C_{18:0}$), palmitic ($C_{16:0}$), myristic ($C_{14:0}$), lauric ($C_{12:0}$), capric ($C_{10:0}$), caprylic ($C_{8:0}$), caproic ($C_{6:0}$), and butyric ($C_{4:0}$) acids (Sigma Chemical Co., St. Louis, Mo.) were used to calibrate the gas chromatograph. Hexane (High Resolution Gas Chromatography grade) and chloroform (reagent grade) were used as extraction solvents (Fisher Scientific Co., Pittsburgh, Pa.). 1-Nonanol, pyridine (HPLC grade) and BSTFA (synthesis grade) were used for the silylation reaction (Sigma Chemical Co., St. Louis, Mo.). Methanol and concentrated sulfuric acid used for the esterification reaction were reagent grade (Fisher Scientific Co., Pittsburgh, Pa.).

When stated, product yields (mmol/mmol glycerol or g/g glycerol) represent the amount of product synthesized per amount of glycerol consumed during the length of the fermentation (48 hrs unless otherwise stated).

For enzyme characterization, E. coli fadA and fadB genes were cloned from MG1655 genomic DNA into the pUCBB-ntH6 vector[43] to yield a constitutively expressed gene with a n-terminal 6 His-tag that can be cleaved by Thrombin. fadA was amplified as two halves with the primers fadANdeI5p:fadAmidrev ($1^{st}$ half) and fadAmidfor:fadANotI3p ($2^{nd}$ half) (Supplementary Table S3).

fadB was amplified in three parts with fadBNdeI5p:fadBmid1rev ($1^{st}$ part), fadBmid1for:fadBmid2rev ($2^{nd}$ part), and fadBmid2for:fadBNotI3p ($3^{rd}$ part) (Supplementary Table S3). fadA and fadB PCR products sections were combined by overlap extension PCR to yield the whole genes, which were subsequently digested with NdeI and NotI restriction enzymes and ligated into pUCBB-ntH6 that was previously digested with NdeI and NotI to yield pUCBB-ntH6-FadA and pUCBB-ntH6-FadB.

The hbd gene from Clostridium acetobutylicum ATCC 824 (caHBD) was cloned into pUCBB-pBAD[43] to yield an arabinose inducible caHBD gene with a c-terminal $His_6$-tag. caHBD was PCR amplified from the genome of Clostridium acetobutylicum ATCC 824 using the caHBDBglii5p and caHBDxhoI3p primers (Supplementary Table S3). The resulting PCR product was then digested with BglII and XhoI and ligated into pUCBB-pBAD previously digested with BglII and XhoI to yield pUCBB-pBAD-caHBD.

For AtoB and thioesterase characterization assays, the pCA24N-gene (-gfp) plasmids from the ASKA collection[44] were used. For expression of E. gracilis TER for kinetic characterization, the egTER gene was cloned into pTrcHis2A using the In-Fusion protocol (Clontech Laboratories, Inc., Mountain View, Calif.) following PCR amplification from the aforementioned codon-optimized egTER containing plasmid with the primer pair of F1pTH6hisEgter and R1pTH6hisEgter (Supplementary Table S3).

Cultures for enzymatic assays were grown overnight in 100 mL of LB media at 37° C. in 250 mL baffled flasks (Wheaton Industries, Inc., Millville, N.J.) in E. coli BL21 (DE3) cells induced with either 1 mM IPTG (pCA24N, pTrcHis2A) or 1 mM Arabinose (pUCBB-pBAD) at an $OD_{600}$~0.6, or expressed constitutively (pUCBB-ntH6). Reactions were monitored on either a Synergy HT plate reader (BioTek Instruments, Inc., Winooski, Vt.) at 25° C. (for reactions monitored at 300 nm or higher) or in a Biomate 5 Spectrophotometer (Thermo Scientific, Waltham, Mass.) for reactions at 263 nm.

Cells were lysed using Bacterial Protein Extraction Reagent (B-PER) (Thermo Scientific, Waltham, Mass.) as per the prescribed protocol in order to obtain the supernatant containing the active enzymes. FadE and YdiO were purified following previously established methods[45] using the same growth conditions mentioned above.

Cell pellets were resuspended in 40 mL of 50 mM potassium phosphate buffer pH 7.2 and broken by disruption EmulsiFlex-05 homogenizer (Avestin, Ottawa, ON). Disrupted cells were then spun for 90 min at 4° C. at 120,000×g in a Optima L-80XP Ultracentrifuge (Beckman-Coulter, Schaumburg, Ill.) to produce the supernatant used for assays.

For specific activity assays (reported in µmol substrate/mg protein/min) these supernatant fractions were utilized and protein concentration was established using the Bradford Reagent (Thermo Scientific, Waltham, Mass.) using BSA as the protein standard. Linearity was established for each reaction and the background non-enzymatic rate was subtracted to establish the activity.

For kinetic characterization, his-tagged proteins of AtoB, FadA, FadB, caHBD, egTER were purified from the B-PER supernatant fractions using Talon Metal Affinity Resin (Clontech Laboratories, Inc., Mountain View, Calif.) using gravity purification. In short, the supernatant was mixed for 1 hr at room temperature on a LabQuake rotator (Fisher Scientific, Pittsburgh, Pa.) with approximately 2 mL of Talon Resin (1 resin/0.3 mg supernatant protein) that was pre-washed twice with Buffer A (50 mM Tris pH 7.9, 5 mM $MgCl_2$, 100 mM NaCl, 5 mM Imidazole). Resin was then spun at 700×g for 5 min to remove the non-bound proteins, washed with 20× (40 mL) Buffer A, resuspended in 20× (40 mL) Buffer B (Buffer A with 20 mM Imidazole) and loading onto a gravity column. Buffer B was then drained off and the protein was eluted with 20 mL of Buffer C (Buffer A with 250 mM Imidazole). The eluted fraction was then concentrated and used for kinetic characterizations. Enzyme concentration was established by measuring the absorbance at 260 nm and extinction coefficients predicted for each enzyme by the ProtParam program (web.expasy.org/protparam/).

For kinetic characterization, an appropriate amount of enzyme was established by checking linear range near predicted $K_M$ values. Then, the rates were measured for a range of substrates in order to establish $k_{cat}$ and $K_M$. In the cases of FadB for the crotonase reaction and FadA in the "forward" thiolase reaction coupled with HBD, substrate saturation could not be established, as such, the $k_{cat}/K_M$ for the reaction was determined by dividing the linear slope of Velocity vs. [Substrate] by the amount of enzyme used in the assays. For reactions that could be saturated, Velocity vs. [Substrate] was fitted by the EnzKIN Matlab module (mathworks.com/matlabcentral/fileexchange/26653) to establish $V_{max}$ and $K_M$.

The forward thiolase assay (i.e. biosynthetic direction) and β-hydroxybutyryl-CoA dehydrogenase assays were performed in the presence of 1.5 mM DTT, 4.5 mM $MgCl_2$, 100 mM Tris HCl pH 7.5 and 0.2 mM NADH in a total volume of 200 µL at 25° C.[46].

β-hydroxybutyryl-CoA dehydrogenase activity was monitored by following the oxidation of NADH at 340 nm while thiolase activity in the forward direction was measured at 340 nm in a coupled assay in which 10U excess of caHBD was present to reduce the acetoacetyl-CoA generated from thiolase activity.

Thiolase activity in the reverse direction was determined in the presence of 0.5 mM DTT, 4.5 mM $MgCl_2$, 100 mM Tris HCl pH 7.5 and 2 mM CoA in a total volume of 200 µL at 25° C.[47]. Activity was monitored by the loss of acetoacetyl-CoA at 303 nm using an extinction coefficient of 14 $mM^{-1}$ $cm^{-1}$. Crotonase activity was monitored by following the loss of crotonoyl-CoA at 263 nm ($\varepsilon$=6.7 $mM^{-1}$ $cm^{-1}$) in the presence of 100 mM Tris HCL pH 7.5 in 200 µL total volume.

For egTER, crotonyl-CoA reductase activity was followed by monitoring the loss of NADH absorbance in the presence of 100 mM Tris HCL pH 7.5 and 0.2 mM NADH in a final volume of 200 µL at 25° C.[46].

For FadE and YdiO, Butyryl-CoA dehydrogenase activity was measured utilizing ferricenium ion[49]. Reactions were performed in 50 mM potassium phosphate pH 7.2, 0.4 mM $MgSO_4$, 200 µM ferrocenium hexafluorophosphate, and 200 µM Butyryl-CoA and monitored the formation of the reduced ferrocene ion at 300 nm ($\varepsilon$=4.3 $mM^{-1}$ $cm^{-1}$).

Thioesterase activity was monitored by following the production of TNB at 412 nm ($\varepsilon$=4.3 $mM^{-1}$ $cm^{-1}$)[30]. Reactions were carried out in the presence of 100 mM Tris pH 7.5, 200 mM KCl, 25 mM DTNB and 200 µM of the '-CoA' substrate in a volume of 200 µL at 25° C.

All substrates and chemicals for enzyme assays were obtained from Fisher Scientific Co. (Pittsburgh, Pa.) and Sigma-Aldrich Co. (St. Louis, Mo.).

Below are the Tables:

TABLE 1 in vitro kinetic characterization of enzymes involved in a functional reversal of the β-oxidation cycle.

| Protein | Substrate | $k_{cat}$ ($s^{-1}$) | $K_M$ (µM) | $k_{cat}/K_M$ ($M^{-1}$ $s^{-1}$) | Specific Activity (µmol/mg/min) |
|---|---|---|---|---|---|
| AtoB | Acetyl-CoA | 3.17 ± 0.18 | 892.0 ± 56.5 | $3.55 \times 10^3$ | 0.919 ± 0.002[b] |
|  | Acetoacetyl-CoA | 9.23 ± 0.34 | 68.1 ± 2.56 | $1.36 \times 10^5$ | 0.36 ± 0.05[b] |
| FadA | Acetyl-CoA |  |  | 7.47[a] | Not detected[c] |
|  | Acetoacetyl-CoA | 0.75 ± 0.09 | 422.5 ± 57.3 | $1.77 \times 10^3$ | 0.013 ± 0.002[c] |
| FadB | Acetoacetyl-CoA | 25.9 ± 1.2 | 390.0 ± 19.2 | $6.65 \times 10^4$ | 0.185 ± 0.001[c] |
|  | Crotonyl-CoA |  |  | $3.19 \times 10^{3a}$ | 0.051 ± 0.004[c] |
| egTER | Crotonyl-CoA | 1.14 ± 0.08 | 98.5 ± 7.7 | $1.16 \times 10^4$ | 5.4 ± 0.6[d] |
| FadE | Butyryl-CoA |  |  |  | 0.008 ± 0.001[b] |
| YdiO | Butyryl-CoA |  |  |  | 0.009 ± 0.003[b] |
| YciA | Acetyl-CoA | 6.9 ± 0.1 | 42.7 ± 1.2 | $1.61 \times 10^5$ | 0.222 ± 0.007[b] |
|  | Acetoacetyl-CoA | 264.6 ± 54.7 | 875.7 ± 180.9 | $3.02 \times 10^5$ | 0.672 ± 0.007[b] |
|  | RS-3-Hydroxybutyryl-CoA | 32.4 ± 3.5 | 353.8 ± 38.8 | $9.15 \times 10^5$ | 0.441 ± 0.009[b] |
|  | Crotonyl-CoA | 46.4 ± 7.7 | 1348.8 ± 235.5 | $3.44 \times 10^5$ | 0.27 ± 0.03[b] |
|  | Butyryl-CoA | 557.5 ± 79.6 | 641.8 ± 91.9 | $8.69 \times 10^5$ | 2.9 ± 0.2[b] |

[a] could not be saturated
[b] expressed from pCA24N
[c] expressed from pUCBB-ntH6
[d] expressed from pTrcHis2A

TABLE 2

Specific activities of selected thioesterases on relevant CoA intermediates (µmol/mg protein/min)

| Protein[a] | Acetyl-CoA | Acetoacetyl-CoA | RS-3-Hydroxybutyryl-CoA | Crotonyl-CoA | Butyryl-CoA | Decanyl-CoA |
|---|---|---|---|---|---|---|
| FadM | 0.0331 ± 0.0006 | 0.042 ± 0.004 | 0.009 ± 0.002 | 0.0017 ± 0.0003 | 0.027 ± 0.001 | 0.034 ± 0.003 |
| TesA | 0.036 ± 0.002 | 0.044 ± 0.005 | 0.02 ± 0.01 | 0.007 ± 0.003 | 0.049 ± 0.002 | 0.47 ± 0.04 |

TABLE 2-continued

Specific activities of selected thioesterases on relevant CoA intermediates (μmol/mg protein/min)

| Protein[a] | Acetyl-CoA | Acetoacetyl-CoA | RS-3-Hydroxybutyryl-CoA | Crotonyl-CoA | Butyryl-CoA | Decanyl-CoA |
|---|---|---|---|---|---|---|
| TesB | 0.030 ± 0.001 | 0.056 ± 0.001 | 0.032 ± 0.002 | 0.010 ± 0.001 | 0.101 ± 0.002 | 0.6 ± 0.1 |
| YbgC | 0.036 ± 0.002 | 0.065 ± 0.002 | 0.016 ± 0.004 | 0.006 ± 0.001 | 0.045 ± 0.007 | 0.06 ± 0.02 |
| YciA | 0.222 ± 0.007 | 0.672 ± 0.007 | 0.441 ± 0.009 | 0.27 ± 0.03 | 2.9 ± 0.2 | 3.7 ± 0.3 |
| YdiI | 0.036 ± 0.003 | 0.047 ± 0.001 | 0.012 ± 0.002 | 0.078 ± 0.005 | 0.0917 ± 0.0007 | 0.18 ± 0.04 |

[a] genes encoding each protein expressed from pCA24N

TABLE 3A

Synthesis of functionalized carboxylic acids (dicarboxylic acids, hydroxy acids, aminated acids, branched chain acids) and their β-substituted derivatives via engineered reversal of the b-oxidation cycle by using functionalized primers and thioesterases as termination pathways.

| Primer | Genotype (mutations) | Product(s) |
|---|---|---|
| | ω-hydroxylated primers | |
| Hydroxyacetyl-CoA (glycolyl-CoA) | JC01 ΔfadB ΔfadJ ΔpaaH [THIL+ THIE+] | 4-hydroxy-3-oxo-butyric acid |
| | JC01 ΔfadE ΔydiO [THIL + fadB+ THIE+] | 3,4-dihydroxybutyric acid |
| | JC01 ΔfadE ΔydiO [THIL+ fadB+ THIE+] | 4-hydroxy-trans-$\Delta^2$-butyric acid |
| | JC01 [THIL+ fadB+ ydiO+ ydiQRST+ ydbK+ THIE+] | 4-hydroxybutyric acid |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo-n-hydroxy monocarboxylic acids, 3,n- |
| | JC01 [THIL+ fadBA+ fadE+ ydiQRST+ ydbK+ THIE+] | dihydroxy monocarboxylic acids, n-hydroxy, |
| | JC01 [THIL+ fadBA+ Ter+ THIE+] | trans-$\Delta^2$ monocarboxylic acids, n-hydroxy monocarboxylic acids (even chain lengths, C4-C16) |
| Hydroxypropionyl-CoA | JC01 ΔfadB ΔfadJ ΔpaaH [THIL+ THIE+] | 5-hydroxy-3-oxo-pentanoic acid |
| | JC01 ΔfadE ΔydiO [THIL + fadB+ THIE+] | 3,5-dihydroxy pentanoic acid |
| | JC01 ΔfadE ΔydiO [THIL+ fadB+ THIE+] | 5-hydroxy-trans-$\Delta^2$-pentanoic acid |
| | JC01 [THIL+ fadB+ ydiO+ ydiQRST+ ydbK+ THIE+] | 5-hydroxy pentanoic acid |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo-n-hydroxy monocarboxylic acids, 3,n- |
| | JC01 [THIL+ fadBA+ fadE+ ydiQRST+ ydbK+ THIE+] | hydroxy monocarboxylic acids, n-hydroxy, |
| | JC01 [THIL+ fadBA+ Ter+ THIE+] | trans-$\Delta^2$ monocarboxylic acids, n-hydroxy monocarboxylic acids (odd chain lengths, C5-C17) |
| Hydroxybutyryl-CoA | JC01 ΔfadB ΔfadJ ΔpaaH [THIL+ THIE+] | 6-hydroxy-3-oxo-hexanoic acid |
| | JC01 ΔfadE ΔydiO [THIL + fadB+ THIE+] | 3,6-dihydroxy hexanoic acid |
| | JC01 ΔfadE ΔydiO [THIL+ fadB+ THIE+] | 6-hydroxy-trans-$\Delta^2$-hexanoic acid |
| | JC01 [THIL+ fadB+ ydiO+ ydiQRST+ ydbK+ THIE+] | 6-hydroxy hexanoic acid |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo-n-hydroxy monocarboxylic acids, 3,n- |
| | JC01 [THIL+ fadBA+ fadE+ ydiQRST+ ydbK+ THIE+] | dihydroxy monocarboxylic acids, n-hydroxy, |
| | JC01 [THIL+ fadBA+ Ter+ THIE+] | trans-$\Delta^2$ monocarboxylic acids, n-hydroxy monocarboxylic acids (even chain lengths, C6-C18) |
| | ω-carboxylated primers | |
| Oxalyl-CoA | JC01 ΔfadB ΔfadJ ΔpaaH [THIL+ THIE+] | 3-oxo-succinic acid |
| | JC01 ΔfadE ΔydiO [THIL + fadB+ THIE+] | 3-hydroxy-succinic acid |
| | JC01 ΔfadE ΔydiO [THIL+ fadB+ THIE+] | trans-$\Delta^2$-butenedioic acid (fumaric acid) |
| | JC01 [THIL+ fadB+ ydiO+ ydiQRST+ ydbK+ THIE+] | butanedioic acid (succinic acid) |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo-dicarboxylic acids, 3-hydroxy dicarboxylic |
| | JC01 [THIL+ fadBA+ fadE+ ydiQRST+ ydbK+ THIE+] | acids, trans-$\Delta^2$ dicarboxylic acids, dicarboxylic |
| | JC01 [THIL+ fadBA+ Ter+ THIE+] | acids (even chain lengths, C4-C16) |
| Malonyl-CoA | JC01 ΔfadB ΔfadJ ΔpaaH [THIL+ THIE+] | 3-oxo-pentanedioic acid |
| | JC01 ΔfadE ΔydiO [THIL + fadB+ THIE+] | 3-hydroxy-pentanedioic acid |
| | JC01 ΔfadE ΔydiO [THIL+ fadB+ THIE+] | trans-$\Delta^2$-pentanedioic acid |
| | JC01 [THIL+ fadB+ ydiO+ ydiQRST+ ydbK+ THIE+] | pentanedioic acid (glutaric acid) |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo-dicarboxylic acids, 3-hydroxy dicarboxylic |
| | JC01 [THIL+ fadBA+ fadE+ ydiQRST+ ydbK+ THIE+] | acids, trans-$\Delta^2$ dicarboxylic acids, dicarboxylic |
| | JC01 [THIL+ fadBA+ Ter+ THIE+] | acids (odd chain lengths, C5-C17) |
| Succinyl-CoA | JC01 ΔfadB ΔfadJ ΔpaaH [THIL+ THIE+] | 3-oxo-hexanedioic acid |
| | JC01 ΔfadE ΔydiO [THIL + fadB+ THIE+] | 3-hydroxy-hexanedioic acid |
| | JC01 ΔfadE ΔydiO [THIL+ fadB+ THIE+] | trans-$\Delta^2$-hexanedioic acid |
| | JC01 [THIL+ fadB+ ydiO+ ydiQRST+ ydbK+ THIE+] | hexanedioic acid (adipic acid) |
| | JC01 [THIL+ fadB+ fadE+ ydiQRST+ ydbK+ THIE+] | |
| | JC01 [THIL+ fadB+ Ter+ THIE+] | |
| | JC01 [THIL+ fadBA+ ydiO+ ydiQRST+ ydbK+ THIE+] | 3-oxo dicarboxylic acids, n-hydroxy dicarboxylic |

TABLE 3A-continued

Synthesis of functionalized carboxylic acids (dicarboxylic acids, hydroxy acids, aminated acids, branched chain acids) and their β-substituted derivatives via engineered reversal of the b-oxidation cycle by using functionalized primers and thioesterases as termination pathways.

| Primer | Genotype (mutations) | Product(s) |
|---|---|---|
| | JC01 [THIL+ fadBA+ fadE+ ydiQRST+ ydbK+ THIE+]<br>JC01 [THIL+ fadBA+ Ter+ THIE+] | acids, trans-$\Delta^2$ dicarboxylic acids, dicarboxylic acids (even chain lengths, C6-C18) |
| | ω-aminated primers | |
| 2-aminoacetyl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 4-amino-3-oxo-butyric acid<br>4-amino-3-hydroxy-butyric acid<br>4-amino-trans-D$^2$-butyric acid<br>4-amino-butyric acid |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-n-amino monocarboxylic acids, 3-hydroxy-n-amino monocarboxylic acids, n-amino, trans-$\Delta^2$ monocarboxylic acids, n-amino monocarboxylic acids (even chain lengths, C4-C16) |
| 3-aminopropionyl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 5-amino-3-oxo-pentanoic acid<br>5-amino-3-hydroxy-pentanoic acid<br>5-amino-trans-D$^2$-pentanoic acid<br>5-amino-pentanoic acid |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-n-amino monocarboxylic acids, 3-hydroxy-n-amino monocarboxylic acids, n-amino, trans-$\Delta^2$ monocarboxylic acids, n-amino monocarboxylic acids (odd chain lengths, C5-C17) |
| 4-aminobutyryl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 6-amino-3-oxo-hexanoic acid<br>6-amino-3-hydroxy-hexanoic acid<br>6-amino-trans-D$^2$-hexanoic acid<br>6-amino-hexanoic acid (6-aminocaproic acid) |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-n-amino monocarboxylic acids, 3-hydroxy-n-amino monocarboxylic acids, n-amino, trans-$\Delta^2$ monocarboxylic acids, n-amino monocarboxylic acids (even chain lengths, C6-C18) |
| | non-terminal/secondary carbon functionalized primers | |
| Isobutyryl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 4-methyl-3-oxo-pentanoic acid<br>4-methyl-3-hydroxy-pentanoic acid<br>4-methyl-trans-D$^2$-pentanoic acid<br>4-methyl-pentanoic acid |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-(n-1)-methyl-monocarboxylic acids, 3-hydroxy-(n-1)-methyl-monocarboxylic acids, (n-1)-methyl-trans-$\Delta^2$ monocarboxylic acids, (n-1)-methyl-monocarboxylic acids (odd chain lengths, C5-C17) |
| 3-methyl-butyryl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 5-methyl-3-oxo-hexanoic acid<br>5-methyl-3-hydroxy-hexanoic acid<br>5-methyl-trans-D$^2$-hexanoic acid<br>5-methyl-hexanoic acid |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-(n-1)-methyl-monocarboxylic acids, 3-hydroxy-(n-1)-methyl-monocarboxylic acids, (n-1)-methyl-trans-$\Delta^2$ monocarboxylic acids, (n-1)-methyl-monocarboxylic acids (even chain lengths, C6-C18) |
| 2-hydroxypropionoyl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+]<br>JC01 [THIL+ fadB+ fadE+ ydiQRST+ ydbK+ THIE+]<br>JC01 [THIL+ fadB+ Ter+ THIE+] | 4-hydroxy-3-oxo-pentanoic acid<br>3,4-dihydroxy-pentanoic acid<br>4-hydroxy-trans-D$^2$-pentanoic acid<br>4-hydroxy-pentanoic acid |
| | JC01 [THIL+ fadBA+ ydiO+ ydiQRST+ ydbK+ THIE+]<br>JC01 [THIL+ fadBA+ fadE+ ydiQRST+ ydbK+ THIE+]<br>JC01 [THIL+ fadBA+ Ter+ THIE+] | 3-oxo-(n-1)-hydroxy-monocarboxylic acids, 3,(n-1)-dihydroxy-monocarboxylic acids, (n-1)-hydroxy-trans-$\Delta^2$ monocarboxylic acids, (n-1)-hydroxy-monocarboxylic acids (odd chain lengths, C5-C17) |
| 3-hydroxybutyryl-CoA | JC01 ΔfadB ΔfadJ ΔpaaH [THIL+ THIE+]<br>JC01 ΔfadE ΔydiO [THIL + fadB+ THIE+]<br>JC01 ΔfadE ΔydiO [THIL+ fadB+ THIE+]<br>JC01 [THIL+ fadB+ ydiO+ ydiQRST+ ydbK+ THIE+] | 5-hydroxy-3-oxo-hexanoic acid<br>3,5-dihydroxy-hexanoic acid<br>5-hydroxy-trans-D$^2$-hexanoic acid<br>5-hydroxy-hexanoic acid |

TABLE 3B

Synthesis of functionalized alcohols (hydroxy acids, triols, diols, aminated alcohols, branched chain alcohols) and their β-substituted derivatives via engineered reversal of the b-oxidation cycle by using functionalized primers and aldehyde-forming acyl-CoA reductases and alcohol dehydrogenases as termination pathways.

| Primer | Genotype (mutations) | Product(s) |
|---|---|---|
| ω-hydroxylated primers | | |
| Hydroxyacetyl-CoA (glycolyl-CoA) | JC01 ΔfadB ΔfadJ ΔpaaH [THIL+ ACR+ ADH+] | 1,4-dihydroxybutan-3-one |
| | JC01 ΔfadE ΔydiO [THIL + fadB+ ACR+ ADH+] | butane-1,3,4-triol |
| | JC01 ΔfadE ΔydiO [THIL+ fadB+ ACR+ ADH+] | trans-D$^2$-butene-1,4-diol |
| | JC01 [THIL+ fadB+ ydiO+ ydiQRST+ ydbK+ ACR+ ADH+] | butane-1,4-diol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | 3-oxo-1,n-diols, 1,3,n-triols, trans-Δ$^2$ 1,n-diols, 1,n-diols (even chain lengths, C4-C16) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| Hydroxypropionyl-CoA | JC01 ΔfadB ΔfadJ DpaaH [THIL+ ACR+ ADH+] | 1,5-dihydroxypentan-3-one |
| | JC01 ΔfadE ΔydiO [THIL + fadB+ ACR+ ADH+] | pentane-1,3,5-triol |
| | JC01 ΔfadE ΔydiO [THIL+ fadB+ ACR+ ADH+] | trans-D$^2$-pentane-1,5-diol |
| | JC01 [THIL+ fadB+ ydiO+ ydiQRST+ ydbK+ ACR+ ADH+] | pentane-1,5-diol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | 3-oxo-1,n-diols, 1,3,n-triols, trans-Δ$^2$ 1,n-diols, 1,n-diols (odd chain lengths, C5-C17) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| Hydroxybutyryl-CoA | JC01 ΔfadB ΔfadJ ΔpaaH [THIL+ ACR+ ADH+] | 1,6-dihydroxyhexan-3-one |
| | JC01 ΔfadE ΔydiO [THIL + fadB+ ACR+ ADH+] | hexane-1,3,6-triol |
| | JC01 ΔfadE ΔydiO [THIL+ fadB+ ACR+ ADH+] | trans-D$^2$-hexane-1,6-diol |
| | JC01 [THIL+ fadB+ ydiO+ ydiQRST+ ydbK+ ACR+ ADH+] | hexane-1,6-diol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | 3-oxo-1,n-diols, 1,3,n-triols, trans-Δ$^2$ 1,n-diols, 1,n-diols (even chain lengths, C6-C18) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| ω-carboxylated primers | | |
| Oxalyl-CoA | JC01 ΔfadB ΔfadJ ΔpaaH [THIL+ ACR+ ADH+] | 4-hydroxy-2-oxobutanoic acid |
| | JC01 ΔfadE ΔydiO [THIL + fadB+ ACR+ ADH+] | 2,4-dihydroxybutanoic acid |
| | JC01 ΔfadE ΔydiO [THIL+ fadB+ ACR+ ADH+] | (E)-4-hydroxy-but-2-enoic acid |
| | JC01 [THIL+ fadB+ ydiO+ ydiQRST+ ydbK+ ACR+ ADH+] | 4-hydroxybutanoic acid |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-2)-oxo-n-hydroxy carboxylic acids, (n-2),n-dihydroxy carboxylic acids, (E)-n-hydroxy-(n-2)-carboxylic acids, n-hydroxy carboxylic acids (even chain lengths, C4-C16) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| Malonyl-CoA | JC01 ΔfadB ΔfadJ ΔpaaH [THIL+ ACR+ ADH+] | 5-hydroxy-3-oxo-pentanoic acid |
| | JC01 ΔfadE ΔydiO [THIL + fadB+ ACR+ ADH+] | 3,5-dihydroxy-pentanoic acid |
| | JC01 ΔfadE ΔydiO [THIL+ fadB+ ACR+ ADH+] | (E)-5-hydroxypent-3-enoic acid |
| | JC01 [THIL+ fadB+ ydiO+ ydiQRST+ ydbK+ ACR+ ADH+] | 5-hydroxypentanoic acid |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-2)-oxo-n-hydroxy carboxylic acids, (n-2),n-dihydroxy carboxylic acids, (E)-n-hydroxy-(n-2)-carboxylic acids, n-hydroxy carboxylic acids (even chain lengths, C5-C17) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| Succinyl-CoA | JC01 ΔfadB ΔfadJ ΔpaaH [THIL+ ACR+ ADH+] | 6-hydroxy-4-oxo-hexanoic acid |
| | JC01 ΔfadE ΔydiO [THIL + fadB+ ACR+ ADH+] | 4,6.-dihydroxy-hexanoic acid |
| | JC01 ΔfadE ΔydiO [THIL+ fadB+ ACR+ ADH+] | (E)-6-hydroxy-hex-4-enoic acid |
| | JC01 [THIL+ fadB+ ydiO+ ydiQRST+ ydbK+ ACR+ ADH+] | 6-hydroxy-hexanoic acid |

TABLE 3B-continued

Synthesis of functionalized alcohols (hydroxy acids, triols, diols, aminated alcohols, branched chain alcohols) and their β-substituted derivatives via engineered reversal of the b-oxidation cycle by using functionalized primers and aldehyde-forming acyl-CoA reductases and alcohol dehydrogenases as termination pathways.

| Primer | Genotype (mutations) | Product(s) |
|---|---|---|
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-2)-oxo-n-hydroxy carboxylic acids, (n-2),n-dihydroxy carboxylic acids, (E)-n-hydroxy-(n-2)-carboxylic acids, n-hydroxy carboxylic acids (even chain lengths, C6-C18) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| | ω-aminated primers | |
| 2-aminoacetyl-CoA | JC01 ΔfadB ΔfadJ ΔpaaH [THIL+ ACR+ ADH+] | 4-amino-1-hydroxy-butan-3-one |
| | JC01 ΔfadE ΔydiO [THIL + fadB+ ACR+ ADH+] | 4-amino-butane-1,3-diol |
| | JC01 ΔfadE ΔydiO [THIL+ fadB+ ACR+ ADH+] | (E)-4-amino-but-2-en-1-ol |
| | JC01 [THIL+ fadB+ ydiO+ ydiQRST+ ydbK+ ACR+ ADH+] | 4-amino-butan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | n-amino-3-oxo-1-alcohols, n-amino-1,3-diols, (E)-n-amino-2-1-alcohols, n-amino-1-alcohols (even chain lengths, C4-C16) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| 3-aminopropionyl-CoA | JC01 ΔfadB ΔfadJ ΔpaaH [THIL+ ACR+ ADH+] | 5-amino-1-hydroxy-pentan-3-one |
| | JC01 ΔfadE ΔydiO [THIL + fadB+ ACR+ ADH+] | 5-amino-pentane-1,3-diol |
| | JC01 ΔfadE ΔydiO [THIL+ fadB+ ACR+ ADH+] | (E)-5-amino-pent-2-en-1-ol |
| | JC01 [THIL+ fadB+ ydiO+ ydiQRST+ ydbK+ ACR+ ADH+] | 5-amino-pentan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | n-amino-3-oxo-1-alcohols, n-amino-1,3-diols, (E)-n-amino-2-1-alcohols, n-amino-1-alcohols (odd chain lengths, C5-C17) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| 4-aminobutyryl-CoA | JC01 ΔfadB ΔfadJ ΔpaaH [THIL+ ACR+ ADH+] | 6-amino-1-hydroxy-hexan-3-one |
| | JC01 ΔfadE ΔydiO [THIL + fadB+ ACR+ ADH+] | 6-amino-hexane-1,3-diol |
| | JC01 ΔfadE ΔydiO [THIL+ fadB+ ACR+ ADH+] | (E)-6-amino-hex-2-en-1-ol |
| | JC01 [THIL+ fadB+ ydiO+ ydiQRST+ ydbK+ ACR+ ADH+] | 6-amino-hexan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | n-amino-3-oxo-1-alcohols, n-amino-1,3-diols, (E)-n-amino-2-1-alcohols, n-amino-1-alcohols (even chain lengths, C6-C18) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| | non-terminal/secondary carbon functionalized primers | |
| Isobutyryl-CoA | JC01 ΔfadB ΔfadJ ΔpaaH [THIL+ ACR+ ADH+] | 1-hydroxy-4-methyl-pentan-3-one |
| | JC01 ΔfadE ΔydiO [THIL + fadB+ ACR+ ADH+] | 4-methyl-pentane-1,3-diol |
| | JC01 ΔfadE ΔydiO [THIL+ fadB+ ACR+ ADH+] | (E)-4-methyl-pent-2-en-1-ol |
| | JC01 [THIL+ fadB+ ydiO+ ydiQRST+ ydbK+ ACR+ ADH+] | 4-methylpentan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-1)-methyl-3-oxo-alcohols, (n-1)-methyl-1,3,-diols, (E)-(n-1)-methyl-2-1-alcohols, (n-1)-methyl-1-alcohols (odd chain lengths, C5-C17) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| 3-methyl-butyryl-CoA | JC01 ΔfadB ΔfadJ ΔpaaH [THIL+ ACR+ ADH+] | 1-hydroxy-5-methyl-hexan-3-one |
| | JC01 ΔfadE ΔydiO [THIL + fadB+ ACR+ ADH+] | 5-methyl-hexane-1,3-diol |
| | JC01 ΔfadE ΔydiO [THIL+ fadB+ ACR+ ADH+] | (E)-5-methyl-hex-2-en-1-ol |
| | JC01 [THIL+ fadB+ ydiO+ ydiQRST+ ydbK+ ACR+ ADH+] | 5-methylhexan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-1)-methyl-3-oxo-alcohols, (n-1)-methyl-1,3,-diols, (E)-(n-1)-methyl-2-1-alcohols, (n-1)-methyl- |

TABLE 3B-continued

Synthesis of functionalized alcohols (hydroxy acids, triols, diols, aminated alcohols, branched chain alcohols) and their β-substituted derivatives via engineered reversal of the b-oxidation cycle by using functionalized primers and aldehyde-forming acyl-CoA reductases and alcohol dehydrogenases as termination pathways.

| Primer | Genotype (mutations) | Product(s) |
|---|---|---|
| | JC01 [THIL+ fadBA+ fadE+ ydiQRST+ ydbK+ ACR+ ADH+] | 1-alcohols (even chain lengths, C6-C18) |
| | JC01 [THIL+ fadBA+ Ter+ ACR+ ADH+] | |
| 2-hydroxypropionoyl-CoA | JC01 ΔfadB ΔfadJ ΔpaaH [THIL+ ACR+ ADH+] | 1,4-dihydroxy-pentan-3-one |
| | JC01 ΔfadE ΔydiO [THIL + fadB+ ACR+ ADH+] | petane-1,3,4-triol |
| | JC01 ΔfadE ΔydiO [THIL+ fadB+ ACR+ ADH+] | (E)-pent-2-ene-1,4-diol |
| | JC01 [THIL+ fadB+ ydiO+ ydiQRST+ ydbK+ ACR+ ADH+] | pentane-1,4-diol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | 3-oxo-1,(n-1)-diols, 1,3,(n-1)-triols, (E)-2-1,(n-1)-diols, 1,(n-1)-diols (odd chain lengths, C5-C17) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| 3-hydroxybutyryl-CoA | JC01 ΔfadB ΔfadJ ΔpaaH [THIL+ ACR+ ADH+] | 1,5-dihydroxy-hexan-3-one |
| | JC01 ΔfadE ΔydiO [THIL + fadB+ ACR+ ADH+] | hexane-1,3,5-triol |
| | JC01 ΔfadE ΔydiO [THIL+ fadB+ ACR+ ADH+] | (E)-hex-2-ene-1,5-diol |
| | JC01 [THIL+ fadB+ ydiO+ ydiQRST+ ydbK+ ACR+ ADH+] | Hexane-1,5-diol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | 3-oxo-1,(n-1)-diols, 1,3,(n-1)-triols, (E)-2-1,(n-1)-diols, 1,(n-1)-diols (even chain lengths, C6-C18) |
| | JC01 [THIL+ fadBA+ fadE+ ydiQRST+ ydbK+ ACR+ ADH+] | |
| | JC01 [THIL+ fadBA+ Ter+ ACR+ ADH+] | |
| 2-aminopropionoyl-CoA | JC01 ΔfadB ΔfadJ ΔpaaH [THIL+ ACR+ ADH+] | 4-amino-1-hydroxypentan-3-one |
| | JC01 ΔfadE ΔydiO [THIL + fadB+ ACR+ ADH+] | 4-amino-pentane-1,3-diol |
| | JC01 ΔfadE ΔydiO [THIL+ fadB+ ACR+ ADH+] | (E)-4-amino-pent-2-en-1-ol |
| | JC01 [THIL+ fadB+ ydiO+ ydiQRST+ ydbK+ ACR+ ADH+] | 4-amino-pentan-1-ol |
| | JC01 [THIL+ fadB+ fadE+ ydiQRST+ ydbK+ ACR+ ADH+] | |
| | JC01 [THIL+ fadB+ Ter+ ACR+ ADH+] | |
| | JC01 [THIL+ fadBA+ ydiO+ ydiQRST+ ydbK+ ACR+ ADH+] | (n-1)-amino-3-oxo-1-alcohols, (n-1)-amino-1,3-diols, (E)-(n-1)-amino-2-1-alcohols, (n-1)-amino-1-alcohols |
| | JC01 [THIL+ fadBA+ fadE+ ydiQRST+ ydbK+ ACR+ ADH+] | |
| | JC01 [THIL+ fadBA+ Ter+ ACR+ ADH+] | |

Abbreviations:
JC01, MG1655 ΔldhA ΔpoxB Δpta ΔadhE ΔfrdA::FRT-Kan-FRT sequential deletion of ldhA, poxB, pta, adhE, frdA in *E. coli* MG1655; but any *Escherichia* with ΔldhA ΔpoxB (Δpta or ΔackA or both) ΔadhE ΔfrdA will substitute.
THIL, short-chain thiolase (*E. coli* paaJ, atoB, yqeF; *Pseudomonas* sp. Strain B13 catF; *Rhodococcus opacus* pcaF and catF; *Streptomyces* sp. pcaF; *Ralstonia eutropha* phaA
THIL, short-chain thiolase (*E. coli* paaJ, atoB, yqeF; *Pseudomonas* sp. Strain B13 catF; *Rhodococcus opacus* pcaF and catF; *Streptomyces* sp. pcaF; *Ralstonia eutropha* phaA and bktB; *Clostridium acetobutylicum* thlA and thlB);
ACR, aldehyde forming acyl-CoA reductase (*Acinetobacter calcoaceticus* acr1, *Acinetobacter* sp. Strain M-13 acr1, *Clostridium kluyveri* sucD, *E. coli* mhpF and eutE, *Clostridium beijerinckii* ald, *Salmonella typhimurium* eutE);
ADH, alcohol dehydrogenase (*E. coli* fucO, betA, eutG, yiaY, *Clostrium acetobutylicum* adhE2 NOTE this enzyme catalyzes both steps);
Ter, trans-enoyl-CoA reductase from *E. gracilis*, and other sources such as Mammaliam (Human, Rat, Chinese hamster ovary cells), bacterial (*Treponema denticola*, *Flavobacterium johnsoniae*, *Polaribacter irgensii*), Apicomplexas (*Toxoplasma gondii*, *Plasmodium falciparum*, *Theileria parva*, *Babesia bovis*, *Cryptosporidium parvum*), Plant (*A. thaliana*, *Gossypium hirsutum* L. cv. Xuzhou 142), and Yeast (*S. cerevisiae*).

TABLE 4A

SYNTHESIS OF b-SUBSTITUTED (b-KETO-, b-HYDROXY- AND TRANS-Δ$^2$-) AND UNSUBSTITUTED CARBOXYLIC ACIDS, HYDROXY ACIDS, CARBOXYLATED ALCOHOLS, DIACIDS. Product families generated using CoA thioester hydrolases/thioesterases, acyltransferase, or acyl-CoA kinase as termination enzymes and different primer or starter molecules.

| Primer or starter | Product Family (includes both odd- and even-chain products of chain-length ≥4) | | | | |
|---|---|---|---|---|---|
| Acetyl-CoA and propionyl-CoA | b-keto monocarboxylic acids | b-hydroxy monocarboxylic acids | trans-D$^2$ monocarboxylic acids | unsubstituted monocarboxylic acids | |
| Hydroacetyl-CoA, hydroxypropionyl-CoA, and hydroxysuccinyl-CoA | b-keto w-hydroxy monocarboxylic acids | b-hydroxy w-hydroxy monocarboxylic acids | trans-D$^2$ w-hydroxy monocarboxylic acids | w-hydroxy monocarboxylic acids | |
| Oxalyl-CoA, malonyl-CoA and Succinyl-CoA | b-keto dicarboxylic acids | b-hydroxy dicarboxylic acids | trans-D$^2$ dicarboxylic acids | unsubstituted dicarboxylic acids | |

TABLE 4B

SYNTHESIS OF b-SUBSTITUTED (b-KETO-, b-HYDROXY- AND TRANS-$\Delta^2$-) AND UNSUBSTITUTED ALCOHOLS, HYDROXY ACIDS, CARBOXYLATED ALCOHOLS, AND DIOLS. Product families generated using alcohol-forming CoA thioester reductases or aldehyde-forming CoA thioester reductases & alcohol dehydrogenases as termination enzymes and different primer or starter molecules.

| Primer or starter | Product Family (includes both odd- and even-chain products of chain-length ≥4) | | | |
|---|---|---|---|---|
| Acetyl-CoA and propionyl-CoA | b-keto n-alcohols | 1,3-Diols | trans-$D^2$ n-alcohols | unsubstituted n-alcohols |
| Hydroacetyl-CoA, hydroxypropionyl-CoA, and hydroxysuccinyl-CoA | b-keto 1,n-diols | 1,3,n-triols | trans-$D^2$ 1,n-diols | 1,n-diols |
| Oxalyl-CoA, malonyl-CoA and Succinyl-CoA | b-keto w-hydroxy monocarboxylic acids | b-hydroxy w-hydroxy monocarboxylic acids | trans-$D^2$ w-hydroxy monocarboxylic acids | w-hydroxy monocarboxylic acids |

TABLE 4C

SYNTHESIS OF b-SUBSTITUTED (b-KETO-, b-HYDROXY- AND TRANS-$\Delta^2$-) AND UNSUBSTITUTED w-HYDROXY ACIDS, w-KETO ACIDS, CARBOXYLATED ALCOHOLS, AND DIACIDS. Product families generated by the action of omega-oxidation enzymes acting on carboxylic acids derived from the b-oxidation reversal.

| w-oxidation enzyme | Product Family (includes both odd- and even-chain products of chain-length ≥4) | | | |
|---|---|---|---|---|
| Enzyme (1) FIG. 5 | b-keto w-hydroxy monocarboxylic acids | b-hydroxy w-hydroxy monocarboxylic acids | trans-$D^2$ w-hydroxy monocarboxylic acids | w-hydroxy monocarboxylic acids |
| Enzyme (2) FIG. 5 | b-keto w-keto monocarboxylic acids | b-hydroxy w-keto monocarboxylic acids | trans-$D^2$ w-keto monocarboxylic acids | w-keto monocarboxylic acids |
| Enzyme (3) FIG. 5 | b-keto dicarboxylic acids | b-hydroxy dicarboxylic acids | trans-$D^2$ dicarboxylic acids | unsubstituted dicarboxylic acids |

TABLE 4D

SYNTHESIS OF b-SUBSTITUTED (b-KETO-, b-HYDROXY- AND TRANS-$\Delta^2$-) AND UNSUBSTITUTED w-HYDROXY ACIDS, w-ALDO ACIDS, CARBOXYLATED ALCOHOLS, AND DIOLS. Product families generated by the action of omega-oxidation enzymes acting on n-alcohols derived from the b-oxidation reversal.

| w-oxidation enzyme | Product Family (includes both odd- and even-chain products of chain-length ≥4) | | | |
|---|---|---|---|---|
| Enzyme (1) FIG. 5 | b-keto 1,n-diols | 1,3,n-triols | trans-$D^2$ 1,n-diols | 1,n-diols |
| Enzyme (2) FIG. 5 | b-keto w-aldo n-alcohols | w-aldo 1,3-diols | trans-$D^2$ w-aldo n-alcohols | w-aldo n-alcohols |
| Enzyme (3) FIG. 5 | b-keto w-carboxylated n-alcohol | b-hydroxy w-carboxylated n-alcohol | trans-$D^2$ w-carboxylated n-alcohol | w-hydroxy monocarboxylic acids |

TABLE 4E

SYNTHESIS OF b-SUBSTITUTED (b-KETO-, b-HYDROXY- AND TRANS-$\Delta^2$-) AND UNSUBSTITUTED w-HYDROXY ACIDS, w-ALDO ACIDS, CARBOXYLATED ALCOHOLS, AND DIOLS. Product families generated by the action of alpha oxidation enzymes acting on unsubstituted n-alcohols and carboxylic acids derived from the b-oxidation reversal.

| a-oxidation enzyme/acting on acid or alcohol | Product Family (includes both odd- and even-chain products of chain-length ≥4) | | | |
|---|---|---|---|---|
| Enzyme (4) FIG. 5/n-alcohols | b-keto 1,2-diols | 1,2,3-triols | trans-$D^2$ 1,2-diols | 1,2-diols |
| Enzyme (4) FIG. 5/carboxylic acids | a-hydroxy b-keto monocarboxylic acids | a,b-dihydroxy monocarboxylic acids | a-hydroxy trans-$D^2$ monocarboxylic acids | a-hydroxy monocarboxylic acids |

TABLE 5

Genes and Proteins

| Gene | EC NO. | Prot. Acc. No (species) | Details |
|---|---|---|---|
| ACH2 | 3.1.2.— | AAR21571.1 (*Arabidopsis*) | Gene encoding acyl-CoA thioesterase from *Arabidopsis thaliana* |
| acot8 | 3.1.2.— | AAH05792.1 (*Mus musculus*) | Gene encoding acyl-CoA thioesterase 8 from *Mus musculus* |
| ackA | 2.7.2.1 | NP_416799.1 (*E. coli*) | Gene encoding acetate kinase, required for synthesis of acetate from acetyl-CoA. |

TABLE 5-continued

Genes and Proteins

| Gene | EC NO. | Prot. Acc. No (species) | Details |
|---|---|---|---|
| act | 2.8.3.— | CAG29276.1 (*Clostridium*) | Gene encoding beta-alanine CoA transferase from *Clostridium propionicum* |
| adhE | 1.2.1.10 1.1.1.1 | NP_415757.1 (*E. coli*) | Gene encoding aldehyde/alcohol dehydrogenase, required for synthesis of ethanol from acetyl-CoA |
| adhE2 | 1.2.1.10 1.1.1.1 | AAK09379.1 (*Clostridium*) | Gene encoding aldehyde/alcohol dehydrogenase from *Clostridium acetobutylicum* |
| ald | 1.2.1.10 | AAT48939.1 (*Clostridium*) | Gene encoing acyl-CoA reductase from *Clostridium beijerinckii* |
| aldA | 1.2.1.21 1.2.1.22 | NP_415933.1 (*E. coli*) | Gene encoding NAD linked aldehyde dehydrogenase A (aka glycolaldehyde:NAD+ oxidoreductase) |
| arcA | NA | NP_418818.1 (*E. coli*) | Encodes the cytosolic transcription factor of *E. coli*'s ArcAB two-component system, a global regulator of gene expression under microaerobic and anaerobic conditions. ArcAB regulates the expression of a large number of operons involved in respiratory and fermentative metabolism (including repression of fad regulon). |
| arcB | NA | YP_026207.1 (*E. coli*) | Encodes the membrane associated sensor kinase and phosphatase of *E. coli*'s ArcAB two-component system, a global regulator of gene expression under microaerobic and anaerobic conditions. ArcAB regulates the expression of a large number of operons involved in respiratory and fermentative metabolism (including repression of fad regulon). |
| AtFAO3 | 1.1.3.20 | AEE76762.1 (*Arabidopsis*) | Gene encoding long chain alcohol oxidase from *Arabidopsis* (AtFAO3) |
| atoC | NA | NP_416724.1 (*E. coli*) | Encodes the cytosolic transcription factor of *E. coli*'s AtoSC two-component system, which induces the ato operon (atoDAEB) for metabolism of short chain fatty acids in response to the presence of acetoacetatE. |
| atoC(c) | NA | JF793626.1 | Encodes an AtoC mutant that induces constitutive expression of the ato operon (atoDAEB) in the absence of acetoacetate. |
| atoS | NA | NP_416723.1 (*E. coli*) | Encodes the membrane associated sensor kinase of *E. coli*'s AtoSC two-component system, which induces the ato operon (atoDAEB) for metabolism of short chain fatty acids in response to the presence of acetoacetate. |
| betA | 1.1.99.1 | NP_414845.1 (*E. coli*) | Gene encoding choline dehydrogenase (BetA) aka betaine aldehyde dehydrogenase; used as a surrogate of alcohol dehydrogenase in the synthesis of n-alcohols |
| crp | NA | NP_417816.1 (*E. coli*) | Encodes transcriptional dual regulator CRP, which upon binding to its allosteric effector cyclic AMP (cAMP) regulate the expression of about 200 genes (most of them involved in the catabolism of carbon sources, including the fad regulon). |
| crp* | NA | JF781281.1 (*E. coli*) | A CRP mutant encoding a cAMP-independent CRP (i.E. CRP*, which does not require cAMP to regulate gene expression and hence prevents catabolite repression of fad regulon in the presence of glucose) |
| cysJ | 1.8.1.2 1.6.8.1 | NP_417244.1 (*E. coli*) | Gene encoding the flavoprotein subunit (CysJ) complex of sulfite reductase. Along with YdbK, CysJ could form a pyruvate: NADP oxidoreductase: we propose that ydbK and cysJ would encode the N-terminal pyruvate: ferredoxin oxidoreductase domain and the C-terminal NADPH-cytochrome P450 reductase domain, respectively. |
| egTER | 1.3.1.44 | AAW66853.1 (*Euglena*) | Gene encoding an NAD(P)H-dependent transenoyl-CoA reductase from *Euglena gracilis* |
| eutE | 1.2.1.— | NP_416950.1 (*E. coli*) AAA80209.1 (*Salmonella*) | Gene encoding predicted aldehyde dehydrogenase (EutE) with high sequence similarity to adhE |
| eutG | 1.1.— | NP_416948.4 (*E. coli*) | Gene encoding predicted alcohol dehydrogenase (EutG) |
| fadA | 2.3.1.16 | YP_026272.1 (*E. coli*) | Gene encoding 3-ketoacyl-CoA thiolase (thiolase I) (FadA), a component of fatty acid oxidation complex FadAB |
| fadB | 5.3.3.8 4.2.1.17 5.1.2.3 1.1.1.35 | NP_418288.1 (*E. coli*) | Gene encoding hydroxyacyl-CoA dehydrogenase, aka fused 3-hydroxybutyryl-CoA epimerase and delta(3)-cis-delta(2)-trans-enoyl-CoA isomerase and enoyl-CoA hydratase, part of fatty acid oxidation complex |
| fadBA | / | / | Both fadA and fadB, |
| fadD | 6.2.1.3 | NP_416319.1 (*E. coli*) | Gene encoding acyl-CoA synthetase (long-chain-fatty-acid--CoA ligase) (FadD), part of fatty acyl-CoA synthetase complex |
| fadE | 1.3.99.3 | NP_414756.2 (*E. coli*) | Gene encoding acyl-CoA dehydrogenase (FadE), a medium-long-chain fatty acyl-CoA dehydrogenase |
| fadI | 2.3.1.16 | NP_416844.1 (*E. coli*) | Gene encoding 3-ketoacyl-CoA thiolase, aka yfcY (YfcY), part of fatty acid oxidation complex |
| fadJ | 4.2.1.17 5.3.3.8 5.1.2.3 1.1.1.35 | NP_416843.1 (*E. coli*) | Gene encoding hydroxyacyl-CoA dehydrogenase aka yfcX (YfcX), aka fused enoyl-CoA hydratase, 3-hydroxybutyryl-CoA epimerase, dodecenoyl-CoA D-isomerase, and 3-hydroxyacyl-CoA dehydrogenase, subunit of anaerobic fatty acid oxidation complex |
| fadJI | / | / | Both fadJ and fadI |
| fadK (ydiD) | 6.2.1.— | NP_416216.4 (*E. coli*) | Gene encoding short chain acyl-CoA synthetase (FadK) aka YdiD |
| fadL | | NP_416846.2 (*E. coli*) | Gene encoding long-chain fatty acid outer membrane transporter (FadL) |
| fadM | 3.1.2.— | NP_414977.1 (*E. coli*) | Gene encoding long-chain acyl-CoA thioesterase |
| fadR | NA | NP_415705.1 (*E. coli*) | Gene encoding a dual regulator of fatty acid metabolism, which exerts negative control over the fad regulon and positive control over expression of unsaturated fatty acid biosynthesis genes |
| fadR | NA | JF793627.1 | fadR mutant that allows expression of the fad regulon in the absence of fatty acids |
| fao1 | 1.1.3.20 | XP_712386.1 (*Candida*) | Gene encoding long-chain fatty alcohol oxidase (Fao1) in yeast, *Candida cloacae*. |

TABLE 5-continued

Genes and Proteins

| Gene | EC NO. | Prot. Acc. No (species) | Details |
|---|---|---|---|
| fao2 | 1.1.3.20 | CAB75352.1 (*Candida*) | Gene encoding the long-chain fatty alcohol oxidase (Fao2) in yeast, *Candida cloacae*, aka ω-hydroxy fatty acid oxidase |
| fnr | NA | NP_415850.1 (*E. coli*) | Gene encoding transcriptional dual regulator (Fnr), regulates genes involved in the transition from aerobic to anaerobic growth |
| frdA | 1.3.99.1 | NP_418578.1 (*E. coli*) | Gene encoding one of the catalytic subunits of fumarate reductase (FrdABCD), required for synthesis of succinate from fumarate |
| ldhA | 1.1.1.28 | NP_415898.1 (*E. coli*) | Gene encoding lactate dehydrogenase (LdhA) |
| mgsA | 4.2.3.3 | NP_415483.2 (*E. coli*) | Gene encoding methylglyoxal synthase (MgsA); key enzyme in the synthesis of lactate through the methylglyoxal bypass |
| mhpF | 1.2.1.10 | NP_414885.1 (*E. coli*) | Gene encoding an acetaldehyde dehydrogenase (MhpF) |
| oleA | | | Gene encoding the enzyme that catalyzes non-decarboxylative Claisen condensation of CoA-thioesters in *Xanthomonas campestris* |
| oleB | | | Gene encoding a member of the α/β-hydrolase superfamily in *Xanthomonas campestris* |
| oleC | | | Gene encoding a member of the AMPdependent ligase/synthase superfamily or acetyl-CoA synthetase-like superfamily in Xanthomonas campestris |
| oleD | | | Gene encoding a member of the short-chain dehydrogenase/reductase superfamily in Xanthomonas campestris |
| paaI | 3.1.2.— | NP_415914.1 (*E. coli*) | Gene encoding hydroxyphenylacetyl-CoA thioesterase (PaaI) |
| paaJ | 2.3.1.174 | NP_415915.1 (*E. coli*) | Gene encoding β-ketoadipyl-CoA thiolase (PaaJ) catalyzing two beta-oxidation steps in phenylacetate catabolism |
| PCC7942_orf1593 | 4.1.99.5 | YP_400610.1 (*Synechococcus*) | Gene encoding an aldehyde decarbonylase from *Synechococcus elongatus* PCC7942 |
| pct | 2.8.3.— | YP_004765791.1 (*Megasphaera*) | Gene encoding the CoA transferase with wide substrate range (C2-C4) from *Megasphaera elsdenii* |
| PMT9312_0532 | 4.1.99.5 | ABB49593.1 (*Prochlorococcus*) | Gene encoding an aldehyde decarbonylase from *Prochlorococcus marinus* MIT9313 |
| poxB | 1.2.2.2 | NP_415392.1 (*E. coli*) | Gene encoding pyruvate oxidase (PoxB), which catalyzes the oxidative decarboxylation of pyruvate to form acetate, reduced ubiquinone (ubiquinol), and $CO_2$ |
| pta | 2.3.1.8 | NP_416800.1 (*E. coli*) | Gene encoding phosphotransacetylase, required for synthesis of acetate from acetyl-CoA |
| tdTER | 1.3.1.44 | NP_971211.1 (*Treponema*) | Gene encoding an NAD(P)H-dependent transenoyl-CoA reductase from *Treponema denticola* |
| tesA | 3.1.2.— 3.1.1.5 | NP_415027.1 (*E. coli*) | Gene encoding multifunctional acyl-CoA thioesterase I and protease I and lysophospholipase L1 (TesA) |
| tesB | 3.1.2.— | NP_414986.1 (*E. coli*) CAL16477.1 (*Alcanivorax*) | Gene encoding thioesterase II (TesB) |
| ucpA | 1.—.—.— | NP_416921.4 (*E. coli*) | predicted oxidoreductase, sulfate metabolism protein (used as surrogate of aldehyde-forming acyl Coenzyme A Reductase) (UcpA) |
| ybbO | 1.—.—.— | NP_415026.1 (*E. coli*) | predicted oxidoreductase with NAD(P)-binding Rossmann-fold domain (used as surrogate of aldehyde-forming acyl Coenzyme A Reductase) (YbbO) |
| ybdB | 3.1.2.— | NP_415129.1 (*E. coli*) | Gene encoding proofreading thioesterase EntH (YbdB) |
| ybdH | 1.1.—.— | NP_415132.1 (*E. coli*) | Gene encoding predicted oxidoreductase (YbdH) |
| ybgC | 3.1.2.— | NP_415264.1 (*E. coli*) | Gene encoding an Acyl-CoA thioesterase (YbgC) |
| yciA | 3.1.2.— | NP_415769.1 (*E. coli*) | Gene encoding acyl-CoA thioesterase (YciA) |
| ydbK | 1.2.7.— | NP_415896.1 (*E. coli*) | Gene encoding fused predicted pyruvate-flavodoxin oxidoreductase (YdbK) |
| ydiI | 3.1.2.— | NP_416201.1 (*E. coli*) | Gene encoding an Acyl-CoA thioesterase (YdiI) |
| ydiL | | NP_416204.2 (*E. coli*) | Gene encoding fused predicted acetyl-CoA:acetoacetyl-CoA transferase: α subunit/β subunit (YdiL) |
| ydiO | 1.3.—.— | NP_416210.4 (*E. coli*) | Genes encoding predicted acyl-CoA dehydrogenase (YdiO) |
| ydiQ | | NP_416212.1 (*E. coli*) | Gene encoding putative subunit (YdiQ) of YdiQ-YdiR flavoprotein |
| ydiR | ??? | NP_416213.1 (*E. coli*) | Gene encoding putative subunit (YdiR) of YdiQ-YdiR flavoprotein |
| ydiS | ??? | NP_416214.1 (*E. coli*) | Gene encoding putative flavoprotein (YdiS) |
| ydiT | ??? | NP_416215.1 (*E. coli*) | Gene encoding putative ferredoxin (YdiT) |
| yiaY | 1.1.1.— | YP_026233.1 (*E. coli*) | Gene encoding predicted Fe-containing alcohol dehydrogenase (YiaY) |
| yqhD | 1.1.1.— | NP_417484.1 (*E. coli*) | Gene encoding NADP-dependent aldehyde/alcohol dehydrogenase aka oxidoreductase |

Exemplary gene/protein/species provided in this table. However, gene, protein and enzyme nomenclature varies widely, thus any protein that catalyzes the same reaction can be substituted herein.
Exemplary protein sequence accession numbers provided herein, but each is linked to the corresponding DNA (or amino acid) sequence, and to related sequences.
*E. coli* gene and protein names can be ascertained through ecoliwiki.net/ and enzymes can be searched through brenda-enzymes.info/. Many similar databases are available including PROSITE; EC2PDB; ExplorEnz; PRIAM; KEGG Ligand; IUBMB Enzyme Nomenclature; IntEnz; MEDLINE; and MetaCyc, to name a few.
By convention, genes are written in italic, and corresponding proteins in regular font. E.g., ackA is the gene encoding AckA aka acetate kinase

SUPPLEMENTARY TABLE S1

Strains and Plasmids used in this study.

| Strain/Plasmid | Description/Genotype | Source |
|---|---|---|
| MG1655 | F-λ-ilvG-rfb-50 rph-1 | Kang et al. (2004) |
| MG1655 ΔldhAΔpoxBΔptaΔadhE | MG1655, ΔldhA::FRT ΔpoxB::FRT Δpta::FRT ΔadhE::FRT sequential deletion of ldhA, poxB, pta, and adhE in MG1655 | Blankschien et al. (2010) |

SUPPLEMENTARY TABLE S1-continued

Strains and Plasmids used in this study.

| Strain/Plasmid | Description/Genotype | Source |
|---|---|---|
| MG1655 ΔldhAΔpoxBΔptaΔadhEΔfrdA (JC01) | MG1655, ΔldhA::FRT ΔpoxB::FRT Δpta::FRT ΔadhE::FRT ΔfrdA::FRT-Kan-FRT sequential deletion of ldhA, poxB, pta, adhE, and frdA in MG1655 | This Study |
| JC01 ΔtesA | MG1655, ΔldhA::FRT ΔpoxB::FRT Δpta::FRT ΔadhE::FRT ΔfrdA::FRT-ΔtesA::FRT-Kan-FRT sequential deletion of ldhA, poxB, pta, adhE, frdA, and tesA in MG1655 | This Study |
| JC01 ΔtesB | MG1655, ΔldhA::FRT ΔpoxB::FRT Δpta::FRT ΔadhE::FRT ΔfrdA::FRT-ΔtesB::FRT-Kan-FRT sequential deletion of ldhA, poxB, pta, adhE, frdA, and tesB in MG1655 | This Study |
| JC01 ΔyciA | MG1655, ΔldhA::FRT ΔpoxB::FRT Δpta::FRT ΔadhE::FRT ΔfrdA::FRT-ΔyciA::FRT-Kan-FRT sequential deletion of ldhA, poxB, pta, adhE, frdA, and yciA in MG1655 | This Study |
| JC01 ΔfadM | MG1655, ΔldhA::FRT ΔpoxB::FRT Δpta::FRT ΔadhE::FRT ΔfrdA::FRT-ΔfadM::FRT-Kan-FRT sequential deletion of ldhA, poxB, pta, adhE, frdA, and fadM in MG1655 | This Study |
| JC01 ΔydiI | MG1655, ΔldhA::FRT ΔpoxB::FRT Δpta::FRT ΔadhE::FRT ΔfrdA::FRT-ΔydiI::FRT-Kan-FRT sequential deletion of ldhA, poxB, pta, adhE, frdA, and ydiI in MG1655 | This Study |
| JC01 ΔybgC | MG1655, ΔldhA::FRT ΔpoxB::FRT Δpta::FRT ΔadhE::FRT ΔfrdA::FRT-ΔybgC::FRT-Kan-FRT sequential deletion of ldhA, poxB, pta, adhE, frdA, and ybgC in MG1655 | This Study |
| JC01 ΔfadB | MG1655, ΔldhA::FRT ΔpoxB::FRT Δpta::FRT ΔadhE::FRT ΔfrdA::FRT-ΔfadB::FRT-Kan-FRT sequential deletion of ldhA, poxB, pta, adhE, frdA, and fadB in MG1655 | This Study |
| JC01 ΔfadE | MG1655, ΔldhA::FRT ΔpoxB::FRT Δpta::FRT ΔadhE::FRT ΔfrdA::FRT-ΔfadE::FRT-Kan-FRT sequential deletion of ldhA, poxB, pta, adhE, frdA, and fadE in MG1655 | This Study |
| JC01 ΔydiO | MG1655, ΔldhA::FRT ΔpoxB::FRT Δpta::FRT ΔadhE::FRT ΔfrdA::FRT-ΔydiO::FRT-Kan-FRT sequential deletion of ldhA, poxB, pta, adhE, frdA, and ydiO in MG1655 | This Study |
| pTrcHis2A (pTH$_4$) | pTrcHis2A (pBR322-derived), oriR pMB1, lacI$^q$, bla | Invitrogen (Carlsbad, CA) |
| pTH$_4$-atoB | E. coli atoB gene under trc promoter and lacI$^q$ control | This Study |
| pTH$_4$-atoB-fadB | E. coli atoB and fadB genes under trc promoter and lacI$^q$ control | This Study |
| pTH$_4$-atoB-fadB-ydiO | E. coli atoB, fadB, and ydiO genes under trc promoter and lacI$^q$ control | This Study |
| pTH$_4$-atoB-fadB-egTER | E. coli atoB and, fadB, and E. gracilis TER genes under trc promoter and lacI$^q$ control | This Study |
| pTH$_4$-atoB-fadB-fadE | E. coli atoB, fadB, and fadE genes under trc promoter and lacI$^q$ control | This Study |
| pZS-Blank | oriR pSC101*, tetR, cat, contains P$_{LtetO-1}$ | Yazdani and Gonzalez (2008) |
| pZS-fadM | E. coli fadM gene under control of P$_{LtetO-1}$(tetR, oriR SC101*, cat) | Dellomonaco et al. (2011) |
| pZS-tesA | E. coli tesA gene under control of P$_{LtetO-1}$(tetR, oriR SC101*, cat) | Dellomonaco et al. (2011) |
| pZS-tesB | E. coli tesB gene under control of P$_{LtetO-1}$(tetR, oriR SC101*, cat) | Dellomonaco et al. (2011) |
| pZS-ybgC | E. coli ybgC gene under control of P$_{LtetO-1}$(tetR, oriR SC101*, cat) | This Study |
| pZS-yciA | E. coli yciA gene under control of P$_{LtetO-1}$(tetR, oriR SC101*, cat) | Dellomonaco et al. (2011) |
| pZS-ydbK | E. coli ydbK gene under control of P$_{LtetO-1}$(tetR, oriR SC101*, cat) | This Study |
| pZS-ydiI | E. coli ydiI gene under control of P$_{LtetO-1}$(tetR, oriR SC101*, cat) | This Study |
| pZS-fadB-egTER | E. coli fadB and E. gracilis TER genes under control of P$_{LtetO-1}$(tetR, oriR SC101*, cat) | This Study |
| pZS-fadBA-egTER | E. coli fadBA and E. gracilis TER genes under control of P$_{LtetO-1}$(tetR, oriR SC101*, cat) | This Study |
| pZS-ydbK-ydiQRST | E. coli ydbK and ydiQRST genes under control of P$_{LtetO-1}$(tetR, oriR SC101*, cat) | This Study |

SUPPLEMENTARY TABLE S2

Primers used in this study for plasmid construction. Primers were used to amplify the last gene listed in the plasmid to clone into the vector backbone listed in parenthesis previously digested with the listed restriction enzyme(s). For further details, see Methods.

| Plasmid Construction | SEQ ID NO | Primer Sequences and Restriction Enzymes Used |
|---|---|---|
| pZS-fadM | 1. | 5'-TTAAAGAGGAGAAAGGTACCATGCAAACACAAATCAAAGT-3' <br> 5'-TGCCTCTAGCACGCGTCGTTTACTTAACCATCTGCTCCA-3' (pZS, KpnI/MluI) |
| pZS-tesA | 2. | 5'-TTAAAGAGGAGAAAGGTACCATGATGAACTTCAACAATGTTTTC-3' <br> 5'-TGCCTCTAGCACGCGTTCCGTTGCTTTATGAGTCATG-3' (pZS, KpnI/MluI) |
| pZS-tesB | 3. | 5'-TTAAAGAGGAGAAAGGTACCATGAGTCAGGCGCTAAAAAA-3' <br> 5'-TGCCTCTAGCACGCGTAACAGCCGGACGGTTTTC-3' (pZS, KpnI/MluI) |
| pZS-ybgC | 4. | 5'-TTAAAGAGGAGAAAGGTACCGTGAATACAACGCTGTTTCGAT-3' <br> 5'-TGCCTCTAGCACGCGTTCACTGCTTAAACTCCGCGA-3' (pZS, KpnI/MluI) |
| pZS-yciA | 5. | 5'-TTAAAGAGGAGAAAGGTACCATGTCTACAACACATAACGTCCC-3' <br> 5'-TGCCTCTAGCACGCGTTTCAGTAAGCAGAAAGTCAAAGC-3' (pZS, KpnI/MluI) |

SUPPLEMENTARY TABLE S2-continued

Primers used in this study for plasmid construction. Primers were used to amplify the last gene listed in the plasmid to clone into the vector backbone listed in parenthesis previously digested with the listed restriction enzyme(s). For further details, see Methods.

| Plasmid Construction | SEQ ID NO | Primer Sequences and Restriction Enzymes Used |
|---|---|---|
| pZS-ydbK | 6. | 5'-TTAAAGAGGAGAAAGGTACCATGATTACTATTGACGGTAATGGC-3'<br>5'TGCCTCTAGCACGCGTGCATTTAATCGGTGTTGCTTT-3' (pZS, KpnI/MluI) |
| pZS-ydiI | 7. | 5'-TTAAAGAGGAGAAAGGTACCATGATATGGAAACGGAAAATCA-3'<br>5'-TGCCTCTAGCACGCGTGGTGACAACGTCACAAAATGG-3' (pZS, KpnI/MluI) |
| pZS-fadB-egTER | 8. | 5'-GCAGAAGATCACGCGAAATAAGGAGGAATAAACCATGGCAATGTTTACCACGAC-3'<br>5'-TGCCTCTAGCACGCGTGCGGCCGCTTATTGCTGTGCTGCGGAC-3' (pZS-fadB, MluI) |
| pZS-fadBA-egTER | 9 | 5'-TTTAACCACTACGCGAATAAGGAGGAATAAACCATGGCAATGTTTACCACGAC-3'<br>5'-TGCCTCTAGCACGCGTGCGGCCGCTTATTGCTGTGCTGCGGAC-3' (pZS-fadBA, MluI) |
| pZS-ydbK-ydiQRST | 10. | 5'-TTAAATGCTGCGGCCATCGGAGATGGTTCCGTATG-3'<br>5'-AGCACGCGTGCGGCCGCCATGATTAGCCGTAGCGAAA-3' (pZS-ydbK, NotI) |
| pTH$_4$-atoB | 11. | 5'-GAGGAATAAACCATGAAAAATTGTGTCATCGTCA-3'<br>5'-CCCAAGCTTCGAATTCTTAATTCAACCGTTCAATCAC-3' (pTH$_4$, NcoI/EcoRI) |
| pTH$_4$-atoB-fadB | 12. | 5'-TAAGAATTCGAAGCTGCGGATTCAGGAGACTGACA-3'<br>5'-GTTCGGGCCCAAGCTTTAAGCCGTTTTCAGGTCGC-3' (pTH$_4$-atoB, HindIII) |
| pTH$_4$-atoB-fadB-caiA | 13. | 5'-AAACGGCTTAAAGCTAATAAGGAGGAATAAACCATGGATTTTAATTTAAATGATGAGCAG-3'<br>5'-GTTCGGGCCCAAGCTTGCGGCCGCCGGACTTAGCGGTATTGCTT-3'<br>(pTH$_4$-atoB-fadB, HindIII) |
| pTH$_4$-atoB-fadB-ydiO | 14. | 5'-AAACGGCTTAAAGCTAATAAGGAGGAATAAACCATGGATTTTTCTTTAACTGAAGAACA-3'<br>5'-GTTCGGGCCCAAGCTTGCGGCCGCTGCAGATTATTTGTTCTGATAGTCTTT-3'<br>(pTH$_4$-atoB-fadB, HindIII) |
| pTH$_4$-atoB-fadB-egTER | 15. | 5'-AAACGGCTTAAAGCTAATAAGGAGGAATAAACCATGGCAATGTTTACCACGAC-3'<br>5'-GTTCGGGCCCAAGCTTGCGGCCGCTTATTGCTGTGCTGCGGAC-3'<br>(pTH$_4$-atoB-fadB, HindIII) |
| pTH$_4$-atoB-fadB-fadE | 16. | 5'-AAACGGCTTAAAGCTAATAAGGAGGAATAAACCATGATGATTTTGAGTATTCTCGCTAC-3'<br>5'-GTTCGGGCCCAAGCTTGCGGCCGCCATTTACGCGGCTTCAACTT-3'<br>(pTH$_4$-atoB-fadB, HindIII) |

SUPPLEMENTARY TABLE S3

Primers used in the construction of plasmids for enzymatic characterization. For further details on construction, see Methods.

| Primer | SEQ ID NO | Sequences |
|---|---|---|
| fadANdel5p | 17. | CCCTTTCATATGGAACAGGTTGTCATTGTC |
| fadAmidrev | 18. | CGGCACATGGCCCATGTGCTCCACGCCGCCAACCAG |
| fadAmidfor | 19. | CTGGTTGGCGGCGTGGAGCACATGGGCCATGTGCCG |
| fadANotI3p | 20. | GGAAAAGCGGCCGCTTAAACCCGCTCAAACACCG |
| fadBNdel5p | 21. | TTTTCCCATATGCTTTACAAAGGCGACAC |
| fadBmid1rev | 22. | CAGCAGCCCTTTTAGATCCGATTGCTGTTCCAGCAC |
| fadBmid1for | 23. | GTGCTGGAACAGCAATCGGATCTAAAAGGGCTGCTG |
| fadBmid2rev | 24. | GGTCGGCACCGGCAGGTCTTCCAGGCGATTAAACAC |
| fadBmid2for | 25. | GTGTTTAATCGCCTGGAAGACCTGCCGGTGCCGACC |

SUPPLEMENTARY TABLE S3-continued

Primers used in the construction of plasmids for enzymatic characterization. For further details on construction, see Methods.

| Primer | SEQ ID NO | Sequences |
|---|---|---|
| fadBNotI3p | 26. | CCAAAAGCGGCCGCTTAAGCCGTTTTCAGGTC |
| caHBDBglii5p | 27. | AAACCCAGATCTATGAAAAAGGTATGTGTTATAG |
| caHBDxhoI3p | 28. | TTAAAACTCGAGTTTTGAATAATCGTAGAAAC |
| F1pTH6hisEgter | 29. | GAGGAATAAACCATGCATCATCATCATCATCATGCAATGTTTACCACGACCGCGA |
| R1pTH6hisEgter | 30. | CCCAAGCTTCGAATTCTTATTGCTGTGCTGCGGACGG |

All references cited herein are incorporated by reference in their entirety herein for all purposes. Certain references are listed again below for the convenience of the reader, and additional references may be found in the legends to the FIGURES.

Dellomonaco C, et al., Engineered reversal of the β-oxidation cycle for the synthesis of fuels and chemicals. Nature. 476(7360):355-9 (2011)
Jansen and Wanders: Biochimica et Biophysica Acta 1763 (2006) 1403-1412).
Pinot F, Beisson F. (2011). Cytochrome P450 metabolizing fatty acids in plants: characterization and physiological roles. FEBS J, 278 (2), 195-205.
Mascaraque et al., 2010, PNAS 107:14390-14395
Nogales et al., 2007, Microbiology 153:357-365),
Gobel et al., 2002, J. Bac. 184: 216-223
Eulberg et al., 1998, J. Bacteriol. 180:1072-1081
Iwagami et al., 2000, Appl. Environ. Microbiol. 66:1499-1508
U.S. Ser. No. 61/440,192, filed Feb. 7, 2011
U.S. Ser. No. 61/531/911, filed Sep. 7, 2011
PCT/US12/24051, filed Feb. 7, 2012
WO2010101651
1. Rude, M. A., and Schirmer, A. (2009) New microbial fuels: a biotech perspective, Curr. Opin. Microbiol. 12, 274-281.
2. Connor, M. R., and Liao, J. C. (2009) Microbial production of advanced transportation fuels in non-natural hosts, Curr. Opin. Biotechnol. 20, 307-315.
3. Lee, J. W., Na, D., Park, J. M., Lee, J., Choi, S., and Lee, S. Y. (2012) Systems metabolic engineering of microorganisms for natural and non-natural chemicals, Nat. Chem. Biol. 8, 536-546.
4. Peralta-Yahya, P. P., Zhang, F., del Cardayre, S. B., and Keasling, J. D. (2012) Microbial engineering for the production of advanced biofuels, Nature 488, 320-328.
5. Steen, E. J., Kang, Y. S., Bokinsky, G., Hu, Z. H., Schirmer, A., McClure, A., del Cardayre, S. B., and Keasling, J. D. (2010) Microbial production of fatty-acid-derived fuels and chemicals from plant biomass, Nature 463, 559-U182.
6. Handke, P., Lynch, S. A., and Gill, R. T. (2011) Application and engineering of fatty acid biosynthesis in Escherichia coli for advanced fuels and chemicals, Metab. Eng. 13, 28-37.
7. Lennen, R. M., Braden, D. J., West, R. M., Dumesic, J. A., and Pfleger, B. F. (2010) A Process for Microbial Hydrocarbon Synthesis: Overproduction of Fatty Acids in Escherichia coli and Catalytic Conversion to Alkanes, Biotechnol. Bioeng. 106, 193-202.
8. Dellomonaco, C., Clomburg, J. M., Miller, E. N., and Gonzalez, R. (2011) Engineered reversal of the β-oxidation cycle for the synthesis of fuels and chemicals, Nature 476, 355-359.
9. Keasling, J. D. (2008) Synthetic biology for synthetic chemistry, ACS Chem. Biol. 3, 64-76.
10. Clomburg, J. M., and Gonzalez, R. (2010) Biofuel production in Escherichia coli: the role of metabolic engineering and synthetic biology, Appl. Microbiol. Biotechnol. 86, 419-434.
11. Clark, D. P., and Cronan, J. E. (October 2005 Posting Date) Two-Carbon Compounds and Fatty Acids as Carbon Sources, In EcoSal-Escherichia coli and Salmonella: cellular and molecular biology (Neidhardt, F., Curtiss, R. I., Ingraha, J., Lin, E., Low, K., Magasanik, B., Reznikoff, W., Riley, N., Schaechter, M., and Umbarger, H., Eds.) 2nd ed., ASM Press, Washington, D.C.
12. Feigenbaum, J., and Schulz, H. (1975) Thiolases of Escherichia coli: Purification and Chain-Length Specificties, J. Bacteriol. 122, 407-411.
13. Jenkins, L. S., and Nunn, W. D. (1987) Genetic and Molecular Characterization of the Genes Involved in Short-Chain Fatty-Acid Degradation in Escherichia coli: The Ato System, J. Bacteriol. 169, 42-52.
14. Yang, S. Y., Yang, X. Y. H., Healy-Louie, G., Schulz, H., and Elzinga, M. (1990) Nucleotide Sequence of the fadA Gene: Primary Structure of the 3-ketoacyl-Coenzyme A Thiolase from Escherichia coli and the Structural Organization of the fadBA Operon, J. Biol. Chem. 265, 10424-10429.
15. Nielsen, J., Villadsen, J., and Liden, G. (2003) Bioreaction Engineering Principles, Kluwer Adademic/Plenum Publishers, New York.
16. Teufel, R., Mascaraque, V., Ismail, W., Voss, M., Perera, J., Eisenreich, W., Haehnel, W., and Fuchs, G. (2010) Bacterial phenylalanine and phenylacetate catabolic pathway revealed, Proc. Natl. Acad. Sci. U.S.A. 107, 14390-14395.
17. Binstock, J. F., and Schulz, H. (1981) Fatty acid oxidation complex from Escherichia coli, Methods Enzymol. 71, 403-411.
18. He, X. Y., and Yang, S. Y. (1997) Glutamate-119 of the large alpha-subunit is the catalytic base in the hydration of 2-trans-enoyl-coenzyme A catalyzed by the multienzyme complex of fatty acid oxidation from Escherichia coli, Biochemistry 36, 11044-11049.

19. Campbell, J. W., Morgan-Kiss, R. M., and Cronan, J. E. (2003) A new *Escherichia coli* metabolic competency: growth on fatty acids by a novel anaerobic β-oxidation pathway, *Mol. Microbiol.* 47, 793-805.
20. Gulevich, A. Y., Skorokhodova, A. Y., Sukhozhenko, A. V., Shakulov, R. S., and Debabov, V. G. (2012) Metabolic engineering of *Escherichia coli* for 1-butanol biosynthesis through the inverted aerobic fatty acid β-oxidation pathway, *Biotechnol. Lett.* 34, 463-469.
21. Eichler, K., Bourgis, F., Buchet, A., Kleber, H. P., and Mandrandberthelot, M. A. (1994) Molecular Characterization of the Cai Operon Necessary for Carnitine Metabolism in *Escherichia coli*, *Mol. Microbiol.* 13, 775-786.
22. Walt, A., and Kahn, M. L. (2002) The fixA and fixB genes are necessary for anaerobic carnitine reduction in *Escherichia coli*, *J. Bacteriol.* 184, 4044-4047.
23. Eichler, K., Buchet, A., Bourgis, F., Kleber, H. P., and Mandrandberthelot, M. A. (1995) The fix *Escherichia coli* region contains 4 genes related to carnitine metabolism, *J. Basic Microbiol.* 35, 217-227.
24. Akhtar, M. K., and Jones, P. R. (2009) Construction of a synthetic YdbK-dependent pyruvate:H-2 pathway in *Escherichia coli* BL21(DE3), *Metab. Eng.* 11, 139-147.
25. Hoffmeister, M., Piotrowski, M., Nowitzki, U., and Martin, W. (2005) Mitochondrial trans-2-enoyl-CoA reductase of wax ester fermentation from *Euglena gracilis* defines a new family of enzymes involved in lipid synthesis, *J. Biol. Chem.* 280, 4329-4338.
26. Inui, H., Miyatake, K., Nakano, Y., and Kitaoka, S. (1984) Fatty Acid Synthesis in Mitochondria of *Euglena gracilis*, *Eur. J. Biochem.* 142, 121-126.
27. Inui, H., Miyatake, K., Nakano, Y., and Kitaoka, S. (1983) Production and Composition of Wax Esters by Fermentation of *Euglena gracilis*, *Agric. Biol. Chem.* 47, 2669-2671.
28. Cho, H. S., and Cronan, J. E. (1993) *Escherichia coli* thioesterase I, molecular cloning and sequencing of the structural gene and identification as a periplasmic enzyme, *J. Biol. Chem.* 268, 9238-9245.
29. Nie, L., Ren, Y., Janakiraman, A., Smith, S., and Schulz, H. (2008) A novel paradigm of fatty acid β-oxidation exemplified by the thioesterase-dependent partial degradation of conjugated linoleic acid that fully supports growth of *Escherichia coli*, *Biochemistry* 47, 9618-9626.
30. Zhuang, Z. H., Song, F., Zhao, H., Li, L., Cao, J., Eisenstein, E., Herzberg, O., and Dunaway-Mariano, D. (2008) Divergence of function in the hot dog fold enzyme superfamily: The bacterial thioesterase YciA, *Biochemistry* 47, 2789-2796.
31. Feng, Y., and Cronan, J. E. (2009) A New Member of the *Escherichia coli* fad Regulon: Transcriptional Regulation of fadM (ybaW), *J. Bacteriol.* 191, 6320-6328.
32. Kuznetsova, E., Proudfoot, M., Sanders, S. A., Reinking, J., Savchenko, A., Arrowsmith, C. H., Edwards, A. M., and Yakunin, A. F. (2005) Enzyme genomics: Application of general enzymatic screens to discover new enzymes, *FEMS Microbiol. Rev.* 29, 263-279.
33. Vlessis, A. A., Bartos, D., and Trunkey, D. (1990) Importance of spontaneous alpha-ketoacid decarboxylation in experiments involving peroxide, *Biochem. Biophys. Res. Comm.* 170, 1281-1287.
34. Yazdani, S. S., and Gonzalez, R. (2007) Anaerobic fermentation of glycerol: a path to economic viability for the biofuels industry, *Curr. Opin. Biotechnol.* 18, 213-219.
35. Kang, Y. S., Durfee, T., Glasner, J. D., Qiu, Y., Frisch, D., Winterberg, K. M., and Blattner, F. R. (2004) Systematic mutagenesis of the *Escherichia coli* genome, *J. Bacteriol.* 186, 8548-8548.
36. Yazdani, S. S., and Gonzalez, R. (2008) Engineering *Escherichia coli* for the efficient conversion of glycerol to ethanol and co-products, *Metab. Eng.* 10, 340-351.
37. Miller, J. H. (1972) *Experiments in molecular genetics*, Cold Spring Harbor Laboratory Press, Cold Spring Harbor, N.Y.
38. Baba, T., Ara, T., Hasegawa, M., Takai, Y., Okumura, Y., Baba, M., Datsenko, K. A., Tomita, M., Wanner, B. L., and Mori, H. (2006) Construction of *Escherichia coli* K-12 in-frame, single-gene knockout mutants: the Keio collection, *Mol. Syst. Biol.* 2, 11.
39. Sambrook, J., Fritsch, E. F., Maniatis, T., and Russell, D. W. (2001) *Molecular Cloning: A Laboratory Manual*, 3rd ed., Cold Spring Harbor Laboratory Press, Cold Spring Harbor, N.Y.
40. Neidhardt, F. C., Bloch, P. L., and Smith, D. F. (1974) Culture Medium for Enterobacteria, *J. Bacteriol.* 119, 736-747.
41. Dharmadi, Y., Murarka, A., and Gonzalez, R. (2006) Anaerobic fermentation of glycerol by *Escherichia coli*: A new platform for metabolic engineering, *Biotechnol. Bioeng.* 94, 821-829.
42. Dharmadi, Y., and Gonzalez, R. (2005) A better global resolution function and a novel iterative stochastic search method for optimization of high-performance liquid chromatographic separation, *J Chromatogr., A* 1070, 89-101.
43. Vick, J. E., Johnson, E. T., Choudhary, S., Bloch, S. E., Lopez-Gallego, F., Srivastava, P., Tikh, I. B., Wawrzyn, G. T., and Schmidt-Dannert, C. (2011) Optimized compatible set of BioBrick™ vectors for metabolic pathway engineering, *Appl. Microbiol. Biotechnol.* 92, 1275-1286.
44. Kitagawa, M., Ara, T., Arifuzzaman, M., Ioka-Nakamichi, T., Inamoto, E., Toyonaga, H., and Mori, H. (2005) Complete set of ORF clones of *Escherichia coli* ASKA library (A complete Set of *E. coli* K-12 ORF archive): Unique resources for biological research, *DNA Res.* 12, 291-299.
45. Obrien, W. J., and Frerman, F. E. (1977) Evidence for a Complex of 3 β-Oxidation Enzymes in *Escherichia coli*: Induction and Localization, *J. Bacteriol.* 132, 532-540.
46. Bond-Watts, B. B., Bellerose, R. J., and Chang, M. C. Y. (2011) Enzyme mechanism as a kinetic control element for designing synthetic biofuel pathways, *Nat. Chem. Biol.* 7, 222-227.
47. Wiesenborn, D. P., Rudolph, F. B., and Papoutsakis, E. T. (1988) Thiolase from *Clostridium acetobutylicum* ATCC-824 and its Role in the Synthesis of Acids and Solvents, *Appl. Environ. Microbiol.* 54, 2717-2722.
48. Hartmanis, M. G. N., and Gatenbeck, S. (1984) Intermediary Metabolism in *Clostridium acetobutylicum*: Levels of Enzymes Involved in the Formation of Acetate and Butyrate, *Appl. Environ. Microbiol.* 47, 1277-1283.
49. Lehman, T. C., Hale, D. E., Bhala, A., and Thorpe, C. (1990) An Acyl-Coenzyme A Dehydrogenase Assay Utilizing the Feericenium Ion, *Anal. Biochem.* 186, 280-284.

The invention claimed is:

1. A genetically engineered microbe, comprising one or more overexpressed enzymes forming a reverse beta oxidation pathway, wherein overexpression of an enzyme is compared to wild type activity of that enzyme before said microbe is genetically engineered to overexpress that enzyme, wherein said reverse beta oxidation pathway comprises:
   a) overexpressed enzyme(s) that allow the production of an omega-functionalized acyl-CoA thioester primer selected from oxalyl-CoA, malonyl-CoA, succinyl-CoA, hydroxyacetyl-CoA, 3-hydroxypropionyl-CoA, 4-hydroxybutyryl-CoA, 2-aminoacetyl-CoA, 3-aminopropionoyl-CoA, 4-aminobutyrylCoA, isobutyryl-CoA, 3-methyl-butyryl-CoA, 2-hydroxypropionyl-CoA, 3-hydroxybutyryl-CoA, and 2-aminopropionyl-CoA;
   b) an overexpressed thiolase able to condense said omega-functionalized acyl-CoA primer with acetyl-CoA, and encoded by atoB, fadA, fadI, bktB, catF, paaJ, pcaF, phaA, thlA, thlB, dcaF or yqeF;
   c) an overexpressed 3-hydroxyacyl-CoA dehydrogenase able to act on an omega-functionalized 3-ketoacyl-CoA substrate;
   d) an overexpressed enoyl-CoA hydratase or 3-hydroxyacyl-CoA dehydratase able to act on an omega-functionalized 3-hydroxyacyl-CoA substrate;
   e) an overexpressed acyl-CoA dehydrogenase or trans-enoyl-CoA reductase able to act on an omega-functionalized trans-enoyl-CoA substrate; and
   f) an overexpressed termination enzyme able to act on an omega-functionalized CoA-thioester substrate or their beta-functionalized derivatives, wherein said termination enzyme is selected from:
      i) a thioesterase, or an acyl-CoA:acetyl-CoA transferase, or a phosphotransacylase and a carboxylate kinase;
      ii) an alcohol-forming coenzyme-A thioester reductase;
      iii) an aldehyde-forming CoA thioester reductase and an alcohol dehydrogenase;
      iv) an aldehyde-forming CoA thioester reductase and an aldehyde decarbonylase;
      v) an olefin-forming enzyme; and
      vi) an aldehyde-forming CoA thioester reductase and a transaminase.

2. The microbe of claim 1, wherein said overexpressed 3-hydroxyacyl-CoA dehydrogenase is encoded by fadB, fadJ, dcaH or paaH.

3. The microbe of claim 1, wherein said overexpressed enoyl-CoA hydratase is encoded by fadB, fadJ, phaJ4, phaJ1, phaJ, paaZ, dcaE or paaF.

4. The microbe of claim 1, wherein said overexpressed acyl-CoA dehydrogenase or trans-enoyl-CoA reductase is encoded by *Euglena gracilis* TER, fabI, *Cytophaga hutchinsonii* TER, *Treponima denticola* TER, *Idiomarina loihiensis* TER, *Methylobacillus flagellates* TER, ydiO, dcaA or fadE.

5. The microbe of claim 1, wherein said overexpressed thioesterase is encoded by tesA, tesB, yciA, fadM, ydiI, ybgC, *E. coli* paal, ybdB, *A. Borkumensis* tesB, *A. thaliana* ACH2, *M. musculus* acot8 or *S. cerevisiae* PTE1.

6. The microbe of claim 1, wherein said microbe is *E. coli* and comprises ΔfadR, atoC(c), ΔarcA, Δcrp, and crp*, wherein the symbol Δ means a stop mutation, deletion or frameshift.

7. The microbe of claim 1, wherein said microbe comprises ΔadhE, Δpta or ΔackA or ΔackAΔpta, ΔpoxB, ΔldhA, and ΔfrdA, wherein the symbol Δ means a stop mutation, deletion or frameshift.

8. The microbe of claim 1, further comprising overexpression of omega-oxidation enzymes selected from a cytochrome P450 monooxygenase, an alkane monooxygenase, an alcohol dehydrogenase, and an aldehyde dehydrogenase.

9. The microbe of claim 1, further comprising overexpression of alpha-oxidation enzymes selected from an acyl-CoA synthase, an acyl-CoA 2-hydroxylase, a 2-hydroxyacyl-CoA lyase, an aldehyde dehydrogenase, a fatty acid alpha-hydroxylase and an alcohol dehydrogenase.

10. The microbe of claim 1, wherein said microbe is *E. coli* and has a genotype selected from:
   a) ΔldhA ΔpoxB Δpta ΔadhE ΔfrdA THIL+ fadB+ fadE+ ydiQRST+ ydbK+ ACR+ ADH+
   b) ΔldhA ΔpoxB Δpta ΔadhE ΔfrdA THIL+ fadB+ fadE+ ydiQRST+ ydbK+ THIE+
   c) ΔldhA ΔpoxB Δpta ΔadhE ΔfrdA THIL+ fadB+ Ter+ ACR+ ADH+
   d) ΔldhA ΔpoxB Δpta ΔadhE ΔfrdA THIL+ fadB+ Ter+ THIE+
   e) ΔldhA ΔpoxB Δpta ΔadhE ΔfrdA THIL+ fadB+ ydiO+ ydiQRST+ ydbK+ ACR+ ADH+
   f) ΔldhA ΔpoxB Δpta ΔadhE ΔfrdA THIL+ fadB+ ydiO+ ydiQRST+ ydbK+ THIE+
   g) ΔldhA ΔpoxB Δpta ΔadhE ΔfrdA THIL+ fadBA+ fadE+ ydiQRST+ ydbK+ ACR+ ADH+
   h) ΔldhA ΔpoxB Δpta ΔadhE ΔfrdA THIL+ fadBA+ fadE+ ydiQRST+ ydbK+ THIE+
   i) ΔldhA ΔpoxB Δpta ΔadhE ΔfrdA THIL+ fadBA+ Ter+ ACR+ ADH+
   j) ΔldhA ΔpoxB Δpta ΔadhE ΔfrdA THIL+ fadBA+ Ter+ THIE+
   k) ΔldhA ΔpoxB Δpta ΔadhE ΔfrdA THIL+ fadBA+ ydiO+ ydiQRST+ ydbK+ ACR+ ADH+
   l) ΔldhA ΔpoxB Δpta ΔadhE ΔfrdA THIL+ fadBA+ ydiO+ ydiQRST+ ydbK+ THIE+
   m) ΔldhA ΔpoxB Δpta ΔadhE ΔfrdA THIL+ fadBA+ ydiO+ ydiQRST+ ydbK+ THIE+
   n) ΔldhA ΔpoxB Δpta ΔadhE ΔfrdA THIL+ fadBA+ ydiO+ ydiQRST+ ydbK+ THIE+
   o) ΔldhA ΔpoxB Δpta ΔadhE ΔfrdA ΔfadB ΔfadJ ΔpaaH THIL+ ACR+ ADH+
   p) ΔldhA ΔpoxB Δpta ΔadhE ΔfrdA ΔfadB ΔfadJ ΔpaaH THIL+ THIE+ q) ΔldhA ΔpoxB Δpta ΔadhE ΔfrdA ΔfadB ΔfadJ DpaaH THIL+ ACR+ ADH+
r) ΔldhA ΔpoxB Δpta ΔadhE ΔfrdA ΔfadE ΔydiO THIL+ fadB+ THIE+
s) ΔldhA ΔpoxB Δpta ΔadhE ΔfrdA ΔfadE ΔydiO THIL+ fadB+ ACR+ ADH+ and
t) ΔldhA ΔpoxB Δpta ΔadhE ΔfrdA ΔfadE ΔydiO THIL+ fadB+ THIE+ wherein Δ means stop mutation, deletion or frameshift.

11. A method of making a desired product, comprising growing the genetically engineered microbe of claim 1 in a culture broth, extending said primer by using a reverse beta oxidation pathway to produce a product at least two carbons longer than said primer, and isolating said product, wherein said product is selected from a diol, a dicarboxylic acid, a hydroxy acid, a carboxylated alcohol, an amine, an amino acid, a hydroxylated amine, a diamine, an amide, a carboxylated amide, a hydroxylated amide, a diamide, a hydroxamic acid, and β-substituted or omega-substituted derivatives thereof.

12. A method of making a desired product, comprising growing the genetically engineered microbe of claim 10 in a culture broth, extending said primer by using a reverse beta oxidation pathway to produce a product at least two carbons longer than said primer, and isolating said product, wherein said product is selected from a diol, a dicarboxylic acid, a hydroxy acid, a carboxylated alcohol, an amine, an amino acid, a hydroxylated amine, a diamine, an amide, a carboxylated amide, a hydroxylated amide, a diamide, a hydroxamic acid, and β-substituted or omega-substituted derivatives thereof.

* * * * *